US009675733B2

(12) United States Patent
Tseng et al.

(10) Patent No.: US 9,675,733 B2
(45) Date of Patent: *Jun. 13, 2017

(54) METHODS OF MODULATING BONE REMODELING

(71) Applicant: TissueTech, Inc., Doral, FL (US)

(72) Inventors: Scheffer Tseng, Pinecrest, FL (US); Ek Kia Tan, Miami, FL (US); Hua He, Miami, FL (US)

(73) Assignee: TISSUETECH, INC., Doral, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/348,736

(22) Filed: Nov. 10, 2016

(65) Prior Publication Data

US 2017/0072102 A1    Mar. 16, 2017

Related U.S. Application Data

(63) Continuation of application No. 14/004,992, filed as application No. PCT/US2012/035678 on Apr. 27, 2012, now Pat. No. 9,526,770.

(60) Provisional application No. 61/480,281, filed on Apr. 28, 2011.

(51) Int. Cl.
| *A61K 35/50* | (2015.01) |
| *A61K 35/54* | (2015.01) |
| *C12N 5/00* | (2006.01) |
| *C12N 5/04* | (2006.01) |
| *A61L 27/38* | (2006.01) |
| *A61L 27/36* | (2006.01) |

(52) U.S. Cl.
CPC .......... *A61L 27/3847* (2013.01); *A61K 35/54* (2013.01); *A61L 27/3604* (2013.01); *A61L 27/365* (2013.01); *A61L 2430/02* (2013.01)

(58) Field of Classification Search
None
See application file for complete search history.

(56) References Cited

U.S. PATENT DOCUMENTS

| 3,598,122 A | 8/1971 | Zaffaroni |
| 3,598,123 A | 8/1971 | Zaffaroni |
| 3,710,795 A | 1/1973 | Higuchi et al. |
| 3,731,683 A | 5/1973 | Zaffaroni |
| 3,742,951 A | 7/1973 | Zaffaroni |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,201,211 A | 5/1980 | Chandrasekaran et al. |
| 4,230,105 A | 10/1980 | Harwood |
| 4,292,299 A | 9/1981 | Suzuki et al. |
| 4,292,303 A | 9/1981 | Keith et al. |
| 4,305,502 A | 12/1981 | Gregory et al. |
| 4,327,725 A | 5/1982 | Cortese et al. |
| 4,347,841 A | 9/1982 | Benyo et al. |
| 4,476,116 A | 10/1984 | Anik |
| 4,624,848 A | 11/1986 | Lee |
| 4,871,549 A | 10/1989 | Ueda et al. |
| 4,968,509 A | 11/1990 | Radebaugh et al. |
| 5,002,071 A | 3/1991 | Harrell |
| 5,011,692 A | 4/1991 | Fujioka et al. |
| 5,017,381 A | 5/1991 | Maruyama et al. |
| 5,033,252 A | 7/1991 | Carter |
| 5,052,558 A | 10/1991 | Carter |
| 5,093,487 A | 3/1992 | Brown et al. |
| 5,116,817 A | 5/1992 | Anik |
| 5,229,135 A | 7/1993 | Philippon et al. |
| 5,260,068 A | 11/1993 | Chen |
| 5,260,069 A | 11/1993 | Chen |
| 5,323,907 A | 6/1994 | Kalvelage |
| 5,336,168 A | 8/1994 | Sibalis |
| 5,436,135 A | 7/1995 | Tayot et al. |
| 5,437,287 A | 8/1995 | Phillips et al. |
| 5,456,923 A | 10/1995 | Nakamichi et al. |
| 5,461,140 A | 10/1995 | Heller et al. |
| 5,508,040 A | 4/1996 | Chen |

(Continued)

FOREIGN PATENT DOCUMENTS

| CN | 1193515 A | 9/1998 |
| CN | 1203794 A | 1/1999 |
| EP | 1604695 A1 | 12/2005 |
| KR | 20010098716 A | 11/2001 |
| WO | WO-03077794 A2 | 9/2003 |
| WO | WO-2004026244 A2 | 4/2004 |
| WO | WO-2004060388 A1 | 7/2004 |
| WO | WO-2006094247 A2 | 9/2006 |
| WO | WO-2007038686 A2 | 4/2007 |
| WO | WO-2011031489 A2 | 3/2011 |

OTHER PUBLICATIONS

Bae et al. Characterization of the Promoter Region of the Human Transforming Growth Factor-β Type II Receptor Gene. J. Biol. Chem. 270(49):29460-29468 (1995).

(Continued)

*Primary Examiner* — Chris R Tate
*Assistant Examiner* — Douglas F White
(74) *Attorney, Agent, or Firm* — Wilson Sonsini Goodrich & Rosati

(57) ABSTRACT

Disclosed herein, in certain instances, are methods of inhibiting osteoclast differentiation, bone resorption, bone formation, and bone remodeling in an individual in need thereof, comprising administering to the individual a composition comprising substantially fetal support tissue product including amniotic membrane and umbilical cord or an extract thereof, or a composition comprising substantially isolated HC-HA complex.

10 Claims, 24 Drawing Sheets

(56) References Cited

U.S. PATENT DOCUMENTS

| | | | |
|---|---|---|---|
| 5,516,527 | A | 5/1996 | Curatolo |
| 5,567,441 | A | 10/1996 | Chen |
| 5,622,721 | A | 4/1997 | Dansereau et al. |
| 5,665,378 | A | 9/1997 | Davis et al. |
| 5,686,105 | A | 11/1997 | Kelm et al. |
| 5,700,410 | A | 12/1997 | Nakamichi et al. |
| 5,837,280 | A | 11/1998 | Kenealy et al. |
| 5,837,284 | A | 11/1998 | Mehta et al. |
| 5,840,329 | A | 11/1998 | Bai |
| 5,869,090 | A | 2/1999 | Rosenbaum |
| 5,932,545 | A | 8/1999 | Henkin et al. |
| 5,948,766 | A | 9/1999 | Milan et al. |
| 5,977,175 | A | 11/1999 | Lin |
| 6,152,142 | A | 11/2000 | Tseng |
| 6,326,019 | B1 | 12/2001 | Tseng |
| 6,328,765 | B1 | 12/2001 | Hardwick et al. |
| 6,391,452 | B1 | 5/2002 | Antonsen et al. |
| 6,465,014 | B1 | 10/2002 | Moroni et al. |
| 6,923,983 | B2 | 8/2005 | Morgan et al. |
| 6,929,801 | B2 | 8/2005 | Klose et al. |
| 6,932,983 | B1 | 8/2005 | Straub et al. |
| 6,946,144 | B1 | 9/2005 | Jordan |
| 7,494,802 | B2 | 2/2009 | Tseng et al. |
| 8,071,135 | B2 | 12/2011 | Liu et al. |
| 8,105,634 | B2 | 1/2012 | Liu et al. |
| 8,153,162 | B2 | 4/2012 | Tseng et al. |
| 8,182,840 | B2 | 5/2012 | Tseng et al. |
| 8,182,841 | B2 | 5/2012 | Tseng et al. |
| 8,187,639 | B2 | 5/2012 | Tseng et al. |
| 8,323,701 | B2 | 12/2012 | Daniel et al. |
| 8,372,437 | B2 | 2/2013 | Daniel |
| 8,420,126 | B2 | 4/2013 | Tseng et al. |
| 8,440,235 | B2 | 5/2013 | Tseng et al. |
| 8,455,009 | B2 | 6/2013 | Tseng et al. |
| 8,460,714 | B2 | 6/2013 | Tseng et al. |
| 9,161,954 | B2 | 10/2015 | Tseng et al. |
| 9,161,955 | B2 | 10/2015 | Tseng et al. |
| 9,161,956 | B2 | 10/2015 | Tseng et al. |
| 9,175,066 | B2 | 11/2015 | Tseng et al. |
| 9,198,939 | B2 | 12/2015 | Tseng et al. |
| 2001/0041684 | A1 | 11/2001 | Lezdey et al. |
| 2004/0057938 | A1 | 3/2004 | Ghinelli |
| 2004/0126323 | A1 | 7/2004 | Shevchuk et al. |
| 2007/0202189 | A1* | 8/2007 | Ahlfors ............... A61L 27/3604 424/548 |
| 2008/0102135 | A1 | 5/2008 | Ollivier |
| 2008/0181935 | A1* | 7/2008 | Bhatia ................... A61K 38/39 424/443 |
| 2008/0193554 | A1 | 8/2008 | Dua et al. |
| 2008/0241211 | A1 | 10/2008 | Han et al. |
| 2009/0130162 | A2 | 5/2009 | Pathak et al. |
| 2009/0226499 | A1 | 9/2009 | Wisniewski et al. |
| 2010/0047214 | A1 | 2/2010 | Abramson et al. |
| 2010/0272782 | A1* | 10/2010 | Owens .................. A61L 31/005 424/443 |
| 2011/0212158 | A1 | 9/2011 | Tom et al. |
| 2011/0256202 | A1 | 10/2011 | Tom et al. |
| 2012/0141595 | A1 | 6/2012 | Tseng et al. |
| 2013/0156863 | A1 | 6/2013 | Tseng et al. |
| 2013/0344163 | A1 | 12/2013 | Tseng et al. |
| 2014/0112998 | A1 | 4/2014 | Tseng et al. |
| 2016/0095931 | A1 | 4/2016 | Tseng et al. |
| 2016/0106785 | A1 | 4/2016 | Tseng et al. |
| 2016/0129049 | A1 | 5/2016 | Tseng et al. |
| 2016/0129050 | A1 | 5/2016 | Tseng et al. |
| 2016/0129051 | A1 | 5/2016 | Tseng et al. |
| 2016/0151424 | A1 | 6/2016 | Tseng et al. |
| 2016/0184368 | A1 | 6/2016 | Tseng et al. |

OTHER PUBLICATIONS

Bhutto et al. Localization of Collagen XVIII and the Endostatin Portion of Collagen XVIII in Ages Human Control Eyes and Eyes with Age-Related Macular Degeneration. Invest. Ophthalmol. Vis. Sci. 45(5):1544-1552 (2004).

Border et al. Transforming Growth Factor-β in Disease: The Dark Side of Tissue Repair. J. Clin. Invest. 90:1-7 (1992).

Chen et al. Functions of hyaluronan in wound repair. Wound Rep Reg 7:79-89 (1999).

Chen et al. Recombinant Adenovirus Coexpressing Covalent Peptide/MHC Class II Complex and B7-1: In Vitro and In Vivo Activation of Myelin Basic Protein-Specific T Cells. J. Immunol. 167:1297-1305 (2001).

Colon et al. Transfer of Inter-α-inhibitor Heavy Chains to Hyaluronan by Surface-linked Hyaluronan-TSG-6 Complexes. J. Biol. Chem. 2009. 284:2320-2331.

Cooke et al. Comparison of cryopreserved amniotic membrane and umbilical cord tissue with dehydrated amniotic membrane/chorion tissue. J Wound Care 23(10):465-474 (2014).

Day et al. Hyaluronan cross-linking: a protective mechanism in inflammation? Trends in Immunology 26(12):637-643 (2005).

Derynk et al. TGF-β receptor signaling, Biochem. Biophys. Acta. 1333:F105-F150 (1997).

Fortunato et al. Interleukin-10 and transforming growth factor-β inhibit amniochorion tumor necrosis factor-α production by contrasting mechanisms of action: Therapeutic implications in prematurity. Am. J. Obstet. Gynecol. 177(4):803-809 (1997).

Fortunato et al. Interleukin-10 inhibition of interleukin-6 in human amniochorionic membrane: Transcriptional regulation. Am. J. Obstet. Gynecol. 175:1057-1065 (1996).

Fortunato et al. The effect of transforming growth factor and interleukin-10 on interleukin-8 release by human amniochorion may regulate histologic chorioamnionitis. Am. J. Obstet. Gynecol. 179(3):794-799 (1998).

Fries et al. Inter-alpha-inhibitor, hyaluronan and inflammation. Acta Biochim Polonica 50(3):735-742 (2003).

Gabbiani. The myofibroblast in wound healing and fibrocontractive diseases. J. Pathol. 200:500-503 (2003).

Grande. Role of Transforming Growth Factor-β in Tissue Injury and Repair. Proc. Soc. Exp. Biol. Med. 214:27-40 (1997).

Guo. Carbopol® Polymers for Pharmaceutical Drug Delivery Applications. Drug Delivery Technology 3(6):1-4 (2003).

Hales et al. TGF-β-1 induces lens cells to accumulate α-smooth muscle actin, a marker for subcapsular cataracts. Curr. Eye Res. 13:885-890 (1994).

Hanada et al. Regulation of cytokine signaling and inflammation. Cytokine & Growth Factor Reviews 13(4-5):413-421 (2002).

Hao et al. Identification of Antiangiogenic and Antiinflammatory Proteins in Human Amniotic Membrane. Cornea 19(3):348-352 (2000).

Hatano et al. Transplantation of amniotic membrane and limbal autograft in the treatment of recurrent pterygium. Clinical Ophthalmology 50(6):1101-1104 (1996) (English Abstract).

He et al. A simplified system for generating recombinant adenoviruses. PNAS USA 95:2509-2514 (1998).

He et al. Biochemical Characterization and Function of Complexes formed by Hyaluronan and the Heavy Chains of Inter-α-inhibitor (HC-HA) Purified from Extracts of Human Amniotic Membrane. J Biol Chem 284(30):20136-20146 (Jul. 24, 2009).

Heiligenhaus et al. Improvement of HSV-1 Necrotizing Keratitis with Amniotic Membrane Transplantation Invest Ophthalmol Vis Sci 42(9):1969-1974 (2001).

Hilmy et al. Physical and chemical properties of freeze-dried amnio-chorion membranes sterilized by γ irradiation. Atom Indonesia 13(2):1-3 (1987) Abstract only.

Hori. Amniotic Membrane Transplantation and Immune Reaction. Folia Ophthalmologica Japonica 56(9):722-727 (2005) (English Abstract).

Howes et al. Receptor for Advanced Glycation End Products and Age-Related Macular Degeneration. Invest. Ophthalmol. Vis. Sci. 45(10):3713-3720 (2004).

Jadin et al. Characterization of a Novel Recombinant Hyaluronan Binding Protein for Tissue Hyaluronan Detection. Journal of Histochemistry & Cytochemistry 62(9):672-683 (2014).

(56) References Cited

OTHER PUBLICATIONS

Jester et al. Corneal Stromal Wound Healing in Refractive Surgery: the Role of Myofibroblasts. Prog. Retin. Eye Res. 18(3):311-356 (1999).
Jester et al. Induction of α-Smooth Muscle Actin Expression and Myofibroblast Transformation in Cultured Cornea Keratocytes. Cornea 15(5):505-516 (1996).
Keelan et al. Activin A Exerts both Pro- and -Anti-inflammatory Effects on Human Term Gestational Tissues. Placenta 21:38-43 (2000).
Kopp et al. Abrogation of Transforming Growth Factor-beta Signaling by SMAD7 Inhibits Collagen Gel Contraction of Human Dermal Fibroblasts. J. Biol. Chem. 280(22):21570-21576 (2005).
Lawrence. Transforming Growth Factor-β: a general review. Eur. Cytokine Netw. 7:363-374 (1996).
Lee et al. An Agarose Gel Electrophoretic Method for Analysis of Hyaluronan Molecular Weight Distribution. Anal. Biochem. 219:278-287 (1994).
Li et al. An Experimental Study of the Effects of Human Amniotic Membrane on Human Retinal Pigment Epithelial Cell Proliferation in vitro. Acta Acadamiae Medicinae Militaris Tertia 25(5):407-409 (2003) (English Abstract).
Lieberman et al. Pharmaceutical Dosage Forms. 2 Ed. 1:209-214 (1990).
Liu et al. Biocompatibility and stability of disulfide-crosslinked hyaluronan films. Biomaterials 26(23):4737-4746 (2005).
Logan et al. Decorin Attenuates Gliotic Scar Formation in the Rat Cerebral Hemisphere. Exp. Neurol. 159:504-510 (1999).
Marek et al. TGF-β-(transforming growth factor-β) in chronic inflammatory conditions—a new diagnostic and prognostic marker? Med. Sci. Monitl. 8(7):RA145-RA151 (2002).
Massague et al. Controlling TGF-β signaling. Genes and Development 14:627-644 (2000).
Milner et al. TSG-6: a multifunctional protein associated with inflammation. J. Cell Sci. 116(10):1863-1873 (2003).
Moller-Pedersen et al. Neutralizing antibody to TGF-β modulates stromal fibrosis but not regression of photoablative effect following PRK. Curr. Eye Res. 17:736-747 (1998).
Monteleone et al. SMAD7 in TGF-β-mediated negative regulation of gut inflammation. Trends in Immunology 25(10):513-517 (2004).
Mukhopadhyay et al. Two distinct populations of tumor necrosis factor-stimulated gene-6 protein in the extracellular matrix of expanded mouse cumulus cell-oocyte complexes. Archives of Biochemistry and Biophysics 394(2):173-181 (2001).
Na et al. Analysis of Human Amniotic Membrane Components as Proteinase Inhibitors for Development of Therapeutic Agent for Recalcitrant Keratitis. Trophoblast Res. 13:453-466 (1999).
Nakao et al. SMAD7: a new key player in TGF-b-associated disease. Trends in Molecular Medicine 8(8):361-363 (2002).
Neumann et al. High molecular weight hyaluronic acid inhibits advanced glycation endproduct-induced NF-kB activation and cytokine expression. FEBS Ltrs. 453:283-287(1999).
Ochsner et al. Decreased expression of tumor necrosis factor-alpha-stimulated gene 6 in cumulus cells of the cyclooxygenase2 and EP2 null mice. Endocrinology 144:1008-1019 (2003).
Oikawa et al. Inhibition of Angiogenesis by 15-Deoxyspergualin. J. Antibiotics 44(9):1033-1035.
PCT/US2006/37906 International Preliminary Report on Patentability dated Apr. 1, 2008.
PCT/US2006/37906 International Search Report and Written Opinion dated Jul. 11, 2007.
PCT/US2010/032452 International Preliminary Report on Patentability dated Oct. 25, 2011.
PCT/US2010/032452 International Search Report dated Dec. 27, 2010.
PCT/US2010/46675 International Preliminary Report on Patentability dated Feb. 28, 2012.
PCT/US2010/46675 International Search Report and Written Opinion dated May 30, 2011.
PCT/US2011/042679 International Preliminary Report on Patentability dated Jan. 8, 2013.
PCT/US2011/042679 International Search Report and Written Opinion dated Mar. 9, 2012.
PCT/US2012/035678 International Preliminary Report on Patentability mailed Oct. 29, 2013.
PCT/US2012/035678 International Search Report and Written Opinion mailed Oct. 1, 2012.
Petraglia et al. Inhibin and Activin in Human Fetal Membranes: Evidence of a Local Effect on Prostaglandin Release. J. Clin. Endocrinol. Metab. 77(2):542-548 (1993).
Riley et al. Production of inhibin forms by the fetal membranes, decidua, placenta and fetus at parturition. Hum. Reprod. 15:578-583 (2000).
Romero et al. The natural interleukin-1 receptor antagonist in the fetal, maternal, and amniotic fluid compartments: The effect of gestational age, fetal gender, and intrauterine infection. Am. J. Obstet. Gynecol. 171:912-921 (1994).
Ronnov-Jessen et al. Induction of α-Smooth Muscle Actin by Transforming Growth Factor-β1 in Quiescent Human Breast Gland Fibroblasts. Lab. Invest. 68:696-707 (1993).
Rovere et al. The long pentraxin PTX3 binds to apoptotic cells and regulates their clearance by antigen-presenting dendritic cells. Blood 96(13):4300-4306 (2000).
Rugg et al, Characterization of complexes formed between TSG-6 and inter-alpha-inhibitor that act as intermediates in the covalent transfer of heavy chains onto hyaluronan. J Biol Chem 280(27):25674-25686 (2005).
Sanggaard et al, The transfer of heavy chains from bikunin proteins to hyaluronan requires both TSG-6 and HC2. J Biol Chem 283(27):18530-18537 (2008).
Serini et al. The Fibronectin Domain ED-A Is Crucial for Myofibroblastic Phenotype Induction by Transforming Growth Factor-β1. J. Cell. Biol. 142:873-881 (1998).
Shah et al. Control of scarring in adult wounds by neutralising antibody to transforming growth factor β. Lancet 339:213-214 (1992).
Singh et al. Encyclopedia of Pharmaceutical Technology 2nd Ed. pp. 751-753 (2002).
Solomon et al. Suppression of Interleukin 1a and interleukin 1b in human limbal epithelial cells cultured on the amniotic membrane stromal matrix. Br. J. Ophthalmol 85:444-449 (2001).
Tan et al. Structural and Biological Comparison of Cryopreserved and Fresh Amniotic membrane Tissues. Journal Biomaterial and Tissue Engineering 4:379-388 (2014).
Travis et al. Hyaluronan Enhances Contraction of Collagen by Smooth Muscle Cells and Adventitial Fibroblasts Role of CD44 and Implications for Constrictive Remodeling. Cir. Res. 88:77-83 (2001).
Tseng et al. How Does Amniotic Membrane Work? Ocular Surface J. 2(3):177-187 (2004).
Tseng et al. Suppression of Transforming Growth Factor-Beta Isoforms, TGF-β Receptor Type II, and Myofibroblast Differentiation in Cultured Human Corneal and Limbal Fibroblasts by Amniotic Membrane Matrix. J. Cell Physiol. 179:325-335 (1999).
U.S. Appl. No. 11/528,902 Office Action dated Apr. 2, 2009.
U.S. Appl. No. 11/528,902 Office Action dated Dec. 16, 2009.
U.S. Appl. No. 11/528,902 Office Action dated Jan. 27, 2011.
U.S. Appl. No. 11/528,902 Office Action dated Sep. 8, 2010.
U.S. Appl. No. 11/528,980 Office Action dated Aug. 11, 2009.
U.S. Appl. No. 11/528,980 Office Action dated Jan. 10, 2011.
U.S. Appl. No. 11/528,980 Office Action dated Nov. 13, 2008.
U.S. Appl. No. 11/528,980 Office Action dated Oct. 15, 2010.
U.S. Appl. No. 11/529,658 Office Action dated Apr. 3, 2009.
U.S. Appl. No. 11/529,658 Office Action dated Dec. 16, 2009.
U.S. Appl. No. 11/529,658 Office Action dated Jan. 27, 2011.
U.S. Appl. No. 11/529,658 Office Action dated Sep. 3, 2010.
U.S. Appl. No. 11/535,924 Office Action dated Dec. 16, 2009.
U.S. Appl. No. 11/535,924 Office Action dated Jan. 31, 2011.
U.S. Appl. No. 11/535,924 Office Action dated Mar. 31, 2009.
U.S. Appl. No. 11/535,924 Office Action dated Sep. 8, 2010.
U.S. Appl. No. 13/262,725 Office Action dated Feb. 25, 2015.
U.S. Appl. No. 13/262,725 Office Action dated Jul. 17, 2014.

(56) References Cited

OTHER PUBLICATIONS

U.S. Appl. No. 13/322,896 Office Action dated Jan. 20, 2016.
U.S. Appl. No. 13/322,896 Office Action dated Jul. 6, 2015.
U.S. Appl. No. 13/322,896 Office Action dated Oct. 22, 2014.
U.S. Appl. No. 13/453,840 Office Action dated Aug. 21, 2012.
U.S. Appl. No. 13/704,231 Office Action dated Aug. 2, 2016.
U.S. Appl. No. 13/704,231 Office Action dated Feb. 11, 2016.
U.S. Appl. No. 13/704,231 Office Action dated Jun. 4, 2015.
U.S. Appl. No. 13/796,761 Office Action dated Dec. 9, 2014.
U.S. Appl. No. 13/802,204 Office Action dated Aug. 7, 2015.
U.S. Appl. No. 13/802,204 Office Action dated Feb. 26, 2015.
U.S. Appl. No. 13/802,204 Office Action dated Jan. 22, 2016.
U.S. Appl. No. 13/802,264 Office Action dated Jul. 16, 2015.
U.S. Appl. No. 13/802,264 Office Action dated Nov. 28, 2014.
U.S. Appl. No. 13/802,359 Office Action dated Dec. 10, 2014.
U.S. Appl. No. 13/802,447 Office Action dated Dec. 15, 2014.
U.S. Appl. No. 14/004,992 Office Action dated Jun. 6, 2016.
U.S. Appl. No. 14/004,992 Office Action dated Nov. 23, 2015.
U.S. Appl. No. 14/886,946 Office Action dated Apr. 18, 2016.
Verbeek et al. Induction of alpha-smooth muscle actin expression in cultured human brain pericytes by transforming growth factor-beta 1. Am. J. Pathol. 144:372-382 (1994).
Yamaguchi et al. Negative regulation of transforming growth factor-β by the proteoglycan decorin. Nature 346(6281):281-284 (1990).
Ahmed et al. Expression and localization of alphavbeta6 integrin in extraplacental fetal membranes: possible role in human parturition. Mol Hum Reprod 10(3):173-179 (2004).
Temma et al. Effects of 4-hydroxy-2-nonenal, a marker of oxidative stress, on the cyclooxygenase-2 of human placenta in chorioamnionitis. Mol Hum Reprod 10(3):167-171 (2004).
U.S. Appl. No. 13/704,231 Office Action dated Jan. 19, 2017.
U.S. Appl. No. 14/240,712 Office Action dated Nov. 28, 2016.
U.S. Appl. No. 14/880,135 Office Action dated Dec. 23, 2016.
English Translation of JP74043153B (App. S45-107284) (9 pgs.) (Pub. Nov. 19, 1974).
Relucenti et al. Cumulus oophorus extracellular matrix in the human oocyte: a role for adhesive proteins. Ital J Anat Embryol 110(2 Supp 1):219-224 (2005).
Salustri et al. PTX3 plays a key role in the organization of the cumulus oophorus extracellular matrix and in in vivo fertilization. Development 131:1577-1586 (2004).
U.S. Appl. No. 14/848,148 Office Action dated Mar. 20, 2017.
Wisniewski et al., Cytokine-induced gene expression at the crossroads of innate immunity, inflammation and fertility: TSG-6 and PTX3/TSG-14. Cytokine Growth Factor Rev 15(2-3):129-146 (2004).

\* cited by examiner

METHODS OF MODULATING BONE REMODELING

CROSS-REFERENCE

This application is a continuation of U.S. application Ser. No. 14/004,992, filed Dec. 31, 2013, which is the National Phase entry of International Application No. PCT/US2012/035678, filed Apr. 27, 2012, which claims priority to U.S. Provisional Application No. 61/480,281, filed Apr. 28, 2011, all of which are incorporated herein by reference in their entireties.

SUMMARY OF THE INVENTION

Disclosed herein, in certain embodiments, are methods of inhibiting bone resorption in an individual in need thereof, comprising administering to the individual a composition comprising fetal support tissue product or an extract thereof. In some embodiments, the fetal support tissue product comprises placental amniotic membrane (PAM), umbilical cord amniotic membrane (UCAM), placenta, umbilical cord, chorion, amnion-chorion, or any combinations thereof. In some embodiments, the fetal support tissue product comprises frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the fetal support tissue product in the form of a pulverized powder or a homogenate. In some embodiments, the fetal support tissue product is cryopreserved, lyophilized, terminally sterilized, or a combination thereof. In some embodiments, the extract comprises HC-HA. In some embodiments, the extract is prepared by ultracentrifugation. In some embodiments, the extract is prepared by at least 2 rounds of ultracentrifugation. In some embodiments, the extract is prepared by more than 2 rounds of ultracentrifugation. In some embodiments, the extract is prepared by at least 4 rounds of ultracentrifugation. In some embodiments, the composition further comprises a pharmaceutically-acceptable diluent, excipient or carrier. In some embodiments, the composition is formulated as a solution, suspension, paste, ointment, oil, emulsion, microemulsion, cream, lotion, gel, or combination thereof. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is administered by an orthopaedic prosthesis. In some embodiments, the composition is administered by a bone stent. In some embodiments, the composition is a sheet and is wrapped around an osteolytic bone or an osteolytic joint. In some embodiments, the methods further comprise administering to the individual a calcium supplement.

Disclosed herein, in certain embodiments, are methods of treating a disease, disorder, or condition characterized by excessive or undesired bone resorption, the method comprising administering to an individual in need thereof a composition comprising fetal support tissue product or an extract thereof. In some embodiments, the fetal support tissue product comprises placental amniotic membrane (PAM), umbilical cord amniotic membrane (UCAM), placenta, umbilical cord, chorion, amnion-chorion, or any combinations thereof. In some embodiments, the fetal support tissue product comprises frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the fetal support tissue product in the form of a pulverized powder or a homogenate. In some embodiments, the fetal support tissue product is cryopreserved, lyophilized, terminally sterilized, or a combination thereof. In some embodiments, the extract comprises HC-HA. In some embodiments, the extract is prepared by ultracentrifugation. In some embodiments, the extract is prepared by at least 2 rounds of ultracentrifugation. In some embodiments, the extract is prepared by more than 2 rounds of ultracentrifugation. In some embodiments, the extract is prepared by at least 4 rounds of ultracentrifugation. In some embodiments, the composition further comprises a pharmaceutically-acceptable diluent, excipient or carrier. In some embodiments, the composition is formulated as a solution, suspension, paste, ointment, oil, emulsion, microemulsion, cream, lotion, gel, or combination thereof. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is administered by an orthopaedic prosthesis. In some embodiments, the composition is administered by a bone stent. In some embodiments, the composition is a sheet and is wrapped around an osteolytic bone or an osteolytic joint. In some embodiments, the methods further comprise administering to the individual a calcium supplement. In some embodiments, the disease, disorder, or condition characterized by excessive or undesired osteoclast differentiation is arthritis, osteoporosis, a bone tumor, Paget's Disease, alveolar bone degradation, or any combination thereof. In some embodiments, the arthritis is osteoarthritis, rheumatoid arthritis, psoriatic arthritis, or any combination thereof.

Disclosed herein, in certain embodiments, are methods of promoting or inducing bone formation in an individual in need thereof in an individual in need thereof, comprising administering to the individual a composition comprising fetal support tissue product or an extract thereof. In some embodiments, the fetal support tissue product comprises placental amniotic membrane (PAM), umbilical cord amniotic membrane (UCAM), placenta, umbilical cord, chorion, amnion-chorion, or any combinations thereof. In some embodiments, the fetal support tissue product comprises frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the fetal support tissue product in the form of a pulverized powder or a homogenate. In some embodiments, the fetal support tissue product is cryopreserved, lyophilized, terminally sterilized, or a combination thereof.

In some embodiments, the extract comprises HC-HA. In some embodiments, the extract is prepared by ultracentrifugation. In some embodiments, the extract is prepared by at least 2 rounds of ultracentrifugation. In some embodiments, the extract is prepared by more than 2 rounds of ultracentrifugation. In some embodiments, the extract is prepared by at least 4 rounds of ultracentrifugation. In some embodiments, the composition further comprises a pharmaceutically-acceptable diluent, excipient or carrier. In some embodiments, the composition is formulated as a solution, suspension, paste, ointment, oil, emulsion, microemulsion, cream, lotion, gel, or combination thereof. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is administered by an orthopaedic prosthesis. In some embodiments, the composition is administered by a bone stent. In some embodiments, the composition is a sheet and is wrapped around an osteolytic bone or an osteolytic joint. In some embodiments, the methods further comprise administering to the individual a calcium supplement.

Disclosed herein, in certain embodiments, are methods of treating a disease, disorder or condition characterized by a deficiency of bone formation in an individual in need thereof, the method comprising administering to an individual in need thereof a composition comprising fetal support tissue product or an extract thereof. In some embodiments, the fetal support tissue product comprises placental amniotic membrane (PAM), umbilical cord amniotic membrane (UCAM), placenta, umbilical cord, chorion, amnion-chorion, or any combinations thereof. In some embodiments, the fetal support tissue product comprises frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the fetal support tissue product in the form of a pulverized powder or a homogenate. In some embodiments, the fetal support tissue product is cryopreserved, lyophilized, terminally sterilized, or a combination thereof. In some embodiments, the extract comprises HC-HA. In some embodiments, the extract is prepared by ultracentrifugation. In some embodiments, the extract is prepared by at least 2 rounds of ultracentrifugation. In some embodiments, the extract is prepared by more than 2 rounds of ultracentrifugation. In some embodiments, the extract is prepared by at least 4 rounds of ultracentrifugation. In some embodiments, the composition further comprises a pharmaceutically-acceptable diluent, excipient or carrier. In some embodiments, the composition is formulated as a solution, suspension, paste, ointment, oil, emulsion, microemulsion, cream, lotion, gel, or combination thereof. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is administered by an orthopaedic prosthesis. In some embodiments, the composition is administered by a bone stent. In some embodiments, the composition is a sheet and is wrapped around an osteolytic bone or an osteolytic joint. In some embodiments, the methods further comprise administering to the individual a calcium supplement. In some embodiments, the disease, disorder, or condition characterized by excessive or undesired osteoclast differentiation is arthritis, osteoporosis, a bone tumor, Paget's Disease, alveolar bone degradation, or any combination thereof. In some embodiments, the arthritis is osteoarthritis, rheumatoid arthritis, psoriatic arthritis, or any combination thereof.

Disclosed herein, in certain embodiments, are methods of inhibiting bone resorption in an individual in need thereof, comprising administering to the individual a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placenta, umbilical cord, chorion, amnion-chorion, placental amniotic membrane (PAM), umbilical cord amniotic membrane (UCAM), or any combinations thereof. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is administered by an orthopaedic prosthesis. In some embodiments, the composition is administered by a bone stent. In some embodiments, the methods further comprise administering to the individual a calcium supplement. In some embodiments, the disease, disorder, or condition characterized by excessive or undesired osteoclast differentiation is arthritis, osteoporosis, alveolar bone degradation, Paget's Disease, a bone tumor, or any combination thereof.

Disclosed herein, in certain embodiments, are methods of treating a disease, disorder, or condition characterized by excessive or undesired bone resorption, the method comprising administering to an individual in need thereof a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placenta, umbilical cord, chorion, amnion-chorion, placental amniotic membrane (PAM), umbilical cord amniotic membrane (UCAM), or any combinations thereof. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is administered by an orthopaedic prosthesis. In some embodiments, the composition is administered by a bone stent. In some embodiments, the methods further comprise administering to the individual a calcium supplement. In some embodiments, the disease, disorder, or condition characterized by excessive or undesired osteoclast differentiation is arthritis, osteoporosis, alveolar bone degradation, Paget's Disease, a bone tumor, or any combination thereof.

Disclosed herein, in certain embodiments, are methods of promoting or inducing bone formation in an individual in need thereof, comprising administering to the individual a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placenta, umbilical cord, chorion, amnion-chorion, placental amniotic membrane (PAM), umbilical cord amniotic membrane (UCAM), or any combinations thereof. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an orthopaedic prosthesis. In some embodiments, the composition is administered by a bone stent. In some embodiments, the methods further comprise administering to the individual a calcium supplement. In some embodiments, the disease, disorder, or condition characterized by excessive or undesired osteoclast differentiation is arthritis, osteoporosis, alveolar bone degradation, Paget's Disease, a bone tumor, or any combination thereof.

Disclosed herein, in certain embodiments, are methods of treating a disease, disorder or condition characterized by a deficiency of bone formation in an individual in need thereof, the method comprising administering to an individual in need thereof a composition comprising substantially isolated HC-HA complex. In some embodiments, the HC-HA complex is obtained by a process comprising: (a) providing a reaction mixture comprising: ((i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placenta, umbilical cord, chorion, amnion-chorion, placental amniotic membrane (PAM), umbilical cord amniotic membrane (UCAM), or any combinations thereof. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is administered by an orthopaedic prosthesis. In some embodiments, the composition is administered by a bone stent. In some embodiments, the methods further comprise administering to the individual a calcium supplement. In some embodiments, the disease, disorder, or condition characterized by excessive or undesired osteoclast differentiation is arthritis, osteoporosis, alveolar bone degradation, Paget's Disease, a bone tumor, or any combination thereof.

Disclosed herein, in certain embodiments, are patches comprising fetal support tissue product or an extract thereof. In some embodiments, the fetal support tissue product comprises placental amniotic membrane (PAM), umbilical cord amniotic membrane (UCAM), placenta, umbilical cord, chorion, amnion-chorion, or any combinations thereof. In some embodiments, the fetal support tissue product comprises frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the fetal support tissue product in the form of a pulverized powder or a homogenate. In some embodiments, the extract comprises HC-HA.

Disclosed herein, in certain embodiments, are patches comprising substantially isolated HC-HA. In some embodiments, the substantially isolated HC-HA complex is provided in a composition comprising fetal support tissue product or in an extract of fetal support tissue product. In some embodiments, the substantially isolated HC-HA complex is obtained by a process comprising: (a) providing a reaction mixture comprising: (i) HA; (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placenta, umbilical cord, chorion, amnion-chorion, placental amniotic membrane (PAM), umbilical cord amniotic membrane (UCAM), or any combinations thereof. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof.

Disclosed herein, in certain embodiments, are bone implants comprising fetal support tissue product or an extract thereof. In some embodiments, the bone implant is a bone stent or an osseointegrated implant. In some embodiments, the fetal support tissue product or the extract thereof is coated onto the outside of the bone implant. In some embodiments, the fetal support tissue product or the extract thereof elutes from the bone implant. In some embodiments, the fetal support tissue product comprises placental amniotic membrane (PAM), umbilical cord amniotic membrane (UCAM), placenta, umbilical cord, chorion, amnion-chorion, or any combinations thereof. In some embodiments, the fetal support tissue product comprises frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the fetal support tissue product in the form of a pulverized powder or a homogenate. In some embodiments, the extract comprises HC-HA.

Disclosed herein, in certain embodiments, are bone implants comprising substantially isolated HC-HA. In some embodiments, the bone implant is a bone stent or an osseointegrated implant. In some embodiments, the substantially isolated HC-HA is coated onto the outside of the bone implant. In some embodiments, the substantially isolated HC-HA elutes from the bone implant. In some embodiments, the substantially isolated HC-HA complex is provided in a composition comprising fetal support tissue product or in an extract of fetal support tissue product. In some embodiments, the substantially isolated HC-HA complex is obtained by a process comprising: (a) providing a reaction mixture comprising: (i) HA; (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placenta, umbilical cord, chorion, amnion-chorion, placental amniotic membrane (PAM), umbilical cord amniotic membrane (UCAM), or any combinations thereof. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof.

Disclosed herein, in certain embodiments, are compositions for administration to a bone comprising fetal support tissue product or an extract thereof. In some embodiments, the composition is administered by injection, a bone implant or a patch. In some embodiments, the bone implant is a bone stent. In some embodiments, the fetal support tissue product or the extract thereof is coated onto the outside of a bone implant. In some embodiments, the fetal support tissue product or the extract thereof elutes from the bone implant. In some embodiments, the fetal support tissue product comprises placental amniotic membrane (PAM), umbilical cord amniotic membrane (UCAM), placenta, umbilical cord, chorion, amnion-chorion, or any combinations thereof. In some embodiments, the fetal support tissue product comprises frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the fetal support tissue product in the form of a pulverized powder or a homogenate. In some embodiments, the extract comprises HC-HA.

Disclosed herein, in certain embodiments, are compositions for administration to a bone comprising substantially isolated HC-HA. In some embodiments, the composition is administered by injection, a bone implant or a patch. In some embodiments, the bone implant is a bone stent. In some embodiments, the fetal support tissue product or the extract thereof is coated onto the outside of a bone implant. In some embodiments, the fetal support tissue product or the extract thereof elutes from the bone implant. In some embodiments, the substantially isolated HC-HA complex is provided in a composition comprising fetal support tissue product or in an extract of fetal support tissue product. In some embodiments, the substantially isolated HC-HA complex is obtained by a process comprising: (a) providing a reaction mixture comprising: (i) HA; (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placenta, umbilical cord, chorion, amnion-chorion, placental amniotic membrane (PAM), umbilical cord amniotic membrane (UCAM), or any combinations thereof. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof.

Disclosed herein, in certain embodiments, are methods of inhibiting osteoclast differentiation in an individual in need thereof, comprising administering to the individual a composition comprising product fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the composition is formulated into an orthopaedic prosthesis. In some embodiments, the fetal support tissue product is in the form of a sheet. In some embodiments, the composition further comprises a backing. In some embodiments, the composition is wrapped around an osteolytic bone or an osteolytic joint. In some embodiments, the methods further comprise administering to the individual a calcium supplement.

Disclosed herein, in certain embodiments, are methods of promoting mineralization by osteoblasts in an individual in need thereof, comprising administering to the individual a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the composition is formulated into an orthopaedic prosthesis. In some embodiments, the fetal support tissue product is in the form of a sheet. In some embodiments, the composition further comprises a backing. In some embodiments, the composition is wrapped around an osteolytic bone or an osteolytic joint. In some embodiments, the methods further comprise administering to the individual a calcium supplement.

Disclosed herein, in certain embodiments, are methods of inhibiting bone resorption in an individual in need thereof, comprising administering to the individual a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement.

Disclosed herein, in certain embodiments, are methods of inhibiting bone remodeling in an individual in need thereof, comprising administering to the individual a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement.

Disclosed herein, in certain embodiments, are methods of balancing bone resorption and bone formation, comprising administering to an individual in need thereof a therapeutically-effective amount of a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement.

Disclosed herein, in certain embodiments, are methods of treating a disease, disorder, or condition characterized by excessive or undesired osteoclast differentiation, the methods comprising administering to an individual in need thereof a therapeutically-effective amount of a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement.

Disclosed herein, in certain embodiments, are methods of treating a disease, disorder, or condition characterized by excessive or undesired bone absorption by osteoclasts, the methods comprising administering to an individual in need thereof a therapeutically-effective amount of a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement.

Disclosed herein, in certain embodiments, are methods of treating a disease, disorder, or condition characterized by deficient or defective bone formation, the methods comprising administering to an individual in need thereof a therapeutically-effective amount of a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement.

Disclosed herein, in certain embodiments, are methods of treating arthritis, the methods comprising administering to an individual in need thereof a therapeutically-effective amount of a composition comprising a fetal support tissue product or an extract thereof. In some embodiments, the arthritis is osteoarthritis, rheumatoid arthritis, psoriatic arthritis, or any combination thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement. In some embodiments, the methods further comprise administering to the individual an NSAID, a corticosteroid, hyaluronan injections, a DMARD, an analgesic, or any combination thereof.

Disclosed herein, in certain embodiments, are methods of treating osteoporosis, the methods comprising administering to an individual in need thereof a therapeutically-effective amount of a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement. In some embodiments, the methods further comprise administering to the individual a bisphosphonate, an estrogen analog, Raloxifene, Calcitonin, Teriparatide, calcium salts, sodium fluoride, RANKL inhibitors, Strontium ranelate, or any combination thereof.

Disclosed herein, in certain embodiments, are methods of treating alveolar bone degradation, the methods comprising administering to an individual in need thereof a therapeutically-effective amount of a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is administered by a patch. In some embodiments, the patch is placed on the alveolar bone. In some embodiments, the composition is administered by an implant. In some embodiments, the implant is placed on the alveolar bone. In some embodiments, the fetal support tissue product is in the form of a substantially-flattened sheet. In some embodiments, the composition further comprises a backing. In some embodiments, the composition is placed on the alveolar bone.

Disclosed herein, in certain embodiments, are methods of treating Paget's disease, the methods comprising administering to an individual in need thereof a therapeutically-effective amount of a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement. In some embodiments, the methods further comprise administering to the individual a bisphosphonate.

Disclosed herein, in certain embodiments, are methods of treating a bone tumor, the methods comprising administering to an individual in need thereof a therapeutically-effective amount of a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. In some embodiments, the fetal support tissue product is frozen or previously frozen PAM, frozen or previously frozen UCAM, frozen or previously frozen placenta, frozen or previously frozen umbilical cord, frozen or previously frozen chorion, frozen or previously frozen amnion-chorion, or any combinations thereof. In some embodiments, the fetal support tissue product is cryopreserved, lyophilized, terminally sterilized, or a combination thereof. In some embodiments, the fetal support tissue product is in the form of a pulverized powder or a homogenate tissue product. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement. In some embodiments, the methods further comprise administering to the individual a chemotherapeutic agent, a bisphosphinate, Metastron, or any combination thereof.

Disclosed herein, in certain embodiments, are methods of inhibiting osteoclast differentiation in an individual in need thereof, comprising administering to the individual a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii); (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion, and is optionally biochemically purified. In some embodiments, the HC-HA is purified by ultracentrifugation (e.g., four rounds of ultracentrifugation). In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion or frozen or previously frozen amnion-chorion, and is optionally biochemically purified. In some embodiments, the HC-HA is purified by ultracentrifugation (e.g., four rounds of ultracentrifugation). In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the methods further comprise administering to the individual a calcium supplement.

Disclosed herein, in certain embodiments, are methods of promoting mineralization by osteoblasts in an individual in need thereof, comprising administering to the individual a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii); (iii) TSG-6; wherein the TSG-6 is optionally recombinant; and (iv) PTX3, wherein the PTX3 is optionally recombinant; wherein at least one of HA, IαI, TSG-6, TSG-6 like protein is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion, and is optionally biochemically purified. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, or frozen or previously frozen amnion-chorion, and is optionally biochemically purified. In some embodiments, the HC-HA is purified by ultracentrifugation (e.g., four rounds of ultracentrifugation). In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the methods further comprise administering to the individual a calcium supplement.

Disclosed herein, in certain embodiments, are methods of inhibiting bone resorption in an individual in need thereof, comprising administering to the individual a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii); (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion, and is optionally biochemically purified. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion or frozen or previously frozen amnion-chorion, and is optionally biochemically purified. In some embodiments, the HC-HA is purified by ultracentrifugation (e.g., four rounds of ultracentrifugation). In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the methods further comprise administering to the individual a calcium supplement.

Disclosed herein, in certain embodiments, are methods of inhibiting bone remodeling in an individual in need thereof, comprising administering to the individual a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion or frozen or previously frozen amnion-chorion. In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the methods further comprise administering to the individual a calcium supplement.

Disclosed herein, in certain embodiments, are methods of balancing bone resorption and bone formation, comprising administering to an individual in need thereof a therapeutically-effective amount of a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion, and is optionally biochemically purified. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion or frozen or previously frozen amnion-chorion, and is optionally biochemically purified. In some embodiments, the HC-HA is purified by ultracentrifugation (e.g., four rounds of ultracentrifugation). In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the methods further comprise administering to the individual a calcium supplement.

Disclosed herein, in certain embodiments, are methods of treating a disease, disorder, or condition characterized by excessive or undesired osteoclast differentiation, the methods comprising administering to an individual in need thereof a therapeutically-effective amount of a composition comprising substantially isolated HC-HA complex. In some embodiments, the HC-HA complex is obtained by a process comprising: (a) providing a reaction mixture comprising: (i) HA (e.g., HMW HA); (ii) I$\alpha$I, wherein the I$\alpha$I is optionally in serum or isolated from serum; (iii); (iii) TSG-6, wherein the TSG-6 is optionally recombinant; and (iv) PTX3, wherein the PTX3 is optionally recombinant; wherein at least one of HA, I$\alpha$I, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion, and is optionally biochemically purified. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion or frozen or previously frozen amnion-chorion, and is optionally biochemically purified. In some embodiments, the HC-HA is purified by ultracentrifugation (e.g., four rounds of ultracentrifugation). In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the methods further comprise administering to the individual a calcium supplement.

Disclosed herein, in certain embodiments, are methods of treating a disease, disorder, or condition characterized by deficient or defective bone formation, the methods comprising administering to an individual in need thereof a therapeutically-effective amount of a composition comprising substantially isolated HC-HA complex. In some embodiments, the HC-HA complex is obtained by a process comprising: (a) providing a reaction mixture comprising: (i) HA (e.g., HMW HA); (ii) I$\alpha$I, wherein the I$\alpha$I is optionally in serum or isolated from serum; (iii); (iii) TSG-6, wherein the TSG-6 is optionally recombinant; and (iv) PTX3, wherein the PTX3 is optionally recombinant; wherein at least one of HA, I$\alpha$I, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion, and is optionally biochemically purified. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion or frozen or previously frozen amnion-chorion, and is optionally biochemically purified. In some embodiments, the HC-HA is purified by ultracentrifugation (e.g., four rounds of ultracentrifugation). In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the methods further comprise administering to the individual a calcium supplement.

Disclosed herein, in certain embodiments, are methods of treating arthritis, the methods comprising administering to an individual in need thereof a therapeutically-effective amount of a composition comprising substantially isolated HC-HA complex. In some embodiments, the arthritis is osteoarthritis, rheumatoid arthritis, psoriatic arthritis, or any combination thereof. In some embodiments, the HC-HA complex is obtained by a process comprising: (a) providing a reaction mixture comprising: (i) HA (e.g., HMW HA); (ii) I$\alpha$I, wherein the I$\alpha$I is optionally in serum or isolated from serum; (iii); (iii) TSG-6, wherein the TSG-6 is optionally recombinant; and (iv) PTX3, wherein the PTX3 is optionally recombinant; wherein at least one of HA, I$\alpha$I, TSG-6, or PTX3 is optionally generated by a plurality of cells present in the reaction mixture; (b) incubating the reaction mixture for a period of time sufficient to produce HC-HA complex;

and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion, and is optionally biochemically purified. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion or frozen or previously frozen amnion-chorion, and is optionally biochemically purified. In some embodiments, the HC-HA is purified by ultracentrifugation (e.g., four rounds of ultracentrifugation). In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the methods further comprise administering to the individual a calcium supplement. In some embodiments, the methods further comprise administering to the individual an NSAID, a corticosteroid, hyaluronan injections, a DMARD, an analgesic, or any combination thereof.

Disclosed herein, in certain embodiments, are methods of treating osteoporosis, the methods comprising administering to an individual in need thereof a therapeutically-effective amount of a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii); (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion, and is optionally biochemically purified. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion or frozen or previously frozen amnion-chorion, and is optionally biochemically purified. In some embodiments, the HC-HA is purified by ultracentrifugation (e.g., four rounds of ultracentrifugation). In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the methods further comprise administering to the individual a calcium supplement. In some embodiments, the methods further comprise administering to the individual a bisphosphonate, an estrogen analog, Raloxifene, Calcitonin, Teriparatide, calcium salts, sodium fluoride, RANKL inhibitors, Strontium ranelate, or any combination thereof.

Disclosed herein, in certain embodiments, are methods of treating alveolar bone degradation, the methods comprising administering to an individual in need thereof a therapeutically-effective amount of a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion, and is optionally biochemically purified. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion or frozen or previously frozen amnion-chorion, and is optionally biochemically purified. In some embodiments, the HC-HA is purified by ultracentrifugation (e.g., four rounds of ultracentrifugation). In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is administered by a patch. In some embodiments, the patch is placed on the alveolar bone. In some embodiments, the composition is administered by an implant. In some embodiments, the implant is placed on an alveolar bone. In some embodiments, the methods further comprise administering to the individual a calcium supplement.

Disclosed herein, in certain embodiments, are methods of treating Paget's disease, the methods comprising administering to an individual in need thereof a therapeutically-effective amount of a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion, and is optionally biochemically purified. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion or frozen or previously frozen amnion-chorion, and is optionally biochemically purified. In some embodiments, the HC-HA is purified by ultracentrifugation (e.g., four rounds of ultracentrifugation). In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the methods further comprise administering to the individual a calcium supplement. In some embodiments, the methods further comprise administering to the individual a bisphosphonate.

Disclosed herein, in certain embodiments, are methods of treating a bone tumor, the methods comprising administering to an individual in need thereof a therapeutically-effective amount of a composition comprising substantially isolated HC-HA complex. In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the substantially isolated HC-HA complex is derived from placental amniotic membrane (PAM), umbilical cord amniotic membrane (UCAM), placenta, umbilical cord, chorion or amnion-chorion, and is optionally biochemically purified. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion or frozen or previously frozen amnion-chorion, and is optionally biochemically purified. In some embodiments, the HC-HA is purified by ultracentrifugation (e.g., four rounds of ultracentrifugation). In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the methods further comprise administering to the individual a calcium supplement. In some embodiments, the methods further comprise administering to the individual a chemotherapeutic agent, a bisphosphinate, Metastron, or any combination thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 1:
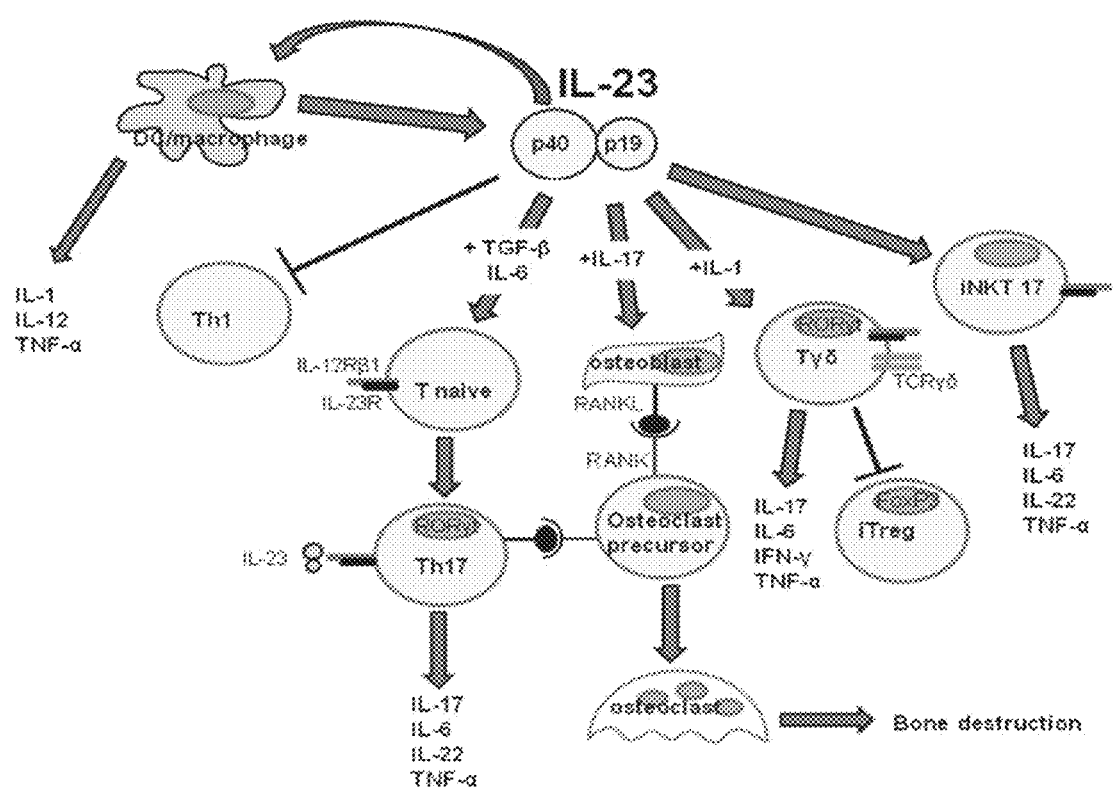
FIG. 1 exemplifies the formation of osteoclast is regulated by RANK/RANKL and its downstream signaling pathway. NFATc1 is a critical transcriptional factor that regulates the expression of osteoclastogenesis-related genes including TRAP.

The abbreviation AME means amniotic membrane extract. AME was made by extraction of amniotic membrane with PBS followed by centrifugation to remove the pellet.

The abbreviation AML means amniotic membrane lysate. AML was made by homogenating the wet amniotic membrane without adding any buffers. The abbreviation AMP means amniotic membrane powder. AMP was made by lyophilizing amniotic membrane followed by pulverizing it into powder.

DETAILED DESCRIPTION OF THE INVENTION

Certain Definitions

As used herein, "placenta" means the organ that connects a developing fetus to the maternal uterine wall to allow nutrient uptake, waste elimination, and gas exchange via the maternal blood supply. The placenta is composed of three layers. The innermost placental layer surrounding the fetus is called amnion. The allantois is the middle layer of the placenta (derived from the embryonic hindgut); blood vessels originating from the umbilicus traverse this membrane. The outermost layer of the placenta, the chorion, comes into contact with the endometrium. The chorion and allantois fuse to form the chorioallantoic membrane.

As used herein, "chorion" means the membrane formed by extraembryonic mesoderm and the two layers of trophoblast. The chorionic villi emerge from the chorion, invade the endometrium, and allow transfer of nutrients from maternal blood to fetal blood. The chorion consists of two layers: an outer formed by the trophoblast, and an inner formed by the somatic mesoderm; the amnion is in contact with the latter. The trophoblast is made up of an internal layer of cubical or prismatic cells, the cytotrophoblast or layer of Langhans, and an external layer of richly nucleated protoplasm devoid of cell boundaries, the syncytiotrophoblast. The avascular amnion is adherent to the inner layer of the chorion.

As used herein, "amnion-chorion" means a product comprising amnion and chorion. In some embodiments, the amnion and the chorion are not separated (i.e., the amnion is naturally adherent to the inner layer of the chorion). In some embodiments, the amnion is initially separated from the chorion and later combined with the chorion during processing.

As used herein, "umbilical cord" means the organ that connects a developing fetus to the placenta. The umbilical cord is composed of Wharton's jelly, a gelatinous substance made largely from mucopolysaccharides. It contains one vein, which carries oxygenated, nutrient-rich blood to the fetus, and two arteries that carry deoxygenated, nutrient-depleted blood away.

As used herein, "placental amniotic membrane" (PAM) means amniotic membrane derived from the placenta. In some embodiments, the PAM is substantially isolated.

As used herein, "umbilical cord amniotic membrane" (UCAM) means amniotic membrane derived from the umbilical cord. UCAM is a translucent membrane. The UCAM has multiple layers an epithelial layer, a basement membrane; a compact layer; a fibroblast layer; and a spongy layer. It lacks blood vessels or a direct blood supply. In some embodiments, the UCAM is substantially isolated. In some embodiments, the UCAM comprises Wharton's Jelly. In some embodiments, the UCAM comprises blood vessels and/or arteries. In some embodiments, the UCAM comprises Wharton's Jelly and blood vessels and/or arteries.

As used herein, "human cells, tissues, or cellular or tissue-based products (HCT/Ps)" means articles containing or consisting of human cells or tissues that are intended for implantation, transplantation, infusion, or transfer into a human recipient.

As used herein, "minimal manipulation" means (1) for structural tissue, processing that does not alter the original relevant characteristics of the tissue relating to the tissue's utility for reconstruction, repair, or replacement; and (2) for cells or nonstructural tissues, processing that does not alter the relevant biological characteristics of cells or tissues.

As used herein, 'homologous use" means the repair, reconstruction, replacement, or supplementation of a recipient's cells or tissues with an HCT/P that performs the same basic function or functions in the recipient as in the donor.

As used herein, "fetal support tissue product" means any product comprising tissue that is supports the development of a fetus. Examples of fetal support tissue include, but are not limited to, (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof. In some embodiments, the fetal support tissue product is a sheet, a powder, or homogenate.

As used herein, "HC-HA", means the covalent complex formed between heavy chains (HCs) of inter-alpha-inhibitor (IαI) and hyaluronan (HA) by the catalytic action of tumor necrosis factor (TNF)-stimulated gene-6 (TSG-6).

As used herein, "sheet" means any continuous expanse or surface. In some embodiments, a fetal support tissue product described herein is a flat sheet. The sheet can be any shape and size. In some embodiments, the sheet is a square, circle, triangle, or rectangle. In some embodiments, the sheet comprises multiple layers (e.g., of chorion, amnion-chorion, UCAM, PAM, placenta, umbilical cord or any combinations thereof).

As used herein, "homogenized" means (a fetal support tissue product that has been broken up into particles that are of substantially uniform size.

"Substantially isolated" or "isolated" means that the fetal support tissue product has been separate from undesired materials (e.g., red blood cells, blood vessels, and arteries) derived from the original source organism. Purity, or "isolation" may be assayed by standard methods, and will ordinarily be at least about 10% pure, more ordinarily at least about 20% pure, generally at least about 30% pure, and more generally at least about 40% pure; in further embodiments at least about 50% pure, or more often at least about 60% pure; in still other embodiments, at least about 95% pure.

As used herein, the substantial preservation of biological activity or structural integrity means that when compared to the biological activity and structural integrity of non-processed tissue, the biological activity and structural integrity of the fetal support tissue product has only decreased by about 5%, about 10%, about 15%, about 20%, about 25%, about 30%, about 35%, about 40%, about 50%, about 60%.

The term "fresh" refers to tissue that is less than 10 days old following birth, and which is in substantially the same form as it was following birth.

As used herein, "biological activity" means the activity of polypeptides and polysaccharides. In some embodiments, the activity of polypeptides and polysaccharides found in umbilical cord (and substantially isolated umbilical cord), UCAM (and substantially isolated UCAM), placenta (and substantially isolated placenta), PAM (and substantially isolated PAM), chorion (and substantially isolated chorion), or amnion-chorion (and substantially isolated amnion-chorion).

As used herein, "structural integrity" means the integrity of stroma and basement membrane that make up the UCAM, chorion, or amnion-chorion. In some embodiments, the structural integrity of the UCAM results in suture pull out strength.

As used herein, "hyaluronan" (or "HA") means a substantially non-sulfated or non-sulfated glycosaminoglycan with linear repeating disaccharide units of glucuronosyl-N-acetylglucosamine. In some embodiments, HA is obtained from a commercial supplier (e.g., Sigma Aldrich or Abbott Medical Optics, Irvine, Calif.). In some embodiments, HA is obtained from a commercial supplier as a powder. In some embodiments, HA is obtained from a cell that expresses a hyaluronan synthases (e.g., HAS1, HAS2, and HAS3). In certain instances, an HA synthase lengthens hyaluronan by repeatedly adding glucuronic acid and N-acetylglucosamine to the nascent polysaccharide as it is extruded through the cell membrane into the extracellular space.

As used herein, "recombinant TSG-6" means a TSG-6 protein that is produced by recombinant methods (i.e., the TSG-6 gene from a first source (e.g., a human TSG-6 gene) is cloned into a DNA molecule from a second source (e.g., a bacterial plasmid).

As used herein, "recombinant PTX3" means a PTX3 protein that is produced by recombinant methods (i.e., the PTX3 gene from a first source (e.g., a human PTX3 gene) is cloned into a DNA molecule from a second source (e.g., a bacterial plasmid).

As used herein, the "production bioreactor" is the bioreactor in which the final HC-HA complex disclosed herein is made.

The terms "subject" and "individual" are used interchangeably. As used herein, both terms mean any animal, preferably a mammal, including a human or non-human. The terms patient, subject, and individual are used interchangeably. None of the terms are to be interpreted as requiring the supervision of a medical professional (e.g., a doctor, nurse, physician's assistant, orderly, hospice worker).

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Methods of Use

Bone Remodeling

Bone remodeling (or bone metabolism) is the process by which mature bone tissue is removed from the skeleton (bone resorption) and new bone tissue is formed (ossification).

Bone resorption is the process by which osteoclasts break down bone, releasing minerals from bone into the blood. Osteoclasts are large multinucleated cells formed by the fusion of cells from the monocyte/macrophage cell line. Osteoclasts are generally present on the outer layer of bone, just beneath the periosteum. Attachment of the osteoclast to the osteon begins the process. The osteoclast then induces an infolding of its cell membrane and secretes collagenase. Calcium, magnesium, phosphate and products of collagen are released into blood as the osteoclasts tunnel into the mineralized bone. Osteoclasts have been indicated in skeletal diseases such as osteoporosis, rheumatoid arthritis and Paget's disease, and are responsible for osteolysis.

Osteoclasts have been indicated in skeletal diseases such as osteoporosis, rheumatoid arthritis and Paget's disease, and are responsible for osteolysis.

As used herein, "osteolysis" means refers to the degeneration and/or dissolution of bone. In some embodiments, osteolysis is the process of bone resorption, whereby the bone salts can be withdrawn by a humoral mechanism and returned to the tissue fluids, leaving behind a decalcified bone matrix. Osteolysis can be caused, inter alia, by disease, infection or ischemia.

Ossification (or, bone formation/mineralization) is the process by which osteoblasts lay down bone. There are two processes resulting in the formation of normal, healthy bone tissue: intramembranous ossification is the direct laying down of bone into the primitive connective tissue (mesenchyme), while endochondral ossification involves cartilage as a precursor.

Osteoblasts are fibroblasts that express bone sialoprotein and osteocalcin. Osteoblasts produce a matrix of osteoid, which is composed mainly of Type I collagen. Osteoblasts are also responsible for mineralization of this matrix. Zinc, copper and sodium are some of the minerals required in this process. The number of osteoblasts tends to decrease with age, affecting the balance of formation and resorption in the bone tissue, and potentially leading to osteoporosis.

Disclosed herein, in certain embodiments, are methods of inhibiting bone resorption in an individual in need thereof, comprising administering to the individual a composition comprising fetal support tissue or an extract thereof. In some embodiments, the bone resorption is undesired or excessive. In some embodiments, inhibiting bone resorption promotes mineralization by osteoblasts. In some embodiments, inhibiting bone resorption inhibits undesired or excessive bone remodeling. In some embodiments, inhibiting bone resorption balances bone resorption and bone formation. Further disclosed herein, in certain embodiments, are methods of treating a disease, disorder, or condition characterized by excessive or undesired bone resorption, the method comprising administering to an individual in need thereof a composition comprising substantially isolated amniotic membrane or an extract thereof. Additionally disclosed herein, in certain embodiments, are methods of inhibiting osteoclast differentiation in an individual in need thereof, comprising administering to the individual a composition comprising fetal support tissue or an extract thereof. In some embodiments, the osteoclast differentiation is undesired or excessive. In some embodiments, inhibiting osteoclast differentiation promotes differentiation of osteoblasts and mineralization by osteoblasts. In some embodiments, inhibiting osteoclast differentiation inhibits undesired or excessive bone remodeling. In some embodiments, inhibiting osteoclast differentiation balances bone resorption and bone formation. Also disclosed herein, in certain embodiments, are methods of treating a disease, disorder, or condition characterized by excessive or undesired osteoclast differentiation, the method comprising administering to an individual in need thereof a composition comprising substantially isolated amniotic membrane or an extract thereof.

In some embodiments, the methods comprise administering to an individual in need thereof a therapeutically-effective amount of a composition comprising a fetal support tissue product or an extract thereof.

In some embodiments, the fetal support tissue product is substantially isolated amnion. In some embodiments, the fetal support tissue product is substantially isolated PAM. In some embodiments, the fetal support tissue product is substantially isolated UCAM. In some embodiments, the fetal support tissue product is substantially isolated placenta. In some embodiments, the fetal support tissue product is substantially isolated umbilical cord. In some embodiments, the fetal support tissue product is substantially isolated chorion or amnion-chorion. In some embodiments, the fetal support tissue product is frozen or previously frozen PAM. In some embodiments, the fetal support tissue product is frozen or previously frozen UCAM. In some embodiments, the fetal support tissue product is frozen or previously frozen placenta. In some embodiments, the fetal support tissue product is frozen or previously frozen umbilical cord. In some embodiments, the fetal support tissue product is frozen or previously frozen chorion or amnion-chorion. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the fetal support tissue product is cryopreserved, lyophilized, terminally sterilized, or a combination thereof. In some embodiments, the fetal support tissue product is in the form of a pulverized powder or a homogenate.

In some embodiments, the methods comprise administering to an individual in need thereof a therapeutically-effective amount of a composition comprising substantially isolated HC-HA complex. In some embodiments, the substantially isolated HC-HA complex is derived from amnion (PAM or UCAM), placenta, umbilical cord, or chorion. In some embodiments, the substantially isolated HC-HA complex is derived from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof. In some embodiments, the HC-HA complex is HC-HAHC-HA obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex.

In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated HC-HA formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis.

Arthritis

Arthritis is a joint disorder that involves inflammation of one or more joints. There are over 100 different forms of arthritis. The most common form, osteoarthritis (degenerative joint disease), is a result of trauma to the joint, infection of the joint, or age. Other arthritis forms are rheumatoid arthritis, psoriatic arthritis, and related autoimmune diseases. Septic arthritis is caused by joint infection. Symptoms common to all arthritic disorders include pain, swelling, and joint stiffness, Osteoarthritis is the most common form of arthritis. It affects both the larger and the smaller joints of the body, for example the hands, feet, back, hip or knee. Osteoarthritis develops as a result of wear on joints or injury to joints. Osteoarthritis begins in the cartilage and eventually causes the two opposing bones to erode into each other. Osteoarthritis typically affects the weight bearing joints such as the back, spine, and pelvis. Osteoarthritis is most commonly a disease of the elderly. More than 30 percent of females have some degree of osteoarthritis by age 65. Risk factors for osteoarthritis include: prior joint trauma, obesity, and a sedentary lifestyle.

Rheumatoid arthritis is a disorder in which the body's immune system starts to attack body tissues. In rheumatoid arthritis, most damage occurs to the joint lining and cartilage which eventually results in erosion of two opposing bones. Rheumatoid arthritis often affects joints in the fingers, wrists, knees and elbows. The disease is symmetrical (appears on both sides of the body) and can lead to severe deformity. Rheumatoid arthritis occurs mostly in people aged 20 and above.

Osteoclasts are often found in the affected joints of individuals with arthritis and exacerbate bone and joint destruction. Thus, disclosed herein, in certain embodiments, are methods of treating arthritis. In some embodiments, the methods comprise administering to an individual in need thereof a therapeutically-effective amount of a composition comprising a fetal support tissue product or an extract thereof. In some embodiments, the methods comprise administering to an individual in need thereof a therapeutically-effective amount of a composition comprising substantially isolated HC-HA complex. In some embodiments, the arthritis is osteoarthritis, rheumatoid arthritis, psoriatic arthritis, or any combination thereof.

In some embodiments, the methods comprise administering to an individual in need thereof a therapeutically-effective amount of a composition comprising a fetal support tissue product or an extract thereof.

In some embodiments, the fetal support tissue product is substantially isolated amnion. In some embodiments, the fetal support tissue product is substantially isolated PAM. In some embodiments, the fetal support tissue product is substantially isolated UCAM. In some embodiments, the fetal support tissue product is substantially isolated placenta. In some embodiments, the fetal support tissue product is substantially isolated umbilical cord. In some embodiments, the fetal support tissue product is substantially isolated chorion or amnion-chorion. In some embodiments, the fetal support tissue product is frozen or previously frozen PAM. In some embodiments, the fetal support tissue product is frozen or previously frozen UCAM. In some embodiments, the fetal support tissue product is frozen or previously frozen placenta. In some embodiments, the fetal support tissue product is frozen or previously frozen umbilical cord. In some embodiments, the fetal support tissue product is frozen or previously frozen chorion or amnion-chorion. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the fetal support tissue product is cryopreserved, lyophilized, terminally sterilized, or a combination thereof. In some embodiments, the fetal support tissue product is in the form of a pulverized powder or a homogenate.

In some embodiments, the methods comprise administering to an individual in need thereof a therapeutically-effective amount of a composition comprising substantially isolated HC-HA complex. In some embodiments, the substantially isolated HC-HA complex is isolated from amnion (PAM or UCAM), placenta, umbilical cord, or chorion. In some embodiments, the substantially isolated HC-HA complex is isolated from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof.

In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex.

In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated HC-HA formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis.

In some embodiments, the methods further comprise administering to the individual a calcium supplement. In some embodiments, the methods further comprise administering to the individual an NSAID, a corticosteroid, hyaluronan injections, a DMARD, an analgesic, or any combination thereof.

Osteoporosis

Osteoporosis is a bone disease characterized by reduction of bone mineral density (BMD), deterioration of bone microarchitecture, and alteration of the amount and variety of proteins in bone. Osteoporosis is defined as a bone mineral density that is 2.5 standard deviations or more below the mean peak bone mass (average of young, healthy adults) as measured by DXA. Osteoporosis is classified as primary type 1, primary type 2, or secondary. The form of osteoporosis most common in women after menopause is referred to as primary type 1 or postmenopausal osteoporosis. Primary type 2 osteoporosis or senile osteoporosis occurs after age 75 and is seen in both females and males at a ratio of 2:1. Finally, secondary osteoporosis may arise at any age and affect men and women equally. This form of osteoporosis results from chronic predisposing medical problems or disease, or prolonged use of medications such as glucocorticoids, when the disease is called steroid- or glucocorticoid-induced osteoporosis (SIOP or GIOP).

Osteoporosis results from excessive bone resorption by osteoclasts and insufficient bone formation by osteoblasts. Thus, disclosed herein, in certain embodiments, are methods of treating osteoporosis. In some embodiments, the methods comprising administering to an individual in need thereof a therapeutically-effective amount of a composition comprising a fetal support tissue product or an extract thereof. In some embodiments, the methods comprise administering to an individual in need thereof a therapeutically-effective amount of a composition comprising substantially isolated HC-HA complex.

In some embodiments, the methods comprise administering to an individual in need thereof a therapeutically-effective amount of a composition comprising a fetal support tissue product or an extract thereof.

In some embodiments, the fetal support tissue product is substantially isolated amnion. In some embodiments, the fetal support tissue product is substantially isolated PAM. In some embodiments, the fetal support tissue product is substantially isolated UCAM. In some embodiments, the fetal support tissue product is substantially isolated placenta. In some embodiments, the fetal support tissue product is substantially isolated umbilical cord. In some embodiments, the fetal support tissue product is substantially isolated chorion or amnion-chorion. In some embodiments, the fetal support tissue product is frozen or previously frozen PAM. In some embodiments, the fetal support tissue product is frozen or previously frozen UCAM. In some embodiments, the fetal support tissue product is frozen or previously frozen placenta. In some embodiments, the fetal support tissue product is frozen or previously frozen umbilical cord. In some embodiments, the fetal support tissue product is frozen or previously frozen chorion or amnion-chorion. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the fetal support tissue product is cryopreserved, lyophilized, terminally sterilized, or a combination thereof. In some embodiments, the fetal support tissue product is in the form of a pulverized powder or a homogenate.

In some embodiments, the methods comprise administering to an individual in need thereof a therapeutically-effective amount of a composition comprising substantially isolated HC-HA complex. In some embodiments, the substantially isolated HC-HA complex is isolated from amnion (PAM or UCAM), placenta, umbilical cord, or chorion. In some embodiments, the substantially isolated HC-HA complex is isolated from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof.

In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex.

In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product or HC-HA formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement. In some embodiments, the methods further comprise administering to the individual a bisphosphonate, an estrogen analog, Raloxifene, Calcitonin, Teriparatide, calcium salts, sodium fluoride, RANKL inhibitors, Strontium ranelate, or any combination thereof.

Alveolar Bone Degradation

Degradation of the alveolar bone around the teeth often results from periodontitis. If left untreated, alveolar bone degradation may result in loss of teeth. A diagnosis of alveolar bone degradation is established by inspecting the soft gum tissues around the teeth with a probe and evaluating x-ray films to determine the amount of bone loss around the teeth.

Degradation of the alveolar bone is often exacerbated by excess bone resorption by osteoclasts and insufficient bone formation by osteoblasts. Thus, disclosed herein, in certain embodiments, are methods of treating alveolar bone degradation. In some embodiments, the methods comprising administering to an individual in need thereof a therapeutically-effective amount of a composition comprising a fetal support tissue product or an extract thereof. In some embodiments, the methods comprise administering to an individual in need thereof a therapeutically-effective amount of a composition comprising substantially isolated HC-HA complex.

In some embodiments, the methods comprise administering to an individual in need thereof a therapeutically-effective amount of a composition comprising a fetal support tissue product or an extract thereof.

In some embodiments, the fetal support tissue product is substantially isolated amnion. In some embodiments, the fetal support tissue product is substantially isolated PAM. In some embodiments, the fetal support tissue product is substantially isolated UCAM. In some embodiments, the fetal support tissue product is substantially isolated placenta. In some embodiments, the fetal support tissue product is substantially isolated umbilical cord. In some embodiments, the fetal support tissue product is substantially isolated chorion or amnion-chorion. In some embodiments, the fetal support tissue product is frozen or previously frozen PAM. In some embodiments, the fetal support tissue product is frozen or previously frozen UCAM. In some embodiments, the fetal support tissue product is frozen or previously frozen placenta. In some embodiments, the fetal support tissue product is frozen or previously frozen umbilical cord. In some embodiments, the fetal support tissue product is frozen or previously frozen chorion or amnion-chorion. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the fetal support tissue product is cryopreserved, lyophilized, terminally sterilized, or a combination thereof. In some embodiments, the fetal support tissue product is in the form of a pulverized powder or a homogenate.

In some embodiments, the methods comprise administering to an individual in need thereof a therapeutically-effective amount of a composition comprising substantially isolated HC-HA complex. In some embodiments, the substantially isolated HC-HA complex is isolated from amnion (PAM or UCAM), placenta, umbilical cord, or chorion. In some embodiments, the substantially isolated HC-HA complex is isolated from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof.

In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex.

In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product or HC-HA formulated into microspheres, microparticles, or liposomes. In some embodiments, the composition is formulated into PLGA copolymers. In some embodiments, the composition is formulated for controlled, sustained, or delayed release. In some embodiments, the composition is applied to the alveolar bone. In some embodiments, the composition is administered by a patch. In some embodiments, the patch is placed on the alveolar bone. In some embodiments, the composition is administered by an implant. In some embodiments, the implant is placed on the alveolar bone. In some embodiments, the fetal support tissue product is in the form of a substantially-flattened sheet. In some embodiments, the composition further comprises a backing. In some embodiments, the composition is wrapped around the alveolar bone. In some embodiments, the methods further comprise administering to the individual a calcium supplement.

Paget's Disease

Paget's disease is a chronic bone disorder resulting is enlarged and misshapen bones. Bones in individual with Paget's Disease are often weakened due to an imbalance in bone resorption and bone formation, resulting in pain, misshapen bones, fractures, and arthritis in the joints near the affected bones. Paget's disease typically is localized to one or a few bones. Paget's Disease may result from a viral infection or genetic factors.

Paget's disease proceeds in three stages: osteoclastic activity, mixed osteoclastic-osteoblastic activity, and exhaustive stage. The first stage is characterized by an increase in the rate of bone resorption at localized areas. These localized areas of osteolysis are seen radiologically as an advancing lytic wedge in long bones or osteoporosis circumscripta in the skull. The osteolysis is followed by a compensatory increase in bone formation induced by osteoblasts recruited to the area. Bone is laid down in a disorganized and chaotic fashion rather than the normal linear lamellar pattern. The resorbed bone is replaced and the marrow spaces are filled by an excess of fibrous connective tissue with a marked increase in blood vessels, causing the bone to become hypervascular. The bone hypercellularity may then diminish, leaving a dense "pagetic bone," also known as burned-out Paget's disease.

Paget's disease results from excessive bone resorption and insufficient bone formation. Thus, disclosed herein, in certain embodiments, are methods of treating Paget's Disease. In some embodiments, the methods comprising administering to an individual in need thereof a therapeutically-effective amount of a composition comprising a fetal support tissue product or an extract thereof. In some embodiments, the methods comprise administering to an individual in need thereof a therapeutically-effective amount of a composition comprising substantially isolated HC-HA complex.

In some embodiments, the methods comprise administering to an individual in need thereof a therapeutically-effective amount of a composition comprising a fetal support tissue product or an extract thereof.

In some embodiments, the fetal support tissue product is substantially isolated amnion. In some embodiments, the fetal support tissue product is substantially isolated PAM. In some embodiments, the fetal support tissue product is substantially isolated UCAM. In some embodiments, the fetal support tissue product is substantially isolated placenta. In some embodiments, the fetal support tissue product is substantially isolated umbilical cord. In some embodiments, the fetal support tissue product is substantially isolated chorion or amnion-chorion. In some embodiments, the fetal support tissue product is frozen or previously frozen PAM. In some embodiments, the fetal support tissue product is frozen or previously frozen UCAM. In some embodiments, the fetal support tissue product is frozen or previously frozen placenta. In some embodiments, the fetal support tissue product is frozen or previously frozen umbilical cord. In some embodiments, the fetal support tissue product is frozen or previously frozen chorion or amnion-chorion. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the fetal support tissue product is cryopreserved, lyophilized, terminally sterilized, or a combination thereof. In some embodiments, the fetal support tissue product is in the form of a pulverized powder or a homogenate.

In some embodiments, the methods comprise administering to an individual in need thereof a therapeutically-effective amount of a composition comprising substantially isolated HC-HA complex. In some embodiments, the substantially isolated HC-HA complex is isolated from amnion (PAM or UCAM), placenta, umbilical cord, or chorion. In some embodiments, the substantially isolated HC-HA complex is isolated from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof.

In some embodiments, the HC-HA complex is obtained by a process comprising: (a) providing a reaction mixture comprising: (i) HA (e.g., HMW HA); (ii) IαI, wherein the IαI is optionally in serum or isolated from serum; (iii) TSG-6, wherein the TSG-6 is optionally recombinant; and (iv) PTX3, wherein the PTX3 is optionally recombinant; wherein at least one of HA, IαI, TSG-6, or PTX3 is optionally generated by a plurality of cells present in the reaction mixture; (b) incubating the reaction mixture for a period of time sufficient to produce HC-HA complex; and (c) isolating and purifying the HC-HA complex.

In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product or HC-HA formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement. In some embodiments, the methods further comprise administering to the individual a bisphosphonate or calcitonin.

Bone Tumors

As used herein, "bone tumor" means the uncontrolled and/or undesired growth of tissue in bone. Bone tumors are either benign or malignant. They are further classified as "primary tumors", which originate in bone or from bone-derived cells and tissues, and "secondary tumors" which originate in other sites and metastasize to the bone.

Primary bone tumors may be neoplastic, developmental, traumatic, infectious, or inflammatory. Examples of benign bone tumors include osteoma, osteoid osteoma, osteochondroma, osteoblastoma, enchondroma, giant cell tumor of bone, aneurysmal bone cyst, and fibrous dysplasia of bone. Malignant primary bone tumors include osteosarcoma, chondrosarcoma, Ewing's sarcoma, fibrosarcoma, and other types.

Bone tumors often result in undesired bone degradation. Undesired bone degradation may be caused by the presence of metastatic tumor cells that stimulate formation and activation of osteoclasts. Undesired bone degradation may also arise from the formation of osteoblastic metastases. Thus, disclosed herein, in certain embodiments, are methods of treating bone tumors. In some embodiments, the methods comprising administering to an individual in need thereof a therapeutically-effective amount of a composition comprising a fetal support tissue product or an extract thereof. In some embodiments, the methods comprise administering to an individual in need thereof a therapeutically-effective amount of a composition comprising substantially isolated HC-HA complex.

In some embodiments, the methods comprise administering to an individual in need thereof a therapeutically-effective amount of a composition comprising a fetal support tissue product or an extract thereof.

In some embodiments, the fetal support tissue product is substantially isolated amnion. In some embodiments, the fetal support tissue product is substantially isolated PAM. In some embodiments, the fetal support tissue product is substantially isolated UCAM. In some embodiments, the fetal support tissue product is substantially isolated placenta. In some embodiments, the fetal support tissue product is substantially isolated umbilical cord. In some embodiments, the fetal support tissue product is substantially isolated chorion or amnion-chorion. In some embodiments, the fetal support tissue product is frozen or previously frozen PAM. In some embodiments, the fetal support tissue product is frozen or previously frozen UCAM. In some embodiments, the fetal support tissue product is frozen or previously frozen placenta. In some embodiments, the fetal support tissue product is frozen or previously frozen umbilical cord. In some embodiments, the fetal support tissue product is frozen or previously frozen chorion or amnion-chorion. In some embodiments, the fetal support tissue product does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*. In some embodiments, the fetal support tissue product is obtained from a human, non-primate human, cow or pig. In some embodiments, the fetal support tissue product is cryopreserved, lyophilized, terminally sterilized, or a combination thereof. In some embodiments, the fetal support tissue product is in the form of a pulverized powder or a homogenate.

In some embodiments, the methods comprise administering to an individual in need thereof a therapeutically-effective amount of a composition comprising substantially isolated HC-HA complex. In some embodiments, the substantially isolated HC-HA complex is isolated from amnion (PAM or UCAM), placenta, umbilical cord, or chorion. In some embodiments, the substantially isolated HC-HA complex is isolated from frozen or previously frozen placental amniotic membrane (PAM), frozen or previously frozen umbilical cord amniotic membrane (UCAM), frozen or previously frozen placenta, frozen or previously frozen umbilical cord, frozen or previously frozen chorion, frozen or previously frozen amnion-chorion, or any combinations thereof.

In some embodiments, the HC-HA complex is obtained by a process comprising: (a) providing a reaction mixture comprising: (i) HA (e.g., HMW HA); (ii) I$\alpha$I, wherein the I$\alpha$I is optionally in serum or isolated from serum; (iii) TSG-6, wherein the TSG-6 is optionally recombinant; and (iv) PTX3, wherein the PTX3 is optionally recombinant; wherein at least one of HA, I$\alpha$I, TSG-6, or PTX3 is optionally generated by a plurality of cells present in the reaction mixture; (b) incubating the reaction mixture for a period of time sufficient to produce HC-HA complex; and (c) isolating and purifying the HC-HA complex.

In some embodiments, the composition further comprises a pharmaceutically-acceptable diluents, excipient or carrier. In some embodiments, the composition is formulated as a solution, suspension, paste, ointment, oil, emulsion, microemulsion, cream, lotion, gel, or combination thereof. In some embodiments, the composition comprises substantially-isolated tissue product or HC-HA formulated into microspheres, microparticles, or liposomes. In some embodiments, the composition is formulated into PLGA copolymers. In some embodiments, the composition is formulated for controlled, sustained, or delayed release. In some embodiments, the composition is injected into an osteolytic joint. In some embodiments, the composition is administered by a patch. In some embodiments, the patch is placed on an osteolytic bone or an osteolytic joint. In some embodiments, the composition is administered by an implant. In some embodiments, the implant is placed on an osteolytic bone or an osteolytic joint. In some embodiments, the composition is formulated into an orthopaedic prosthesis. In some embodiments, the fetal support tissue product is in the form of a substantially-flattened sheet. In some embodiments, the composition further comprises a backing. In some embodiments, the composition is wrapped around an osteolytic bone or an osteolytic joint. In some embodiments, the methods further comprise administering to the individual a calcium supplement. In some embodiments, the methods further comprise administering to the individual a chemotherapeutic agent, a bisphosphinate, Metastron, or any combination thereof.

Fetal Support Tissue Products

Disclosed herein, in certain embodiments, are methods of inhibiting osteoclast differentiation in an individual in need thereof, comprising administering to the individual a composition comprising product fetal support tissue product or an extract thereof. Disclosed herein, in certain embodiments, are methods of promoting mineralization by osteoblasts in an individual in need thereof, comprising administering to the individual a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. Disclosed herein, in certain embodiments, are methods of inhibiting bone resorption in an individual in need thereof, comprising administering to the individual a composition comprising a fetal support tissue product or an extract thereof. Disclosed herein, in certain embodiments, are methods of inhibiting bone remodeling in an individual in need thereof, comprising administering to the individual a composition comprising a fetal support tissue product or an extract thereof. Disclosed herein, in certain embodiments, are methods of balancing bone resorption and bone formation, comprising administering to an individual in need thereof a therapeutically-effective amount of a composition comprising a fetal support tissue product or an extract thereof. Disclosed herein, in certain embodiments, are methods of treating a disease, disorder, or condition characterized by excessive or undesired osteoclast differentiation, the methods comprising administering to an individual in need thereof a therapeutically-effective amount of a composition comprising a fetal support tissue product or an extract thereof. Disclosed herein, in certain embodiments, are methods of treating a disease, disorder, or condition characterized by excessive or undesired bone absorption by osteoclasts, the methods comprising administering to an individual in need thereof a therapeutically-effective amount of a composition comprising a fetal support tissue product or an extract thereof. Disclosed herein, in certain embodiments, are methods of treating a disease, disorder, or condition characterized by deficient or defective bone formation, the methods comprising administering to an individual in need thereof a therapeutically-effective amount of a composition comprising a fetal support tissue product or an extract thereof. Disclosed herein, in certain embodiments, are methods of treating arthritis, the methods comprising administering to an individual in need thereof a therapeutically-effective amount of a composition comprising a fetal support tissue product or an extract thereof. Disclosed herein, in certain embodiments, are methods of treating osteoporosis, the methods comprising administering to an individual in need thereof a therapeutically-effective amount of a composition comprising a fetal support tissue product or an extract thereof. Disclosed herein, in certain embodiments, are methods of treating alveolar bone degradation, the methods comprising administering to an individual in need thereof a therapeutically-effective amount of a composition comprising a fetal support tissue product or an extract thereof. Disclosed herein, in certain embodiments, are methods of treating Paget's disease, the methods comprising administering to an individual in need thereof a therapeutically-effective amount of a composition comprising a fetal support tissue product or an extract thereof. Disclosed herein, in certain embodiments, are methods of treating a bone tumor, the methods comprising administering to an individual in need thereof a therapeutically-effective amount of a composition comprising a fetal support tissue product or an extract thereof. In some embodiments of any of the aforementioned methods, the fetal support tissue product is substantially isolated amnion. In some embodiments of any of the aforementioned methods, the fetal support tissue product is substantially isolated PAM. In some embodiments of any of the aforementioned methods, the fetal support tissue product is substantially isolated UCAM. In some embodiments of any of the aforementioned methods, the fetal support tissue product is substantially isolated placenta. In some embodiments of any of the aforementioned methods, the fetal support tissue product is substantially isolated umbilical cord. In some embodiments of any of the aforementioned methods, the fetal support tissue product is substantially isolated chorion or amnion-chorion. In some embodiments of any of the aforementioned methods, the fetal support tissue product is frozen or previously frozen PAM. In some embodiments of any of the aforementioned methods, the fetal support tissue product is frozen or previously frozen UCAM. In some embodiments of any of the aforementioned methods, the fetal support tissue product is frozen or previously frozen placenta. In some embodiments of any of the aforementioned methods, the fetal support tissue product is frozen or previously frozen umbilical cord. In some embodiments of any of the aforementioned methods, the fetal support tissue product is frozen or previously frozen chorion or amnion-chorion. In some embodiments of any of the aforementioned methods, the fetal support tissue product is in the form of a sheet, pulverized powder or a homogenate.

Umbilical Cord and UCAM

Umbilical cord is recovered from any suitable source (e.g., a hospital or tissue bank). Umbilical cord can be obtained from any mammal, such as a human, non-human primate, cow or pig.

The umbilical cord is kept frozen (e.g., at or below 0° C.) until donor and specimen eligibility has been determined. In some embodiments, freezing the umbilical cord kills substantially all cells found in the umbilical cord. In some embodiments, freezing the umbilical cord kills substantially all cells found in the umbilical cord while maintaining or increasing the biological activity of the umbilical cord relative to fresh (i.e., non-frozen) umbilical cord. In some embodiments, freezing the umbilical cord results in the loss of metabolic activity in substantially all cells found in the umbilical cord. In some embodiments, freezing the umbilical cord results in the loss of metabolic activity in substantially all cells found in the umbilical cord while maintaining or increasing the biological activity of the umbilical cord (e.g., its anti-inflammatory, anti-scarring, anti-antigenic, and anti-adhesion properties) relative to fresh (i.e., non-frozen) umbilical cord. In some embodiments, the umbilical cord is not frozen. If the umbilical cord is not frozen, it is processed as described below immediately. In some embodiments, the umbilical cord is dried (e.g., by lyophilization). In some embodiments, drying the umbilical cord kills substantially all cells found in the umbilical cord. In some embodiments, drying the umbilical cord results in the loss of metabolic activity in substantially all cells found in the umbilical cord.

All processing is done following Good Tissue Practices (GTP) to ensure that no contaminants are introduced into the UCAM products.

The umbilical cord is tested for HIV-1, HIV-2, HTLV-1, hepatitis B and C, West Nile virus, cytomegalovirus, human transmissible spongiform encephalopathy (e.g., Creutzfeldt-Jakob disease) and *Treponema pallidum* using FDA licensed screening test. Any indication that the tissue is contaminated with HIV-1, HIV-2, HTLV-1, hepatitis B and C, West Nile virus, or cytomegalovirus results in the immediate quarantine and subsequent destruction of the tissue specimen.

Further, the donor's medical records are examined for risk factors for and clinical evidence of hepatitis B, hepatitis C, or HIV infection. Any indication that the donor has risk factors for, and/or clinical evidence of, infection with HIV-1, HIV-2, HTLV-1, hepatitis B and C, West Nile virus, cytomegalovirus, human transmissible spongiform encephalopathy (e.g., Creutzfeldt-Jakob disease) and *Treponema pallidum* results in the immediate quarantine and subsequent destruction of the tissue specimen.

In some embodiments, substantially all of the blood is removed from the umbilical cord. In some embodiments, substantially all of the blood is removed from the umbilical cord before the umbilical cord is frozen. In some embodiments, blood is not removed from the UC. In some embodiments, blood is not removed from the umbilical cord before the umbilical cord is frozen.

In some embodiments, the umbilical cord tissue is washed with buffer with agitation to remove excess blood and tissue. In some embodiments, washing with agitation reduces the wash time. In some embodiments, the umbilical cord is contacted with an isotonic buffer. In some embodiments, the umbilical cord is contacted with saline, PBS, PBS 1X, Ringer's solution, Hartmann's solution, TRIS-buffered saline, HEPES-buffered saline, EBSS, HBSS, Tyrode's salt Solution, Gey's Balanced Salt Solution, DMEM, EMEM, GMEM, RPMI, or any combinations thereof.

In some embodiments, the umbilical cord is cut into multiple sheets. The size of the sheets depends on the desired use of the product derived from the umbilical cord.

In some embodiments, the section of the umbilical cord is not cut further. In some embodiments, the section of the umbilical cord is cut into smaller portions. Optionally, in some embodiments, additional cuts are made in the Wharton's Jelly to help shape the UC.

In some embodiments, the cut umbilical cord tissue is optionally washed again with buffer to further remove excess blood and tissue.

In some embodiments, part or all of the Wharton's Jelly is removed from the umbilical cord. The desired thickness of the fetal support tissue product determines how much, if any, of the Wharton's Jelly is removed. In some embodiments, the Wharton's Jelly is not removed.

The umbilical cord comprises two arteries (the umbilical arteries) and one vein (the umbilical vein). In some embodiments, the vein and arteries are removed from the umbilical cord. In certain instances, the vein and arteries are surrounded (or suspended or buried) within the Wharton's Jelly. In some embodiments, the vein and arteries are removed concurrently with the removal of the Wharton's Jelly. In some embodiments, the veins and arteries are not removed.

If a UCAM sheet is the desired fetal support tissue product, then generation of the UCAM sheet comprises substantially isolating the UCAM from the umbilical cord. After substantially pure UCAM has been obtained, the UCAM is optionally washed with buffer to remove excess blood and tissue.

In some embodiments, isolated UCAM is flattened following separation from the umbilical cord, generating a flat UCAM sheet comprising isolated UCAM. In some embodiments, the isolated UCAM is rolled following separation from the umbilical cord, generating a tubular UCAM sheet. In some embodiments, the UCAM sheets are in any suitable shape (e.g., a square, a circle, a triangle, a rectangle) and into any suitable size.

In some embodiments, the UCAM sheets are contacted with a buffer to remove substantially all remaining red blood cells. In some embodiments, the chorion or amnion-chorion sheets are contacted with an isotonic buffer. In some embodiments, the chorion or amnion-chorion sheets are contacted with saline, PBS, PBS 1X, Ringer's solution, Hartmann's solution, TRIS-buffered saline, HEPES-buffered saline, EBSS, HBSS, Tyrode's salt Solution, Gey's Balanced Salt Solution, DMEM, EMEM, GMEM, RPMI, or any combinations thereof.

In some embodiments, multiple layers of isolated UCAM are combined to generate a layered UCAM sheet. The layered UCAM sheet is any suitable thickness. In some embodiments, the layered UCAM sheet comprises two, three, four, five, six, seven, eight, nine, or ten layers of isolated UCAM. In some embodiments, the layered UCAM sheet comprises more than ten layers of isolated UCAM.

In some embodiments, the UCAM sheet is optionally contacted with a substrate (i.e., a supportive backing). In some embodiments, UCAM sheet is not contacted with a substrate. In some embodiments, the UCAM sheet does not require a particular orientation relative to the substrate (i.e., any side of the UCAM may be in contact with the substrate). In some embodiments, the UCAM sheet is orientated such that the epithelial layer is in contact with the substrate.

In some embodiments, the natural structural integrity of the umbilical cord (or, any isolated parts thereof, e.g., UCAM) is maintained in the sheet. In some embodiments, the natural biological activity of the umbilical cord (or, any isolated parts thereof, e.g., UCAM) is maintained in the sheet. In some embodiments, the natural structural integrity and the natural biological activity of the umbilical cord (or, any isolated parts thereof, e.g., UCAM) is maintained in the sheet.

In some embodiments, a powder or homogenate is made by: obtaining umbilical cord, processing the umbilical cord (see above for processing methods), and grinding (or pulverizing) or homogenizing the umbilical cord. In some embodiments, the powder or homogenate is made with whole umbilical cord. Optionally, the umbilical cord is further processed by removing Wharton's Jelly and/or the umbilical arteries and veins. Alternatively, the Wharton's Jelly and/or the umbilical arteries and veins are note removed. In some embodiments, the powder or homogenate is made by isolating the UCAM from the rest of the umbilical cord. In some embodiments, the natural biological activity of the umbilical cord (or, any isolated parts thereof) is substantially maintained.

In some embodiments, the powder or homogenate is prepared by any suitable method. In some embodiments, the powder or homogenate is prepared by use of a homogenizer (e.g., an ultrasonic homogenizer), sonicator, pulverizer, Warring blender, grinding mill/jar, bead beater, or any combination thereof.

In some embodiments, the powder or homogenate is prepared by use of a grinding jar. In some embodiments, the umbilical cord (or, any isolated parts thereof) is lyophilized prior to being placed in the grinding jar. A grinding ball is dropped in the grinding jar and the grinding jar is sealed. The grinding jar is immersed into liquid nitrogen for 5 min and then placed in a mill and ground at a 30 Hz grinding cycle for 4 min.

In some embodiments, the umbilical cord (or, any isolated parts thereof) is lyophilized by any suitable method (e.g., exposure to a liquid gas, placement in a freezer). In some embodiments, the umbilical cord (or, any isolated parts thereof) is placed in the vacuum chamber of a lyophilization device until all or substantially all fluid (e.g., water) has been removed. In some embodiments, the umbilical cord (or, any isolated parts thereof) is lyophilized following freezing (e.g., exposure to a temperature below 0° C., −20° C., −40° C., −50° C., −60° C., −70° C., −75° C., −80° C., −90° C., −100° C.).

In some embodiments, the natural biological activity of the umbilical cord (or, any isolated parts thereof) is maintained in the powder or homogenate.

In some embodiments, an extract is made from the umbilical cord or any isolated parts thereof. In some embodiments, the natural biological activity of the umbilical cord (or, any isolated parts thereof) is maintained in the extract. In some embodiments, a homogenate or powder is made as described above. In some embodiments, the homogenate or powder is centrifuged to generate an extract (i.e., a chorion extract or an amnion-chorion extract). Any suitable method of centrifugation may be used. In some embodiments, the extract comprises the supernatant. In some embodiments, the extract comprises the precipitant. In some embodiments, the extract is subject to additional extraction methods (e.g., HABP affinity chromatography, or immunoaffinity chromatography).

In some embodiments, the method of making the extract comprises: (a) mixing the homogenate or powder with cold PBS buffer without protease inhibitors, to generate a PBS mixture, (b) centrifuging the PBS mixture, and (c) isolating the extract, to generate an isolated extract. In some embodiments, the cold PBS buffer and tissue product are combined in a 1:1 ratio. In some embodiments, the PBS mixture is centrifuged at 48,000×g 4° C. for 30 min.

In some embodiments, the method of making the extract further comprises purifying the extract. The number of purification steps depends on the desired purity. In some embodiments, the purification comprises at least 2 rounds of ultracentrifugation. In some embodiments, the purification comprises more 2 rounds of ultracentrifugation. In some embodiments, the purification comprises at least 4 rounds of ultracentrifugation. In some embodiments, the method of purifying the isolated extract comprises: (d) dissolving the isolated extract in CsCl/4M guanidine HCl at the initial density of 1.35 g/ml, to generate a CsCl mixture, (e) centrifuging the CsCl mixture at 125,000×g for 48 h at 15° C., to generate a first purified extract, (f) extracting the first purified extract and dialyzing it against distilled water to remove CsCl and guanidine HCl, to generate a dialysate. In some embodiments, the method of purifying the isolated extract further comprises (g) mixing the dialysate with 3 volumes of 95% (v/v) ethanol containing 1.3% (w/v) potassium acetate at 0° C. for 1 h, to generate a first dialysate/ethanol mixture, (h) centrifuging the first dialysate/ethanol mixture at 15,000×g, to generate a second purified extract, and (i) extracting the second purified extract. In some embodiments, the method of purifying the isolated extract further comprises: (j) washing the second purified extract with ethanol (e.g., 70% ethanol), to generate a second purified extract/ethanol mixture; (k) centrifuging the second purified extract/ethanol mixture, to generate a third purified extract; and (l) extracting the third purified extract. In some embodiments, the method of purifying the isolated extract further comprises: (m) washing the third purified extract with ethanol (e.g., 70% ethanol), to generate a third purified extract/ethanol mixture; (n) centrifuging the third purified extract/ethanol mixture, to generate a forth purified extract; and (o) extracting the forth purified extract. In some embodiments, the purified extract comprises HC-HA complex.

Placenta and Placental Amniotic Membrane (PAM)

Placenta is recovered from any suitable source (e.g., a hospital or tissue bank). Placenta can be obtained from any mammal, such as a human, non-human primate, cow or pig. The placenta may be frozen, previously frozen, or fresh (i.e., not frozen).

Where the placenta is not processed into a pulverized immediately after it has been obtained, it is processed for storage (e.g., it is frozen or dried). In some embodiments, the placenta is frozen for storage. In some embodiments, the placenta is frozen at or below 0° C. In some embodiments, the placenta is frozen until donor and specimen eligibility has been determined. In some embodiments, the placenta is placed in a cryo-preservative before being frozen. In some embodiments, freezing the placenta kills substantially all cells found in the placenta. In some embodiments, freezing the placenta kills substantially all cells found in the placenta while maintaining or increasing the biological activity of the placenta relative to fresh (i.e., non-frozen) placenta. In some embodiments, freezing the placenta results in the loss of metabolic activity in substantially all cells found in the placenta. In some embodiments, freezing the placenta results in the loss of metabolic activity in substantially all cells found in the placenta while maintaining or increasing the biological activity of the placenta relative to fresh (i.e., non-frozen) placenta. If the placenta is not frozen, it is processed as described below immediately. In some embodiments, the placenta is dried (e.g., by lyophilization). In some embodiments, drying the placenta kills substantially all cells found in the placenta. In some embodiments, drying the placenta results in the loss of metabolic activity in substantially all cells found in the placenta.

All processing is done following Good Tissue Practices (GTP) to ensure that no contaminants are introduced into the tissue grafts or PAM.

The placenta is tested for HIV-1, HIV-2, HTLV-1, hepatitis B and C, West Nile virus, cytomegalovirus, human transmissible spongiform encephalopathy (e.g., Creutzfeldt-Jakob disease) and *Treponema pallidum* using FDA licensed screening test. Any indication that the tissue is contaminated with HIV-1, HIV-2, HTLV-1, hepatitis B and C, West Nile virus, or cytomegalovirus results in the immediate quarantine and subsequent destruction of the tissue specimen.

Further, the donor's medical records are examined for risk factors for and clinical evidence of hepatitis B, hepatitis C, or HIV infection. Any indication that the donor has risk factors for, and/or clinical evidence of, infection with HIV-1, HIV-2, HTLV-1, hepatitis B and C, West Nile virus, cytomegalovirus, human transmissible spongiform encephalopathy (e.g., Creutzfeldt-Jakob disease) and *Treponema pallidum* results in the immediate quarantine and subsequent destruction of the tissue specimen.

In some embodiments, the PAM is not isolated from the placenta before further processing begins. In some embodiments, the PAM is isolated from the placenta (generating isolated PAM) before further processing begins, In some embodiments, substantially all of the blood is removed from the placenta. In some embodiments, some blood is removed from placenta. In some embodiments, the blood is not removed from the placenta.

In some embodiments, the placenta is washed with buffer with agitation to remove excess blood and tissue. In some embodiments, washing with agitation reduces the wash time.

In some embodiments, the placenta is contacted with a buffer. In some embodiments, the placenta is contacted with an isotonic buffer. In some embodiments, the placenta is contacted with saline, PBS, PBS 1X, Ringer's solution, Hartmann's solution, TRIS-buffered saline, HEPES-buffered saline, EBSS, HBSS, Tyrode's salt Solution, Gey's Balanced Salt Solution, DMEM, EMEM, GMEM, RPMI, or any combinations thereof.

In some embodiments, the placenta is washed with an isotonic buffer or tissue culture media, and any suitable antibiotic. In some embodiments, the antibiotic is ciprofloxacin, amphotericin B, penicillin, streptomycin, neomycin or a combination thereof. In some embodiments, the antibiotic is ciprofloxacin and amphotericin B. In some embodiments, the antibiotic is penicillin, streptomycin, neomycin, and amphotericin B.

In some embodiments, the placenta is cut into multiple sections (e.g., using a scalpel). The size of the sections depends on the desired use of the product derived from the placenta.

In some embodiments, the cut placenta tissue is optionally washed again with buffer to further remove excess blood and tissue.

If a PAM sheet is the desired fetal support tissue product, then generation of the PAM sheet comprises any or all of the following steps in addition to the preceding steps.

In some embodiments, PAM is substantially isolated from the placenta. After substantially isolated PAM has been obtained, the PAM is optionally washed with buffer to remove excess blood and tissue.

In some embodiments, isolated PAM is cut into in any suitable shape (e.g., a square, a circle, a triangle, a rectangle) and into any suitable sizes.

In some embodiments, the PAM sheets are contacted with a buffer to remove substantially all remaining red blood cells. In some embodiments, the chorion or amnion-chorion sheets are contacted with an isotonic buffer. In some embodiments, the chorion or amnion-chorion sheets are contacted with saline, PBS, PBS1×, Ringer's solution, Hartmann's solution, TRIS-buffered saline, HEPES-buffered saline, EBSS, HBSS, Tyrode's salt Solution, Gey's Balanced Salt Solution, DMEM, EMEM, GMEM, RPMI, or any combinations thereof.

In some embodiments, multiple layers of isolated PAM are combined to generate a layered PAM sheet. The layered PAM sheet is any suitable thickness. In some embodiments, the layered PAM sheet comprises two, three, four, five, six, seven, eight, nine, or ten layers of isolated PAM. In some embodiments, the layered PAM sheet comprises more than ten layers of isolated PAM.

In some embodiments, the PAM sheet is optionally contacted with a substrate (i.e., a supportive backing). In some embodiments, PAM sheet is not contacted with a substrate. In some embodiments, the PAM sheet does not require a particular orientation relative to the substrate (i.e., any side of the PAM may be in contact with the substrate). In some embodiments, the PAM sheet is orientated such that the epithelial layer is in contact with the substrate.

In some embodiments, the natural structural integrity of the placenta (or any isolated parts thereof; e.g., PAM) is maintained in the sheet. In some embodiments, the natural biological activity of the placenta (or any isolated parts thereof) is maintained in the sheet. In some embodiments, the natural structural integrity and natural biological activity of the placenta (or any isolated parts thereof; e.g., PAM) is maintained in the sheet.

In some embodiments, a powder or homogenate is made by: obtaining placenta, processing the placenta (see above for processing methods), and grinding (or pulverizing) or homogenizing the placenta. In some embodiments, the powder or homogenate is made with whole placenta. In some embodiments, the powder or homogenate is made by isolating the PAM from the rest of the placenta. In some embodiments, the natural biological activity of the placenta (or, any isolated parts thereof) is substantially maintained.

In some embodiments, the powder or homogenate is prepared by any suitable method. In some embodiments, the powder or homogenate is prepared by use of a homogenizer (e.g., an ultrasonic homogenizer), sonicator, pulverizer, Warring blender, grinding mill/jar, bead beater, or any combination thereof.

In some embodiments, the powder or homogenate is prepared by use of a grinding jar. In some embodiments, the placenta (or, any isolated parts thereof) is lyophilized prior to being placed in the grinding jar. A grinding ball is dropped in the grinding jar and the grinding jar is sealed. The grinding jar is immersed into liquid nitrogen for 5 min and then placed in a mill and ground at a 30 Hz grinding cycle for 4 min.

In some embodiments, the placenta (or, any isolated parts thereof) is lyophilized by any suitable method (e.g., exposure to a liquid gas, placement in a freezer). In some embodiments, the placenta (or, any isolated parts thereof) is placed in the vacuum chamber of a lyophilization device until all or substantially all fluid (e.g., water) has been removed. In some embodiments, the placenta (or, any isolated parts thereof) is lyophilized following freezing (e.g., exposure to a temperature below 0° C., −20° C., −40° C., −50° C., −60° C., −70° C., −75° C., −80° C., −90° C., −100° C.).

In some embodiments, the natural biological activity of the placenta or any isolated parts thereof is maintained in a powder or homogenate.

In some embodiments, an extract is made from the placenta or any isolated parts thereof. In some embodiments, the natural biological activity of the placenta or any isolated parts thereof is maintained in an extract. In some embodiments, a homogenate or powder is made as described above. In some embodiments, the homogenate or powder is centrifuged to generate an extract (i.e., a chorion extract or an amnion-chorion extract). Any suitable method of centrifugation may be used. In some embodiments, the extract comprises the supernatant. In some embodiments, the extract comprises the precipitant. In some embodiments, the extract is subject to additional extraction methods (e.g., HABP affinity chromatography, or immunoaffinity chromatography).

In some embodiments, the method of making the extract comprises: (a) mixing the homogenate or powder with cold PBS buffer without protease inhibitors, to generate a PBS mixture, (b) centrifuging the PBS mixture, and (c) isolating the extract, to generate an isolated extract. In some embodiments, the cold PBS buffer and tissue product are combined in a 1:1 ratio. In some embodiments, the PBS mixture is centrifuged at 48,000×g 4° C. for 30 min.

In some embodiments, the method of making the extract further comprises purifying the extract. The number of purification steps depends on the desired purity. In some embodiments, the purification comprises at least 2 rounds of ultracentrifugation. In some embodiments, the purification comprises more 2 rounds of ultracentrifugation. In some embodiments, the purification comprises at least 4 rounds of ultracentrifugation. In some embodiments, the method of purifying the isolated extract comprises: (d) dissolving the isolated extract in CsCl/4M guanidine HCl at the initial density of 1.35 g/ml, to generate a CsCl mixture, (e) centrifuging the CsCl mixture at 125,000×g for 48 h at 15° C., to generate a first purified extract, (f) extracting the first purified extract and dialyzing it against distilled water to remove CsCl and guanidine HCl, to generate a dialysate. In some embodiments, the method of purifying the isolated extract further comprises (g) mixing the dialysate with 3 volumes of 95% (v/v) ethanol containing 1.3% (w/v) potassium acetate at 0° C. for 1 h, to generate a first dialysate/ethanol mixture, (h) centrifuging the first dialysate/ethanol mixture at 15,000×g, to generate a second purified extract, and (i) extracting the second purified extract. In some embodiments, the method of purifying the isolated extract further comprises: (j) washing the second purified extract with ethanol (e.g., 70% ethanol), to generate a second purified extract/ethanol mixture; (k) centrifuging the second purified extract/ethanol mixture, to generate a third purified extract; and (l) extracting the third purified extract. In some embodiments, the method of purifying the isolated extract further comprises: (m) washing the third purified extract with ethanol (e.g., 70% ethanol), to generate a third purified extract/ethanol mixture; (n) centrifuging the third purified extract/ethanol mixture, to generate a forth purified extract; and (o) extracting the forth purified extract. In some embodiments, the purified extract comprises HC-HA complex.

Chorion and Amnion-Chorion

Placenta comprising chorion is recovered from any suitable source (e.g., a hospital or tissue bank). Placenta can be obtained from any mammal, such as a human, non-human primate, cow or pig. The placenta may be frozen, previously frozen, or fresh (i.e., not frozen).

In some embodiments, the chorion is immediately isolated from the placenta. In some embodiments, the chorion is not immediately isolated from the placenta. In some embodiments, the chorion or amnion-chorion (or, placenta comprising chorion) is frozen for storage. In some embodiments, the chorion or amnion-chorion (or, placenta comprising chorion) is frozen at or below 0° C. In some embodiments, the chorion or amnion-chorion (or, placenta comprising chorion) is frozen until donor and specimen eligibility has been determined. In some embodiments, the chorion or amnion-chorion (or, placenta comprising chorion) is placed in a cryo-preservative before being frozen. In some embodiments, freezing the chorion or amnion-chorion (or, placenta comprising chorion) kills substantially all cells found in the chorion or amnion-chorion. In some embodiments, freezing the chorion or amnion-chorion (or, placenta comprising chorion) kills substantially all cells found in the chorion or amnion-chorion while maintaining or increasing the biological activity of the chorion or amnion-chorion relative to fresh (i.e., non-frozen) chorion or amnion-chorion. In some embodiments, freezing the chorion or amnion-chorion (or, placenta comprising chorion) results in the loss of metabolic activity in substantially all cells found in the chorion or amnion-chorion. In some embodiments, freezing the chorion or amnion-chorion (or, placenta comprising chorion) results in the loss of metabolic activity in substantially all cells found in the chorion or amnion-chorion while maintaining or increasing the biological activity of the chorion or amnion-chorion relative to fresh (i.e., non-frozen) chorion or amnion-chorion. If the chorion or amnion-chorion is not frozen, it is processed as described below immediately. In some embodiments, the chorion or amnion-chorion (or, placenta comprising chorion) is dried (e.g., by lyophilization). In some embodiments, drying the chorion or amnion-chorion (or, placenta comprising chorion) kills substantially all cells found in the chorion or amnion-chorion. In some embodiments, drying the chorion or amnion-chorion (or, placenta comprising chorion) results in the loss of metabolic activity in substantially all cells found in the chorion or amnion-chorion.

All processing is done following Good Tissue Practices (GTP) to ensure that no contaminants are introduced into the tissue grafts or PAM.

The chorion or amnion-chorion (or, placenta comprising chorion) is tested for HIV-1, HIV-2, HTLV-1, hepatitis B and C, West Nile virus, cytomegalovirus, human transmissible spongiform encephalopathy (e.g., Creutzfeldt-Jakob disease) and *Treponema pallidum* using FDA licensed screening test. Any indication that the tissue is contaminated with HIV-1, HIV-2, HTLV-1, hepatitis B and C, West Nile virus, or cytomegalovirus results in the immediate quarantine and subsequent destruction of the tissue specimen.

Further, the donor's medical records are examined for risk factors for and clinical evidence of hepatitis B, hepatitis C, or HIV infection. Any indication that the donor has risk factors for, and/or clinical evidence of, infection with HIV-1, HIV-2, HTLV-1, hepatitis B and C, West Nile virus, cytomegalovirus, human transmissible spongiform encephalopathy (e.g., Creutzfeldt-Jakob disease) and *Treponema pallidum* results in the immediate quarantine and subsequent destruction of the tissue specimen.

In some embodiments, the chorion or amnion-chorion is not isolated from the placenta before further processing begins. In some embodiments, the chorion or amnion-chorion is isolated from the placenta before further processing begins.

In some embodiments, substantially all of the blood is removed from the placenta, chorion, or amnion-chorion. In some embodiments, some blood is removed from the placenta, chorion, or amnion-chorion. In some embodiments, the blood is not removed from the placenta, chorion, or amnion-chorion.

In some embodiments, the placenta, chorion, or amnion-chorion is contacted with a buffer. In some embodiments, the placenta, chorion, or amnion-chorion is contacted with an isotonic buffer. In some embodiments, the placenta, chorion, or amnion-chorion is contacted with saline, PBS, PBS1×, Ringer's solution, Hartmann's solution, TRIS-buffered saline, HEPES-buffered saline, EBSS, HBSS, Tyrode's salt Solution, Gey's Balanced Salt Solution, DMEM, EMEM, GMEM, RPMI, or any combinations thereof.

In some embodiments, the placenta, chorion, or amnion-chorion is contacted with a suitable antibiotic. In some embodiments, the antibiotic is ciprofloxacin, amphotericin B, penicillin, streptomycin, neomycin or a combination thereof. In some embodiments, the antibiotic is ciprofloxacin and amphotericin B. In some embodiments, the antibiotic is penicillin, streptomycin, neomycin, and amphotericin B.

In some embodiments, the chorion or amnion-chorion is cut into multiple sheets (e.g., using a scalpel). The size of the sheets depends on the desired use of the product derived from the chorion or amnion-chorion. In some embodiments, chorion or amnion-chorion is cut into in any suitable shape (e.g., a square, a circle, a triangle, a rectangle) and into any suitable sizes.

In some embodiments, the chorion or amnion-chorion sheet is contacted with a buffer to remove substantially all remaining red blood cells. In some embodiments, the chorion or amnion-chorion sheet is contacted with an isotonic buffer. In some embodiments, the chorion or amnion-chorion sheet is contacted with saline, PBS, PBS1×, Ringer's solution, Hartmann's solution, TRIS-buffered saline, HEPES-buffered saline, EBSS, HBSS, Tyrode's salt Solution, Gey's Balanced Salt Solution, DMEM, EMEM, GMEM, RPMI, or any combinations thereof.

In some embodiments, multiple layers of isolated chorion or amnion-chorion are combined to generate a layered chorion or amnion-chorion sheet. In some embodiments, a layered chorion or amnion-chorion sheet comprises at least one layer of chorion and at least one layer of amnion. The layered chorion or amnion-chorion sheet is any suitable thickness. In some embodiments, the layered chorion or amnion-chorion sheet comprises two, three, four, five, six, seven, eight, nine, or ten layers of isolated chorion or amnion-chorion. In some embodiments, the layered chorion or amnion-chorion sheet comprises more than ten layers of isolated chorion or amnion-chorion.

In some embodiments, the chorion or amnion-chorion sheet is optionally contacted with a substrate (i.e., a supportive backing). In some embodiments, chorion or amnion-chorion sheet is not contacted with a substrate. In some embodiments, the chorion or amnion-chorion sheet does not require a particular orientation relative to the substrate (i.e., any side of the chorion or amnion-chorion may be in contact with the substrate). In some embodiments, the chorion or amnion-chorion sheet is orientated such that the epithelial layer is in contact with the substrate.

In some embodiments, the natural structural integrity of the chorion or amnion-chorion is maintained in the sheet. In some embodiments, the natural biological activity of the chorion or amnion-chorion is maintained in the sheet. In some embodiments, the natural structural integrity and the natural biological activity of the chorion or amnion-chorion is maintained in the sheet.

In some embodiments, a powder or homogenate is made by: obtaining placenta comprising chorion, processing the placenta and isolating the chorion (see above for processing and isolation methods), and grinding (or pulverizing) or homogenizing the chorion or amnion-chorion. In some embodiments, the powder or homogenate is made with chorion. In some embodiments, the powder or homogenate is made with amnion-chorion. In some embodiments, the natural biological activity of the chorion or chorion-amnion (or, any isolated parts thereof) is substantially maintained.

In some embodiments, the powder or homogenate is prepared by any suitable method. In some embodiments, the powder or homogenate is prepared by use of a homogenizer (e.g., an ultrasonic homogenizer), sonicator, pulverizer, Warring blender, grinding mill/jar, bead beater, or any combination thereof.

In some embodiments, the powder or homogenate is prepared by use of a grinding jar. In some embodiments, the chorion or amnion-chorion is lyophilized prior to being placed in the grinding jar. A grinding ball is dropped in the grinding jar and the grinding jar is sealed. The grinding jar is immersed into liquid nitrogen for 5 min and then placed in a mill and ground at a 30 Hz grinding cycle for 4 min.

In some embodiments, the chorion or amnion-chorion is lyophilized by any suitable method (e.g., exposure to a liquid gas, placement in a freezer). In some embodiments, the chorion or amnion-chorion (or, any isolated parts thereof) is placed in the vacuum chamber of a lyophilization device until all or substantially all fluid (e.g., water) has been removed. In some embodiments, the placenta (or, any isolated parts thereof) is lyophilized following freezing (e.g., exposure to a temperature below 0° C., −20° C., −40° C., −50° C., −60° C., −70° C., −75° C., −80° C., −90° C., −100° C.).

In some embodiments, the natural biological activity of the chorion or amnion-chorion is maintained in the powder or homogenate.

In some embodiments, an extract is made from the chorion or amnion-chorion. In some embodiments, the natural biological activity of the chorion or amnion-chorion is maintained in the extract. In some embodiments, a homogenate or powder is made as described above. In some embodiments, the homogenate or powder is centrifuged to generate an extract. Any suitable method of centrifugation may be used. In some embodiments, the extract comprises the supernatant. In some embodiments, the extract comprises the precipitant. In some embodiments, the extract is subject to additional extraction methods (e.g., HABP affinity chromatography, or immunoaffinity chromatography).

In some embodiments, the method of making the extract comprises: (a) mixing the homogenate or powder with cold PBS buffer without protease inhibitors, to generate a PBS mixture, (b) centrifuging the PBS mixture, and (c) isolating the extract, to generate an isolated extract. In some embodiments, the cold PBS buffer and tissue product are combined in a 1:1 ratio. In some embodiments, the PBS mixture is centrifuged at 48,000×g 4° C. for 30 min.

In some embodiments, the method of making the extract further comprises purifying the extract. The number of purification steps depends on the desired purity. In some embodiments, the purification comprises at least 2 rounds of ultracentrifugation. In some embodiments, the purification comprises more 2 rounds of ultracentrifugation. In some embodiments, the purification comprises at least 4 rounds of ultracentrifugation. In some embodiments, the method of purifying the isolated extract comprises: (d) dissolving the isolated extract in CsCl/4M guanidine HCl at the initial density of 1.35 g/ml, to generate a CsCl mixture, (e) centrifuging the CsCl mixture at 125,000×g for 48 h at 15° C., to generate a first purified extract, (f) extracting the first purified extract and dialyzing it against distilled water to remove CsCl and guanidine HCl, to generate a dialysate. In some embodiments, the method of purifying the isolated extract further comprises (g) mixing the dialysate with 3 volumes of 95% (v/v) ethanol containing 1.3% (w/v) potassium acetate at 0° C. for 1 h, to generate a first dialysate/ethanol mixture, (h) centrifuging the first dialysate/ethanol mixture at 15,000×g, to generate a second purified extract, and (i) extracting the second purified extract. In some embodiments, the method of purifying the isolated extract further comprises: (j) washing the second purified extract with ethanol (e.g., 70% ethanol), to generate a second purified extract/ethanol mixture; (k) centrifuging the second purified extract/ethanol mixture, to generate a third purified extract; and (l) extracting the third purified extract. In some embodiments, the method of purifying the isolated extract further comprises: (m) washing the third purified extract with ethanol (e.g., 70% ethanol), to generate a third purified extract/ethanol mixture; (n) centrifuging the third purified extract/ethanol mixture, to generate a forth purified extract; and (o) extracting the forth purified extract. In some embodiments, the purified extract comprises HC-HA complex.

Storage

In some embodiments, a fetal support tissue product described herein is stored for later use. In some embodiments, storing a fetal support tissue product described herein does not destroy the natural biological activity of the fetal support tissue product. In some embodiments, storing a fetal support tissue product described herein does not destroy the natural structural integrity of the fetal support tissue product.

Sterilization

In some embodiments, a fetal support tissue product described herein is subject to terminal sterilization by any suitable (e.g., medically acceptable) method. In some embodiments, a fetal support tissue product described herein is exposed to gamma radiation for a period of time sufficient to sterilize the fetal support tissue product. In some embodiments, a fetal support tissue product described herein is exposed to gamma radiation at 25 kGy for a period of time sufficient to sterilize the fetal support tissue product. In some embodiments, a fetal support tissue product described herein is exposed to gamma radiation at 17-30 kGy for a period of time sufficient to sterilize the fetal support tissue product. In some embodiments, a fetal support tissue product described herein is exposed to an electron beam for a period of time sufficient to sterilize the fetal support tissue product. In some embodiments, a fetal support tissue product described herein is exposed to X-ray radiation for a period of time sufficient to sterilize the fetal support tissue product. In some embodiments, a fetal support tissue product described herein is exposed to UV radiation for a period of time sufficient to sterilize the fetal support tissue product.

In some embodiments, the dose range of the gamma-radiation is between 10 kGy and 60 kGy, e.g., between 17 kGy and 30 kGy, between 17 kGy and 20 kGy, between 20 kGy and 24 kGy, 25 kGy and 30 kGy. In some embodiments, the placental product is radioprotected by exposure to a radioprotectant. In some embodiments, the radioprotectant comprises glycerol, propylene glycol, trehalose, manitol, DMSO, or a combination thereof.

In some embodiments, a fetal support tissue product described herein is placed in a suitable radio-protectant. In some embodiments, the radio-protectant comprises Glycerol, Propylene Glycol, DMSO, Trehalose, Mannitol, or a combination thereof. In some embodiments, the radio-protectant comprises Glycerol, Propylene Glycol, or a combination thereof.

Storage Medium

In some embodiments, the fetal support tissue product is stored in any suitable storage medium. In some embodiments, the storage medium is DMEM, Liebowitz's medium, MEM, NCTC, or any combination thereof.

In some embodiments, the storage medium comprises a high oncotic or hyperosmotic agent (also referred to as a "plasma expander"). In some embodiments, the hyperosmotic agent is propylene glycol, glycerol; sugars, such as glucose, sucrose, maltose, dextrose, and the like; dimethyl sulfoxide (DMSO); dimethylamine (DMA); polyvinylpyrrolidone (PVP); sorbitol, glutathione (GSH); ascorbic acid; rosmarinic acid (RO); riboflavin; dextran; albumin; trehalose; mannitol; or any combination thereof. The hyperosmotic agent maintains an optimal hydration state of the fetal support tissue product. Preferably, the hydration of the fetal support tissue product is maintained between about 60% and 90% hydration for the intended purpose. In some embodiments, the hyperosmotic agent makes up about 10% to 90% of the storage medium, preferably 10% to about 50%, and more preferably about 30% to about 50%. In some embodiments, the fetal support tissue product is stored in 10%, 20%, 30%, 40%, 50%, 60%, 70%, 80%, 90% or 100% glycerol. In some embodiments, the fetal support tissue product is stored in 10%, 20%, 30%, 40%, 50%, 60%, 70%, 80%, 90% or 100% propylene glycol.

In some embodiments, the fetal support tissue product is stored in 50% DMEM+50% Glycerol.

Cryopreservation

In some embodiments, a fetal support tissue product described herein is frozen for cryopreservation by any suitable method (e.g., exposure to a liquid gas, placement in a freezer, graduated cryopreservation). In some embodiments, cryopreserving a fetal support tissue product described herein does not destroy the natural biological activity of the fetal support tissue product. In some embodiments, cryopreserving a fetal support tissue product described herein does not destroy the natural structural integrity of the fetal support tissue product.

In some embodiments, a fetal support tissue product described herein is exposed to a liquid gas (e.g., liquid nitrogen or liquid hydrogen). In some embodiments, the tissue product disclosed herein is exposed to liquid nitrogen. In some embodiments, the fetal support tissue product disclosed herein does not contact the liquid gas. In some embodiments, the fetal support tissue product disclosed herein is placed in a container and the container is contacted with liquid gas. In some embodiments, the fetal support tissue product is exposed to the liquid gas until the fetal support tissue product is frozen.

In some embodiments, the fetal support tissue product disclosed herein is frozen by exposure to a temperature below about 0° C. In some embodiments, a fetal support tissue product described herein is frozen by exposure to a liquid gas.

In some embodiments, the fetal support tissue product disclosed herein is frozen by graduated cryopreservation (e.g., by lowering down the temperature in a computer-generated program).

In some embodiments, a fetal support tissue product described herein is placed in a suitable cryo-preservative. In some embodiments, the cryo-preservative comprises Glycerol, Propylene Glycol, DMSO, Trehalose, Mannitol, or a combination thereof. In some embodiments, the cryo-preservative comprises Glycerol, Propylene Glycol, or a combination.

Lyophilization

In some embodiments, the fetal support tissue product disclosed herein is lyophilized. In some embodiments, lyophilizing a fetal support tissue product described herein does not destroy the natural biological activity of the fetal support tissue product. In some embodiments, lyophilizing a fetal support tissue product described herein does not destroy the natural structural integrity of the fetal support tissue product.

In some embodiments, the fetal support tissue product disclosed herein is lyophilized following freezing. In some embodiments, the fetal support tissue product disclosed herein is lyophilized following freezing by any suitable method (e.g., exposure to a liquid gas, placement in a freezer).

In some embodiments, a frozen tissue product disclosed herein is placed in the vacuum chamber of a lyophilization device until all or substantially all fluid (e.g., water) has been removed.

Rehydration

In some embodiments, a dehydrated or lyophilized product tissue product disclosed herein is partially or fully rehydrated. In some embodiments, dehydrated or lyophilized product tissue product disclosed herein rehydrated by contacting the fetal support tissue product with a buffer or with water. In some embodiments, the fetal support tissue product is contacted with an isotonic buffer. In some embodiments, the fetal support tissue product is contacted with saline. In some embodiments, the fetal support tissue product is contacted with PBS. In some embodiments, the fetal support tissue product is contacted with Ringer's solution. In some embodiments, the fetal support tissue product is contacted with Hartmann's solution. In some embodiments, the fetal support tissue product is contacted with a TRIS-buffered saline. In some embodiments, the fetal support tissue product is contacted with a HEPES-buffered saline; 50% DMEM+50% Glycerol; 10%, 20%, 30%, 40%, 50%, 60%, 70%, 80%, 90% or 100% glycerol; and/or 10%, 20%, 30%, 40%, 50%, 60%, 70%, 80%, 90% or 100% propylene glycol.

HC-HA Complex

Disclosed herein, in certain embodiments, are methods of inhibiting osteoclast differentiation in an individual in need thereof, comprising administering to the individual a composition comprising HC-HA complex. Disclosed herein, in certain embodiments, are methods of promoting mineralization by osteoblasts in an individual in need thereof, comprising administering to the individual a composition comprising HC-HA complex. Disclosed herein, in certain embodiments, are methods of inhibiting bone resorption in an individual in need thereof, comprising administering to the individual a composition comprising HC-HA complex. Disclosed herein, in certain embodiments, are methods of inhibiting bone remodeling in an individual in need thereof, comprising administering to the individual a composition comprising HC-HA complex. Disclosed herein, in certain embodiments, are methods of balancing bone resorption and bone formation, comprising administering to an individual in need thereof a therapeutically-effective amount of a composition comprising HC-HA complex. Disclosed herein, in certain embodiments, are methods of treating a disease, disorder, or condition characterized by excessive or undesired osteoclast differentiation, the methods comprising administering to an individual in need thereof a therapeutically-effective amount of a composition comprising HC-HA complex. Disclosed herein, in certain embodiments, are methods of treating a disease, disorder, or condition characterized by excessive or undesired bone absorption by osteoclasts, the methods comprising administering to an individual in need thereof a therapeutically-effective amount of a composition comprising HC-HA complex. Disclosed herein, in certain embodiments, are methods of treating a disease, disorder, or condition characterized by deficient or defective bone formation, the methods comprising administering to an individual in need thereof a therapeutically-effective amount of a composition comprising HC-HA complex. Disclosed herein, in certain embodiments, are methods of treating arthritis, the methods comprising administering to an individual in need thereof a therapeutically-effective amount of a composition comprising HC-HA complex. Disclosed herein, in certain embodiments, are methods of treating osteoporosis, the methods comprising administering to an individual in need thereof a therapeutically-effective amount of a composition comprising HC-HA complex. Disclosed herein, in certain embodiments, are methods of treating alveolar bone degradation, the methods comprising administering to an individual in need thereof a therapeutically-effective amount of a composition comprising HC-HA complex. Disclosed herein, in certain embodiments, are methods of treating Paget's disease, the methods comprising administering to an individual in need thereof a therapeutically-effective amount of a composition comprising HC-HA complex. Disclosed herein, in certain embodiments, are methods of treating a bone tumor, the methods comprising administering to an individual in need thereof a therapeutically-effective amount of a composition comprising HC-HA complex. In some embodiments of any of the aforementioned methods, the HC-HA complex is isolated from a fetal support tissue (e.g., UCAM, PAM, umbilical cord, placenta, chorion, amnion-chorion, or any combinations thereof) and purified. In some embodiments of any of the aforementioned methods, the HC-HA complex is obtained by a process comprising (a) providing a reaction mixture comprising: (i) HA (e.g., HMW HA); (ii) I$\alpha$I, wherein the I$\alpha$I is optionally in serum or isolated from serum; (iii); (iii) TSG-6, wherein the TSG-6 is optionally recombinant; and (iv) PTX3, wherein the PTX3 is optionally recombinant; wherein at least one of HA, I$\alpha$I, TSG-6, or PTX3 is optionally generated by a plurality of cells present in the reaction mixture; (b) incubating the reaction mixture for a period of time sufficient to produce HC-HA complex; and (c) isolating and purifying the HC-HA complex.

Manufacturing HC-HA

In some embodiments of any of the aforementioned methods, the HC-HA complex is obtained by a process comprising (a) providing a reaction mixture comprising: (i) HA (e.g., HMW HA); (ii) I$\alpha$I, wherein the I$\alpha$I is optionally in serum or isolated from serum; (iii); (iii) TSG-6, wherein the TSG-6 is optionally recombinant; and (iv) PTX3, wherein the PTX3 is optionally recombinant; wherein at least one of HA, I$\alpha$I, TSG-6, or PTX3 is optionally generated by a plurality of cells present in the reaction mixture; (b) incubating the reaction mixture for a period of time sufficient to produce HC-HA complex; and (c) isolating and purifying the HC-HA complex. In some embodiments, the contacting occurs for at least 6 hours, at least 12 hours, at least 24 hours, at least 36 hours, at least 48 hours, at least 60 hours, or at least 72 hours.

In some embodiments, the method further comprises immobilizing HA (e.g., HMW HA) to a stationary support (e.g., by cross-linking). In some embodiments, the stationary support comprising HA (e.g., HMW HA) is contacted with I$\alpha$I (e.g., I$\alpha$I purified from serum, I$\alpha$I in serum), TSG-6 (or, recombinant TSG-6), and PTX3 (or, recombinant PTX3). In some embodiments, the contacting occurs for at least 6 hours, at least 12 hours, at least 24 hours, at least 36 hours, at least 48 hours, at least 60 hours, or at least 72 hours. In some embodiments, the stationary support is washed to remove any unbound components.

In some embodiments, the method further comprises HA binding protein (HABP). In some embodiments, HABP is affixed to a stationary support (e.g., by cross-linking). In some embodiments, the stationary support comprising HABP is contacted with HA (e.g., HMW HA), I$\alpha$I, TSG-6 (or, recombinant TSG-6), and PTX3 (or, recombinant PTX3). In some embodiments, the contacting occurs for at least 6 hours, at least 12 hours, at least 24 hours, at least 36 hours, at least 48 hours, at least 60 hours, or at least 72 hours. In some embodiments, the stationary support is washed to remove any unbound components.

In some embodiments, I$\alpha$I is isolated from serum. In some embodiments, I$\alpha$I is in serum. In some embodiments, I$\alpha$I is isolated from a cell or plurality of cells.

In some embodiments, TSG6 is isolated from a cell or a plurality of cells (e.g., a tissue extract). In some embodiments, TSG6 is not isolated from a cell or a plurality of cells (e.g., a tissue extract). In some embodiments, TSG6 is prepared by recombinant technology.

In some embodiments, PTX3 is isolated from a cell or a plurality of cells (e.g., a tissue extract). In some embodiments, PTX3 is not isolated from a cell or a plurality of cells (e.g., a tissue extract). In some embodiments, PTX3 is prepared by recombinant technology.

Purification of HC-HA

In some embodiments, the HC-HA is purified by any suitable method. In some embodiments, the HC-HA complex is purified by centrifugation (e.g., ultracentrifugation, gradient centrifugation), chromatography (e.g., ion exchange, affinity, size exclusion, and hydroxyapatite chromatography), gel filtration, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference).

In some embodiments, the HC-HA complex is purified by ultracentrifugation. The number of purification steps depends on the desired purity. In some embodiments, the purification comprises at least 2 rounds of ultracentrifugation. In some embodiments, the purification comprises more 2 rounds of ultracentrifugation. In some embodiments, the purification comprises at least 4 rounds of ultracentrifugation. In some embodiments, the method of purifying the isolated extract comprises: (d) dissolving the isolated extract in CsCl/4M guanidine HCl at the initial density of 1.35 g/ml, to generate a CsCl mixture, (e) centrifuging the CsCl mixture at 125,000×g for 48 h at 15° C., to generate a first purified extract, (f) extracting the first purified extract and dialyzing it against distilled water to remove CsCl and guanidine HCl, to generate a dialysate. In some embodiments, the method of purifying the isolated extract further comprises (g) mixing the dialysate with 3 volumes of 95% (v/v) ethanol containing 1.3% (w/v) potassium acetate at 0° C. for 1 h, to generate a first dialysate/ethanol mixture, (h) centrifuging the first dialysate/ethanol mixture at 15,000×g, to generate a second purified extract, and (i) extracting the second purified extract. In some embodiments, the method of purifying the isolated extract further comprises: (j) washing the second purified extract with ethanol (e.g., 70% ethanol), to generate a second purified extract/ethanol mixture; (k) centrifuging the second purified extract/ethanol mixture, to generate a third purified extract; and (l) extracting the third purified extract. In some embodiments, the method of purifying the isolated extract further comprises: (m) washing the third purified extract with ethanol (e.g., 70% ethanol), to generate a third purified extract/ethanol mixture; (n) centrifuging the third purified extract/ethanol mixture, to generate a forth purified extract; and (o) extracting the forth purified extract. The preferred purification method comprises four rounds of ultracentrifugation.

In some embodiments, the HC-HA complex is purified by immunoaffinity chromatography. In some embodiments, anti HC1 antibodies, anti-HC2 antibodies, or both are generated and affixed to a stationary support. In some embodiments, the unpurified HC-HA complex (i.e., the mobile phase) is passed over the support. In certain instances, the HC-HA complex binds to the antibodies (e.g., via interaction of (a) an HC1 antibody and HC1, (b) an HC2 antibody and HC2, or (c) both). In some embodiments the support is washed (e.g., with PBS) to remove any unbound or loosely bound molecules. In some embodiments, the support is then washed with a solution that enables elution of the HC-HA complex from the support (e.g., 1% SDS, 6M guanidine-HCl, or 8M urea).

In some embodiments, the HC-HA complex is purified by affinity chromatography. In some embodiments, HABP is generated and affixed to a stationary support. In some embodiments, the unpurified HC-HA complex (i.e., the mobile phase) is passed over the support. In certain instances, the HC-HA complex binds to the HABP. In some embodiments the support is washed (e.g., with PBS) to remove any unbound or loosely bound molecules. In some embodiments, the support is then washed with a solution that enables elution of the HC-HA complex from the support.

In some embodiments, the HC-HA complex is purified by a combination of HABP affinity chromatography, and immunoaffinity chromatography using anti HC1 antibodies, anti-HC2 antibodies, or both.

Bioreactor

In some embodiments, the HC-HA complex is made by use of live cells. In some embodiments, the method comprises contacting (a) hyaluronan (HA); (b) IαI; (c) TSG-6; and (d) PTX3; wherein one or more components is generated or expressed by a plurality of cells in a bioreactor.

In some embodiments, the method comprises HA that is obtained from a commercial supplier. In some embodiments, the method comprises HA that is generated by a plurality of cells in a bioreactor. In some embodiments, the plurality of cells constitutively generate HA. In some embodiments, the plurality of cells constitutively expresses HAS1, HAS2, HAS3, or a combination thereof. In some embodiments, the plurality of cells are contacted with at least one factor known to upregulate HAS1, HAS2, HAS3, or a combination thereof.

In some embodiments, the method comprises IαI isolated from serum. In some embodiments, the method comprises IαI that is not isolated from serum. In some embodiments, the method comprises IαI that is expressed by a cell or a plurality of cells in a bioreactor. In some embodiments, the plurality of cells constitutively expresses IαI.

In some embodiments, the method comprises TSG-6 that is isolated from a cell or a plurality of cells (e.g., a tissue extract). In some embodiments, the method comprises TSG-6 that is not isolated from a cell or a plurality of cells (e.g., a tissue extract). In some embodiments, the method comprises TSG-6 that is expressed by a cell or a plurality of cells in a bioreactor. In some embodiments, the cell or plurality of cells constitutively generates TSG-6. In some embodiments, the cell or plurality of cells constitutively expresses TSG-6. In some embodiments, the cell or plurality of cells is contacted with at least one factor known to upregulate TSG-6.

In some embodiments, the method comprises PTX3 that is isolated from a cell or a plurality of cells (e.g., a tissue extract). In some embodiments, the method comprises PTX3 that is not isolated from a cell or a plurality of cells (e.g., a tissue extract). In some embodiments, the method comprises PTX3 that is expressed by a cell or a plurality of cells in a bioreactor. In some embodiments, the cell or plurality of cells constitutively generates PTX3. In some embodiments, the cell or plurality of cells constitutively expresses PTX3. In some embodiments, the cell or plurality of cells is contacted with at least one factor known to upregulate expression of PTX3.

In some embodiments, a cell that constitutively (a) expresses IαI; (b) expresses TSG-6; or (c) PTX3, is generated by any suitable method. In some embodiments, a cell that constitutively (a) expresses IαI; (b) expresses TSG-6; or (c) expresses PTX3 is generated by introducing point mutations into a gene encoding (a); (b) TSG-6; or (c) PTX3. In some embodiments, the mutations are substitution mutations, deletion mutations, or insertion mutations.

In some embodiments, a cell that constitutively generates HA is produced by any suitable method. In some embodiments, a cell that constitutively generates HA is produced by introducing point mutations into a gene encoding HAS1, HAS2, HAS3, or a combination thereof. In some embodiments, the mutations are substitution mutations, deletion mutations, or insertion mutations. In some embodiments, a cell that constitutively generates HA is produced by contacting the cell with at least one factor known to upregulate HAS1, HAS2, HAS3, or a combination thereof.

Pharmaceutical Compositions

Disclosed herein, in certain embodiments, are methods of inhibiting osteoclast differentiation in an individual in need thereof, comprising administering to the individual a composition comprising product fetal support tissue product or an extract thereof. Disclosed herein, in certain embodiments, are methods of promoting mineralization by osteoblasts in an individual in need thereof, comprising administering to the individual a composition comprising a fetal support tissue product or an extract thereof. In some embodiments, the fetal support tissue product is substantially isolated placental amniotic membrane (PAM), umbilical cord amniotic membrane (UCAM), placenta, umbilical cord, chorion, amnion-chorion, or any combinations thereof. Disclosed herein, in certain embodiments, are methods of inhibiting bone resorption in an individual in need thereof, comprising administering to the individual a composition comprising a fetal support tissue product or an extract thereof. Disclosed herein, in certain embodiments, are methods of inhibiting bone remodeling in an individual in need thereof, comprising administering to the individual a composition comprising a fetal support tissue product or an extract thereof. Disclosed herein, in certain embodiments, are methods of balancing bone resorption and bone formation, comprising administering to an individual in need thereof a therapeutically-effective amount of a composition comprising a fetal support tissue product or an extract thereof. Disclosed herein, in certain embodiments, are methods of treating a disease, disorder, or condition characterized by excessive or undesired osteoclast differentiation, the methods comprising administering to an individual in need thereof a therapeutically-effective amount of a composition comprising a fetal support tissue product or an extract thereof. Disclosed herein, in certain embodiments, are methods of treating a disease, disorder, or condition characterized by excessive or undesired bone absorption by osteoclasts, the methods comprising administering to an individual in need thereof a therapeutically-effective amount of a composition comprising a fetal support tissue product or an extract thereof. Disclosed herein, in certain embodiments, are methods of treating a disease, disorder, or condition characterized by deficient or defective bone formation, the methods comprising administering to an individual in need thereof a therapeutically-effective amount of a composition comprising a fetal support tissue product or an extract thereof. Disclosed herein, in certain embodiments, are methods of treating arthritis, the methods comprising administering to an individual in need thereof a therapeutically-effective amount of a composition comprising a fetal support tissue product or an extract thereof. Disclosed herein, in certain embodiments, are methods of treating osteoporosis, the methods comprising administering to an individual in need thereof a therapeutically-effective amount of a composition comprising a fetal support tissue product or an extract thereof. Disclosed herein, in certain embodiments, are methods of treating alveolar bone degradation, the methods comprising administering to an individual in need thereof a therapeutically-effective amount of a composition comprising a fetal support tissue product or an extract thereof. Disclosed herein, in certain embodiments, are methods of treating Paget's disease, the methods comprising administering to an individual in need thereof a therapeutically-effective amount of a composition comprising a fetal support tissue product or an extract thereof. Disclosed herein, in certain embodiments, are methods of treating a bone tumor, the methods comprising administering to an individual in need thereof a therapeutically-effective amount of a composition comprising a fetal support tissue product or an extract thereof. In some embodiments, the compositions further comprise pharmaceutically acceptable diluent(s), excipient(s), or carrier(s). In some embodiments, the compositions further comprise an adhesive. In yet other embodiments, the compositions further comprise a penetration enhancer. In some embodiments, the compositions comprise a viscosity enhancing agent.

In other embodiments, the pharmaceutical compositions further comprise a further therapeutic agent. For a non-limiting disclosure of further therapeutic agents see the Combination Therapies section herein.

The pharmaceutical compositions described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compositions described herein are formulated as solutions. In some embodiments, the compositions are formulated as gels. In some embodiments, the compositions described herein are formulated as liposomes. In some embodiments, the compositions described herein are formulated as foams. In some embodiments, the compositions described herein are formulated as paints. In some embodiments, the compositions described herein are formulated as in situ forming spongy materials.

In some embodiments, the compositions disclosed herein are formulated for immediate release. In some embodiments, the compositions are formulated for controlled release (e.g., delayed release or sustained release). In some embodiments, the compositions are formulated for immediate release and controlled release. As used herein, "controlled release" includes delayed release, sustained release, extended release, variable release, pulsatile release and bi-modal release. The controlled-release aspect of the compositions described herein is imparted by any suitable excipients. By way of example only, such excipients include polymers and, viscosity enhancing agents.

In some embodiments, the compositions are biodegradable.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms,* Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

Excipients

In some embodiments, the compositions further comprise pharmaceutically acceptable diluent(s), excipient(s), or carrier(s).

In some embodiments, the compositions further comprise an antifoaming agent. "Antifoaming agents" reduce foaming during processing which can result in coagulation of aqueous dispersions, bubbles in the finished film, or generally impair processing. Exemplary anti-foaming agents include silicon emulsions or sorbitan sesquoleate.

In some embodiments, the compositions further comprise an antioxidant. "Antioxidants" include, for example, butylated hydroxytoluene (BHT), sodium ascorbate, ascorbic acid, sodium metabisulfite and tocopherol. In certain embodiments, antioxidants enhance chemical stability where required.

In some embodiments, the compositions further comprise a binder. "Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g.,) Klucel®, ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

In some embodiments, the compositions described herein further comprise buffering agents. For example to impart a physiological acceptable pH. Suitable buffering agent include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some embodiments, the compositions further comprise a carrier. A "carrier" or "carrier materials" include any commonly used excipients in pharmaceutics and should be selected on the basis of compatibility with compounds disclosed herein, such as, compounds of any of Formula D and the second agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

In some embodiments, the compositions further comprise a dispersing agent and/or viscosity modulating agents. "Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

In some embodiments, the compositions further comprise a diluent. The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some embodiments, the compositions further comprise a disintegrant. The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some embodiments, the compositions further comprise a preservative. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, the compositions described herein further comprise salts. In other embodiments, compositions described herein further comprise one or more salts in an amount sufficient to impart a physiologically acceptable osmolarity. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the compositions further comprise a solubilizer. "Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

In some embodiments, the compositions further comprise a suspending agent. "Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

In some embodiments, the compositions further comprise a surfactant. "Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

In some embodiments, the compositions further comprise a viscosity enhancing agent. "Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

In some embodiments, the compositions further comprise a wetting agent. "Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

The compositions described herein e.g., HC-HA, fetal support tissue extracts, fetal support powders and homogenates) can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions (e.g., HC-HA, fetal support tissue extracts, fetal support powders and homogenates) disclosed herein can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Solutions

In some embodiments, the compositions (e.g., HC-HA, fetal support tissue extracts, fetal support powders and homogenates) disclosed herein re formulated as solutions. Solutions include aqueous solutions, dispersions, and emulsions. See, e.g., Singh et al., *Encyclopedia of Pharmaceutical Technology*, $2^{nd}$ Ed., pp. 754-757 (2002).

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium docusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical compositions (e.g., HC-HA, fetal support tissue extracts, fetal support powders and homogenates) described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

Gels

In some embodiments, the compositions (e.g., HC-HA, fetal support tissue extracts, fetal support powders and homogenates) disclosed herein are formulated as a gel. In some embodiments, the compositions (e.g., HC-HA, fetal support tissue extracts, fetal support powders and homogenates) disclosed herein are formulated as solvent release gels. In some embodiments, the compositions (e.g., HC-HA, fetal support tissue extracts, fetal support powders and homogenates) disclosed herein are formulated as actinic radiation curable gels. In some embodiments, the compositions (e.g., HC-HA, fetal support tissue extracts, fetal support powders and homogenates) disclosed herein are formulated as thermoreversible gels. In other embodiments, the compositions (e.g., HC-HA, fetal support tissue extracts, fetal support powders and homogenates) disclosed herein are formulated hydrogels.

As used herein, "gels", sometimes referred to as jellies, are semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels are hydrophobic or hydrophilic. The base of a hydrophobic gel may be liquid paraffin with polyethylene or fatty oils gelled with colloidal silica, or aluminum or zinc soaps. The base of hydrophilic gels usually consists of water, glycerol, or propylene glycol gelled with a suitable gelling agent (e.g., tragacanth, starch, cellulose derivatives, carboxyvinylpolymers, and magnesium-aluminum silicates).

Polymers composed of polyoxypropylene and polyoxyethylene form thermoreversible gels when incorporated into aqueous solutions. These polymers have the ability to change from the liquid state to the gel state at temperatures close to body temperature.

Paints

In some embodiments, the compositions (e.g., HC-HA, fetal support tissue extracts, fetal support powders and homogenates) disclosed herein are formulated as paints. As used herein, a "paint", also known as film formers, means solutions comprised of a solvent, a monomer or polymer, an tissue product or extract thereof, and optionally one or more pharmaceutically-acceptable excipients. After application to a target bone, the solvent evaporates leaving behind a thin coating comprised of the monomers or polymers, and the active agent. The coating protects active agents and maintains them in an immobilized state at the site of application. This decreases the amount of active agent that may be lost and correspondingly increases the amount delivered to the subject. By way of non-limiting example, paints include collodions, and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers. The paints contemplated for use herein, are flexible such that they do not interfere with the growth or movement of a bone or joint. In some embodiments, the paints are applied as a liquid (i.e. solution, suspension, or emulsion), a semisolid (i.e. a gel, foam, paste, or jelly) or an aerosol.

Foams

In some embodiments, the compositions (e.g., HC-HA, fetal support tissue extracts, fetal support powders and homogenates) disclosed herein is formulated as a foam. Examples of suitable foamable carriers for use in the compositions e.g., HC-HA, fetal support tissue extracts, fetal support powders and homogenates) disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic side-chains, cellulose and derivatives thereof, agar and derivatives thereof, such as agar stabilized with polyacrylamide, polyethylene oxides, glycol methacrylates, gelatin, gums such as xanthum, guar, karaya, gellan, arabic, tragacanth and locust bean gum, salts thereof (e.g., sodium alginate), or combinations thereof.

Liposomes

In some embodiments, the compositions (e.g., HC-HA, fetal support tissue extracts, fetal support powders and homogenates) disclosed herein are formulated as liposomes or lipid particles. Phospholipids that are gently dispersed in an aqueous medium form multilayer vesicles with areas of entrapped aqueous media separating the lipid layers. Sonication, or turbulent agitation, of these multilayer vesicles results in the formation of single layer vesicles, commonly referred to as liposomes. Suitable phospholipids for use in the formation of liposomes, include for example, phosphatidyl cholines, ethanolamines and serines, sphingomyelins, cardiolipins, plasmalogens, phosphatidic acids and cerebrosides. Preferred phospholipids are, for example, phosphatidyl choline, phosphatidyl ethanolmine, phosphatidyl serine, phosphatidyl inositol, lysophosphatidyl choline, phosphatidyl glycerol.

In some embodiments, a liposome formulation may further comprise a lipophilic additive. Examples of such additives include by way of example only, stearylamine, phosphatidic acid, tocopherol, cholesterol, cholesterol hemisuccinate and lanolin extracts.

Creams and Lotions

In some embodiments, the compositions (e.g., HC-HA, fetal support tissue extracts, fetal support powders and homogenates) disclosed herein are formulated as creams. In certain instances, creams are semisolid (e.g., soft solid or thick liquid) formulations that include a fetal support tissue product described herein (e.g., a flat tissue product sheet, a pulverized tissue product, or a homogenized tissue product) dispersed in an oil-in-water emulsion or a water-in-oil emulsion.

Ointments

In some embodiments, the compositions (e.g., HC-HA, fetal support tissue extracts, fetal support powders and homogenates) disclosed herein are formulated as ointments. In certain instances, ointments are semisolid preparations that soften or melt at body temperature.

Pastes

In some embodiments, the compositions (e.g., HC-HA, fetal support tissue extracts, fetal support powders and homogenates) disclosed herein are formulated as pastes. In certain instances, pastes contain at least 20% solids. In certain instances, pastes are ointments that do not flow at body temperature.

Patches

In some embodiments, the compositions (e.g., HC-HA, fetal support tissue extracts, fetal support powders and homogenates) disclosed herein are administered via a patch. In some embodiments, the compositions described herein are dissolved and/or dispersed in a polymer or an adhesive. In some embodiments, a film, a patch disclosed herein is constructed for continuous, pulsatile, or on demand delivery of a composition described herein.

Wound Dressings

In some embodiments, the compositions (e.g., HC-HA, fetal support tissue extracts, fetal support powders and homogenates) disclosed herein are administered via a wound dressing. Wound dressings include, but are not limited to gauzes, transparent film dressings, hydrogels, polyurethane foam dressings, hydrocolloids and alginates.

Implants/Prosthesis

In some embodiments, the compositions (e.g., HC-HA, fetal support tissue extracts, fetal support powders and homogenates) disclosed herein are administered via implants and prostheses. In some embodiments, the compositions (e.g., HC-HA, fetal support tissue extracts, fetal support powders and homogenates) are administered by bone implants or bone stents.

In some embodiments, the compositions (e.g., HC-HA, fetal support tissue extracts, fetal support powders and homogenates) disclosed herein are administered via a bone implant. In some embodiments, the bone implant is an osseointegrated implant. As used herein, an "osseointegrated implant" means a three dimensional implant containing pores into which osteoblasts and supporting connective tissue can migrate. In some embodiments, the bone implant comprises a composition described herein. In some embodiments, the bone implant is a dental implant. In some embodiments, the bone implant is used for knee or joint replacement. In some embodiments, the bone implant is a craniofacial prosthesis (e.g., an artificial ear, orbital prosthesis, nose prosthesis).

In some embodiments, the compositions (e.g., HC-HA, fetal support tissue extracts, fetal support powders and homogenates) disclosed herein are administered via a bone stent. In some embodiments, the compositions (e.g., HC-HA, fetal support tissue extracts, fetal support powders and homogenates) disclosed herein are coated onto the outside of the stent. In some embodiments, the compositions (e.g., HC-HA, fetal support tissue extracts, fetal support powders and homogenates) disclosed herein elute from the stent into the surrounding bone. In some embodiments, the bone stents are inserted into the intramedullary canal of a bone. In some embodiments, the bone stent is placed in the sinus tarsi. In some embodiments, the bone stent in placed in a knee or joint. In some embodiments, the bone stent is placed in a bone fracture. In some embodiments, the bone stent is expandable or contractable.

Miscellaneous

In some embodiments, the pharmaceutical composition described herein comprise microencapsulated tissue products and/or extracts thereof (e.g., HC-HA). In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

In some embodiments, the fetal support tissue products or extracts thereof (e.g., HC-HA) are incorporated within nanoparticles, microparticles, or microspheres.

Microspheres usually have a spherical shape, although irregularly-shaped microparticles are possible. Microspheres may vary in size, ranging from submicron to 1000 micron diameters. The fetal support tissue products and extracts thereof are encapsulated in microspheres by any suitable methods. Generally, the agent is dispersed or emulsified, using stirrers, agitators, or other dynamic mixing techniques, in a solvent containing a wall-forming material. Solvent is then removed from the microspheres, and thereafter the microsphere product is obtained.

Nanoparticles are also contemplated for use with the fetal support tissue products and extracts described herein. Nanoparticles are material structures of about 100 nm or less in size. One use of nanoparticles in pharmaceutical compositions is the formation of suspensions as the interaction of the particle surface with solvent is strong enough to overcome differences in density. Nanoparticle suspensions are sterilized as the nanoparticles are small enough to be subjected to sterilizing filtration (see, e.g., U.S. Pat. No. 6,139,870, herein incorporated by reference for such disclosure). Nanoparticles comprise at least one hydrophobic, water-insoluble and water-indispersible polymer or copolymer emulsified in a solution or aqueous dispersion of surfactants, phospholipids or fatty acids. The nanoparticles may be obtained by any suitable methods. These methods include vaporization methods, such as free jet expansion, laser vaporization, spark erosion, electro explosion and chemical vapor deposition; physical methods involving mechanical attrition (e.g., "pearlmilling" technology, Elan Nanosystems), super critical $CO_2$ and interfacial deposition following solvent displacement. In one embodiment, the solvent displacement method is used. The size of nanoparticles produced by this method is sensitive to the concentration of polymer in the organic solvent; the rate of mixing; and to the surfactant employed in the process. Continuous flow mixers provide the necessary turbulence to ensure small particle size. One type of continuous flow mixing device that is optionally used to prepare nanoparticles has been described (Hansen et al J Phys Chem 92, 2189-96, 1988). In other embodiments, ultrasonic devices, flow through homogenizers or supercritical $CO_2$ devices may be used to prepare nanoparticles.

Combination Therapies

Disclosed herein, in certain embodiments, are methods of inhibiting osteoclast differentiation in an individual in need thereof, comprising administering to the individual a composition comprising a fetal support tissue product or an extract thereof. Disclosed herein, in certain embodiments, are methods of inhibiting bone resorption in an individual in need thereof, comprising administering to the individual a composition comprising a fetal support tissue product or an extract thereof. Disclosed herein, in certain embodiments, are methods of inhibiting bone remodeling in an individual in need thereof, comprising administering to the individual a composition comprising a fetal support tissue product or an extract thereof. Disclosed herein, in certain embodiments, are methods of balancing bone resorption and bone formation, comprising administering to an individual in need thereof a therapeutically-effective amount of a composition comprising a fetal support tissue product or an extract thereof. Disclosed herein, in certain embodiments, are methods of treating a disease, disorder, or condition characterized by excessive or undesired osteoclast differentiation, the methods comprising administering to an individual in need thereof a therapeutically-effective amount of a composition comprising a fetal support tissue product or an extract thereof. Disclosed herein, in certain embodiments, are methods of treating arthritis, the methods comprising administering to an individual in need thereof a therapeutically-effective amount of a composition comprising a fetal support tissue product or an extract thereof. In some embodiments, the arthritis is osteoarthritis, rheumatoid arthritis, psoriatic arthritis, or any combination thereof. Disclosed herein, in certain embodiments, are methods of treating osteoporosis, the methods comprising administering to an individual in need thereof a therapeutically-effective amount of a composition comprising a fetal support tissue product or an extract thereof. Disclosed herein, in certain embodiments, are methods of treating alveolar bone degradation, the methods comprising administering to an individual in need thereof a therapeutically-effective amount of a composition comprising a fetal support tissue product or an extract thereof. Disclosed herein, in certain embodiments, are methods of treating Paget's disease, the methods comprising administering to an individual in need thereof a therapeutically-effective amount of a composition comprising a fetal support tissue product or an extract thereof. Disclosed herein, in certain embodiments, are methods of treating a bone tumor, the methods comprising administering to an individual in need thereof a therapeutically-effective amount of a composition comprising a fetal support tissue product or an extract thereof. In some embodiments of any of the aforementioned methods, the methods further comprise administering a further therapeutic agent.

In some embodiments, the pharmaceutical compositions disclosed herein result from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

In some embodiments, the further therapeutic agent is a calcium supplement, a calcium salt, or a combination thereof. In some embodiments, the further therapeutic agent is calcium carbonate, coral calcium, calcium citrate, calcium phosphate, calcium lactate, a calcium chelate (e.g., calcium malate, calcium aspartate, calcium fumarate), or any combinations thereof.

In some embodiments, the further therapeutic agent is a NSAID. In some embodiments, the further therapeutic agent is a salicylate, a propionic acid derivative, an acetic acid derivative, and enolic acid derivative, a fenamic acid derivative, a selective COX-2 inhibitor, a sulphonanilide, or any combinations thereof. In some embodiments, the further agent is aspirin, diflunisal, salsalate, ibuprofen, naproxen, fenoprofen, ketoprofen, dexketoprofen, flurbiprofen, oxaprozin, loxoprofen, indomethacin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxibm, nimesulide, licofelone, or any combinations thereof.

In some embodiments, the further therapeutic agent is a corticosteroid. In some embodiments, the further therapeutic agent is a hydrocortisone type corticosteroid, an acetonide, a betamethasone type corticosteroid, a corticosteroid ester (e.g., a halogenated corticosteroid or a labile prodrug ester). In some embodiments, the further therapeutic agent is hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate, hydrocortisone-17-butyrate, 17-aceponate, 17-buteprate, Prednicarbate, or any combinations thereof.

In some embodiments, the further therapeutic agent is a hyaluronan or sodium hyaluronate.

In some embodiments, the further therapeutic agent is a DMARD (disease-modifying antirheumatic drug). In some embodiments, the further therapeutic agent is adalimumab, azathioprine, chloroquine, hydroxychloroquine, cyclosporine, D-penicillamine, etanerecpt, golimumab, infliximab, leflunomide, methotrexatem minocycline, rituximab, sulfasalazine, sodium aurothiomalate, auranofin, or any combinations thereof.

In some embodiments, the further therapeutic agent is a bisphosphonate. In some embodiments, the further therapeutic agent is a N-containing bisphosphonate. In some embodiments, the further therapeutic agent is a non-N-containing bisphosphonate. In some embodiments, the further therapeutic agent is etidronate, clodronate, tiludronate, pamidronate, neridronate, olpadronate, alendronate, ibandronate, risedronate, zoledronate, or any combination thereof.

In some embodiments, the further therapeutic agent is an estrogen analog. In some embodiments, the further therapeutic agent is estrodiol, phytoestrogen, diethylstilbestrol, or any combinations thereof.

In some embodiments, the further therapeutic agent is a selective estrogen receptor modulator (SERM). In some embodiments, the further therapeutic agent is raloxifene, clomifene, femarelle, ormeloxifene, tamoxifen, toremifene, lasofoxifene, or any combinations thereof.

In some embodiments, the further therapeutic agent is a member of the calcitonin-like protein family. In some embodiments, the further therapeutic agent is Calcitonin.

In some embodiments, the further therapeutic agent is parathyroid hormone. In some embodiments, the further therapeutic agent is a recombinant parathyroid hormone. In some embodiments, the further therapeutic agent is Teriparatide.

In some embodiments, the further therapeutic agent is a RANKL inhibitor. In some embodiments, the further therapeutic agent is denosumab.

In some embodiments, the further therapeutic agent is a chemotherapeutic. Any suitable chemotherapeutic agent is contemplated for use with the fetal support tissue product compositions disclosed herein. Suitable chemotherapeutic agents include those that are efficacious in the treatment of osteosarcoma, Ewing's sarcoma, chondrosarcoma, and fibrosarcoma. In some embodiments, the further therapeutic agent is ifosfamide, etopside, carboplatin, cisplatin, cyclophosphamide, doxorubicin, epirubicin, methotrexate, PEG-interferon alfa-2b, or any combinations thereof.

In some embodiments, the further therapeutic agent is radiation therapy, proton therapy, or a combination thereof.

In some embodiments, the further therapeutic agent is sodium fluoride.

In some embodiments, the further therapeutic agent is Strontium ranelate.

In some embodiments, the further therapeutic agent is Metastron (i.e., strontium-89 chloride).

EXAMPLES

Example 1: AM Tissue and its Derivatives Prevent Differentiation of Osteoclasts in Response to RANKL Cell Culture and Treatment Macrophage RAW 264.7 cells were cultivated in DMEM/10% FBS until 80% confluence, harvested with enzyme-free dissociation buffer, and seeded at 169 cells/mm$^2$ with α-MEM/10% FBS differentiation media without phenol red.

After 24 h, seeded macrophage RAW 264.7 cells were treated with 50 ng/ml RANKL (except Neg CTL) and simultaneously treated with either PBS1× (Pos CTL), AME (200 μg/ml Protein), HC-HA (25 μg/ml HA), or on either side (epithelium, stroma or basement membrane) of intact AM (iAM), denuded AM (dAM), and lyophilized AM (lAM). Cells were observed for cell death and formation of multinucleated cell (osteoclast) for a period of 5-7 days.

TRAP Assay

After termination, cells were fixed with acetone and stained with tartrate resistant acid phosphatase leukocyte kit (TRAP). Cell lysate was also collected with 1% Triton X-100 extraction buffer for analysis with TRAP Colorimetric Assay.

Figure 2:
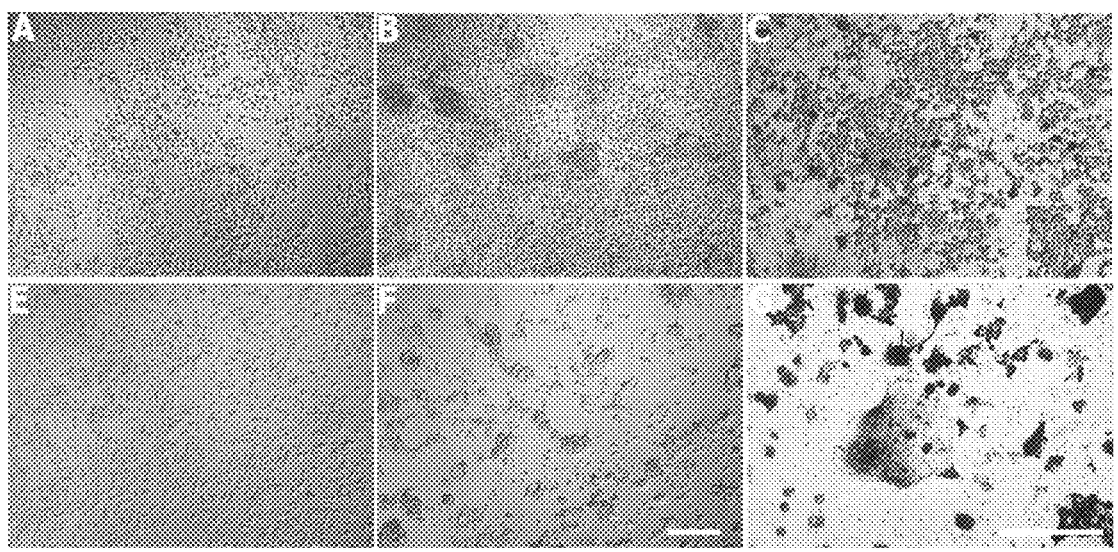
FIG. 2 exemplifies macrophage RAW 264.7 cells cultured with (E-G, Pos CTL) and without (A-C, Neg CTL) 50 ng/ml RANKL stimulation. Osteoclasts began to form on Day 3 (F) and complete differentiation was observed on Day 5 (G) as evidenced by positive TRAP staining. Bar=200 μm.
Figure 3:
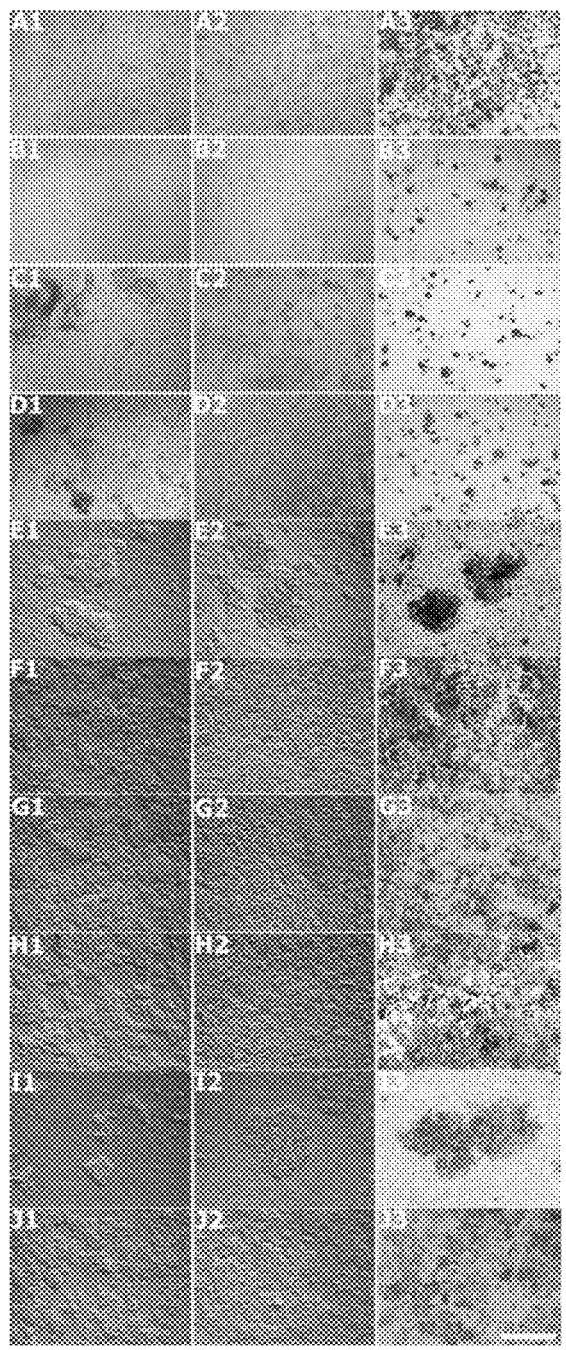
FIG. 3 exemplifies macrophage RAW 264.7 cells stimulated with 50 ng/ml RANKL and cultured with soluble amniotic membrane extract (AME) (A), HC-HA complex purified from AM (HC-HA) (B), AM lysate (AML) (C), AM powder (AMP) (D), and on the epithelial side of intact amniotic membrane (iAM)(E), the stromal side of iAM (F), the basement membrane side of epithelially-denuded AM (dAM) (G), the stromal side of dAM (H), the epithelial side of lyophilized amniotic membrane lAM (I), or the stromal side of lyophilized amniotic membrane lAM (J). Cell morphology on Day 3 (Column 1), Day 5 (A2-D2), and Day 6 (E2-J2). TRAP staining (Column 3) revealed no large multinucleated osteoclasts when cultured on AM and its derivatives. Bar=200 µm.

Formation of large multinucleated osteoclast cells was observed for the Pos CTL (FIG. 2 E-G) but not Neg CTL (FIG. 2 A-C). TRAP staining (FIG. 3) revealed no large multinucleated osteoclast cells when RAW 264.7 cells were cultured on the epithelial side of intact amniotic membrane (iAM), the stromal side of iAM (F), the basement membrane side of epithelially-denuded AM (dAM) (G), the stromal side of dAM (H), the epithelial side of lyophilized amniotic membrane lAM (I), or the stromal side of lyophilized amniotic membrane lAM (J).

Figure 4:
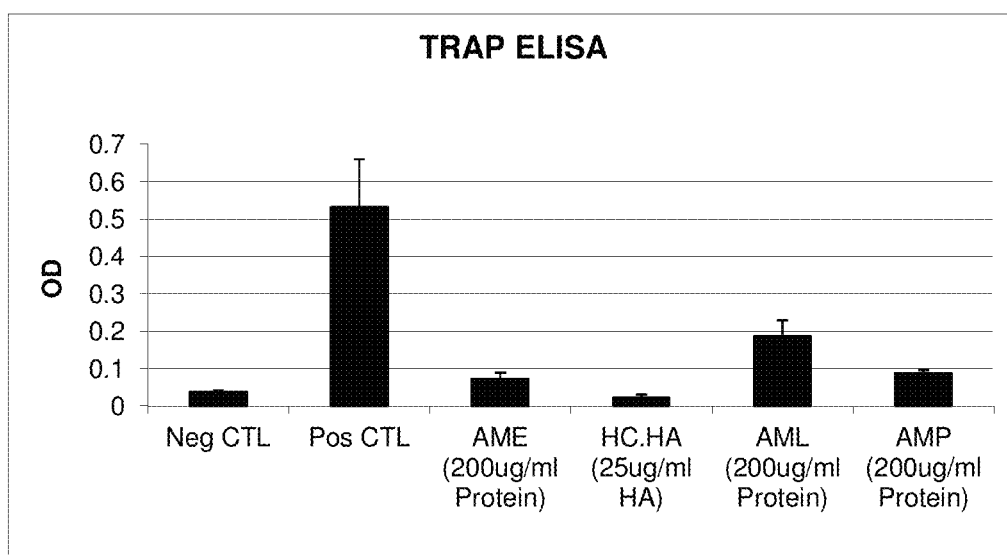
FIG. 4 exemplifies Neg CTL showing significantly lower (p=0.001) TRAP reading compared to the Pos CTL. Inhibitory action for osteoclast formation was seen on all AM derivatives (200 µg/ml protein) with HC-HA (25 µg/ml HA) being the most potent followed by AME, AMP, and AML.

Following TRAP Colorimeteric analysis, the Neg CTL showed significantly lower (p=2.9E-12) TRAP reading compared to the Pos CTL. Inhibitory action for osteoclast formation was seen for all AM derivatives (FIG. 4) with or without gamma irradiation.

qPCR

Total RNAs were also collected for quantitative measurement of RANK, β3-Integrin, and NFATc1 transcripts.

Figure 5:
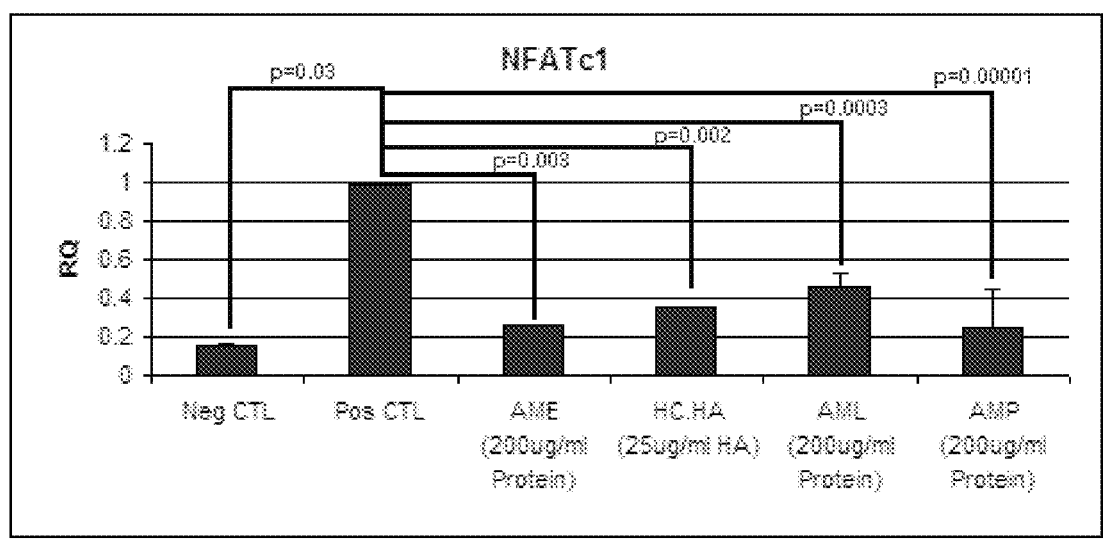
FIG. 5 exemplifies mRNA expression of NFATc1 (measured by quantitative PCR on Day 5 as being significantly downregulated by all AM derivatives (p<0.05).
Figure 6:
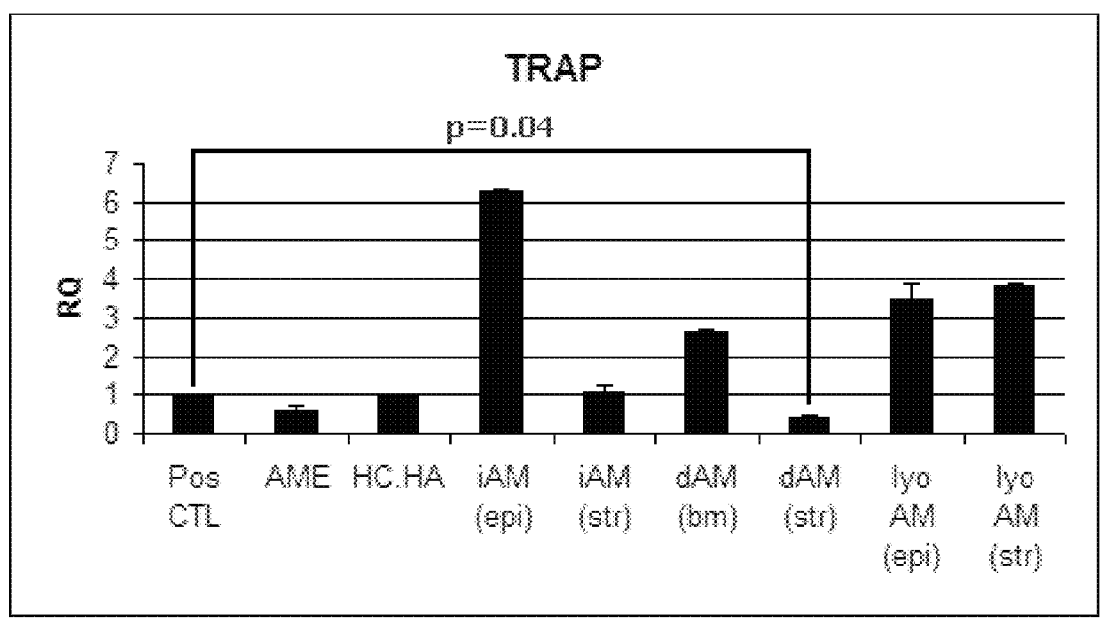
FIG. 6 exemplifies Neg CTL showing significantly lower (p=2.9E-12) TRAP reading compared to Pos CTL. Statistically significant inhibitory action for osteoclast formation (all p<0.05) was seen on all AM tissues including epithelial side of iAM, stromal side of iAM, basement membrane side of dAM and stromal side of dAM. Inhibitory action of osteoclast was also preserved after gamma irradiation of all AM tissues.
Figure 7:
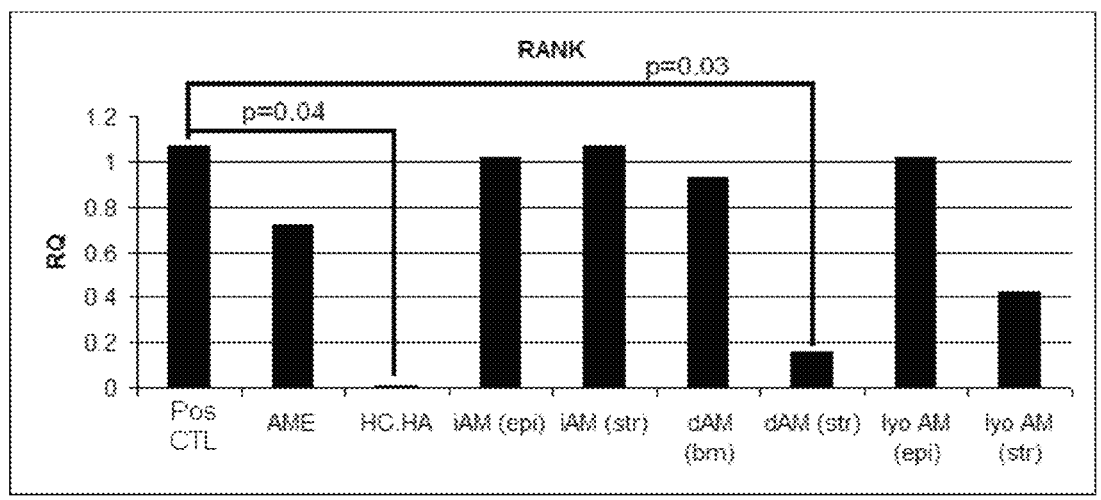
FIG. 7 exemplifies mRNA expression of RANK on Day 7 as being significantly downregulated for both HC-HA and stromal side of dAM.
Figure 8:
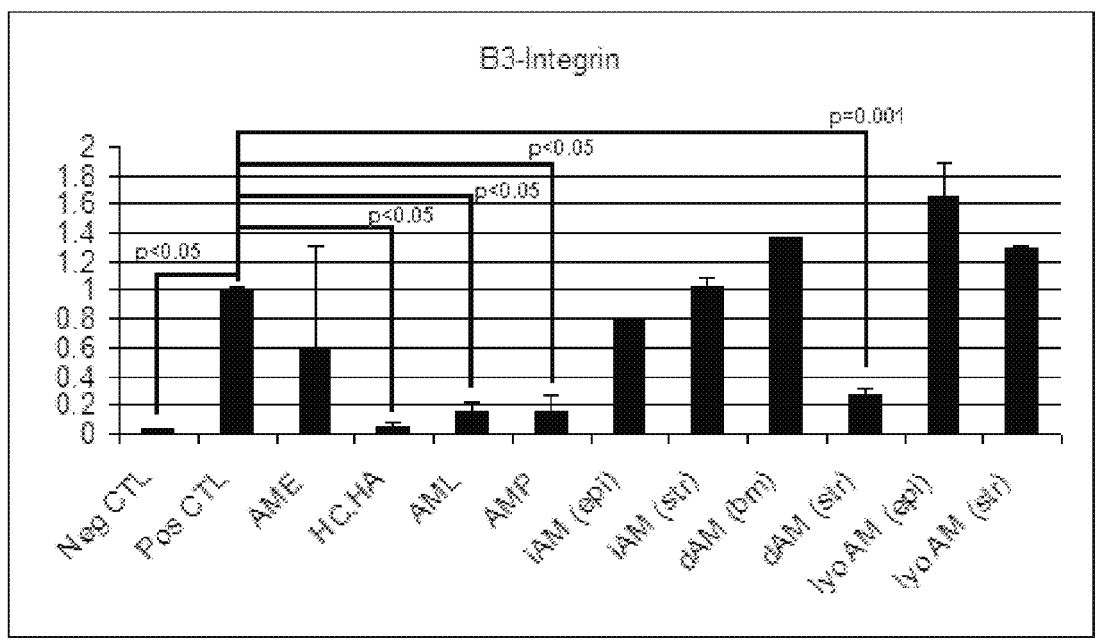
FIG. 8 exemplifies expression of β3-integrin, which is required for normal osteoclast differentiation, as being significantly downregulated by HC-HA, AML, AMP, and stromal side of dAM. Suppression of β3-integrin by AME is statistically significant on Day 5 (p=0.000001).

Quantitative RT-PCR revealed that levels of NFATc1 mRNA were significantly downregulated (p<0.05) in response to all AM derivatives (FIG. 5). Expression of RANK was found to be significantly downregulated for both HC-HA and stromal side of dAM (FIG. 7). Expression of β3-integrin (FIG. 8), which is required for normal osteoclast differentiation, was found to be significantly downregulated by HC-HA, AML, AMP, and stromal side of dAM. Suppression of β3-integrin by AME is statistically significant on Day 5 (p=0.000001).

Example 2: AME, AML, and AMP Inhibit Osteoclast Formation from RANKL Stimulated RAW 264.7 Macrophage Cells Murine RAW 264.7 macrophage cells were seeded at a density of 4.0×10$^3$ cells/96 well (30-40% confluent), cultured in α-MEM media without Phenol Red and supplemented with 10% FBS, 100 μg/ml penicillin & streptomycin. 24 hours after seeding, cells were treated with or without 50 ng/ml RANKL stimulation. Experimental groups were simultaneously treated with AMP, AML or AME with protein concentration of 200 μg/ml. On Day 5, the culture was terminated and analyzed by TRAP staining and TRAP Colorimetric Assay.

The result from TRAP staining (FIG. 2) shows that osteoclasts (multi-nucleated cells) were not found on the Neg CTL while large multi-nucleated cells were found on the Pos CTL. AME inhibited osteoclast formation but did not inhibit RAW macrophage cell proliferation (FIG. 2a). Osteoclast formation and RAW macrophage cell proliferation were also inhibited by AML-1 and AML-2 from 2 different donors (FIG. 11), but such inhibition was not complete because small multi-nucleated cells could be seen after TRAP staining. Osteoclast formation and RAW macrophage cell proliferation were also inhibited by AMP from 5 different donors (FIG. 11) at the same protein concentration of 200 µg/ml as AML.

Figure 11:
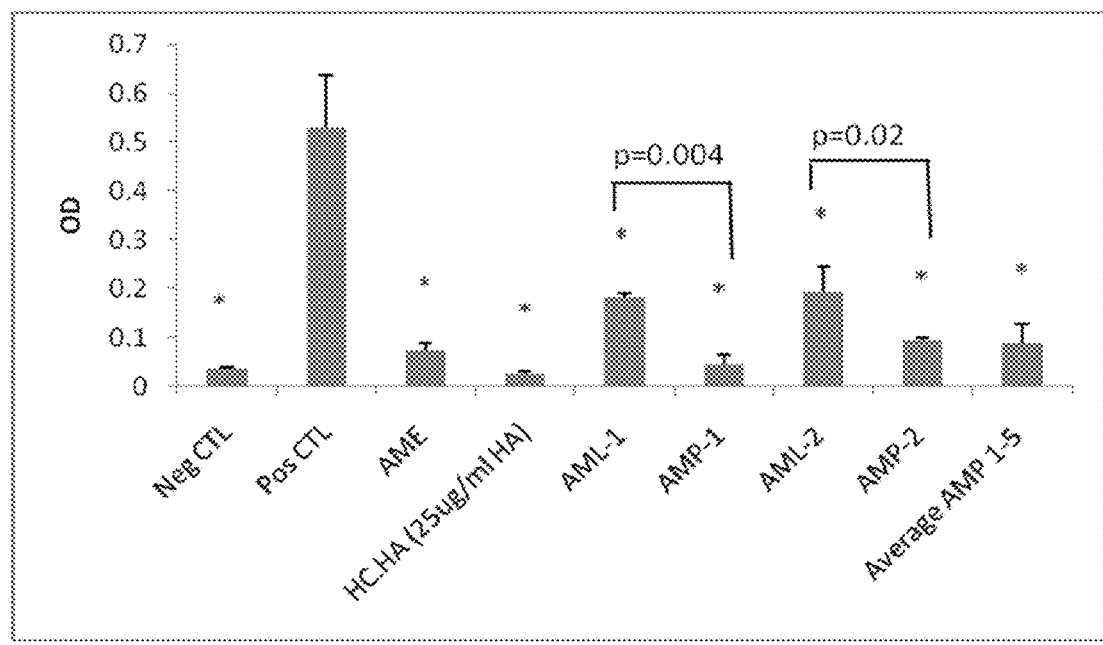
FIG. 11 exemplifies the performance of several tissue products (AME, HC-HA, AML, AMP) in inhibiting osteoclast formation. All AM derivates significantly inhibit osteoclast formation, and AMP prepared from different donors (AMP 1-5) consistently showed inhibitory activity that were more potent than AML.

The result from TRAP staining shows that the inhibitory action for osteoclast formation was seen on all AM derivatives. There was no significant difference between the TRAP Colorimetric Assay reading between AMP and AME (Table 1). For two donors, the TRAP ELISA reading for AMP is significantly lower than AML (Table 1) from the same donor ($p=0.04$ and $p=0.02$) at the same protein concentration 200 µg protein/ml (FIG. 11).

TABLE 1 p-values

| Comparison | | p = value |
|---|---|---|
| AMP 1-5 | AME | 0.24 |
| AMP 1-2 | AML 1-2 | 1.02E−05 |

TABLE 2

OD readings and p-values

| Conditions | OD ± standard deviation | p-value (compared to Pos CTL) |
|---|---|---|
| Neg CTL | 0.037 ± 0.0035 | 0.0013 |
| Pos CTL | 0.53 ± 0.11 | — |
| AME | 0.073 ± 0.015 | 0.0028 |
| HC.HA (25 µg/ml HA) | 0.023 ± 0.0081 | 0.0023 |
| AML-1 | 0.18 ± 0.0097 | 0.0067 |
| AMP-1 | 0.046 ± 0.018 | 0.0022 |
| AML-2 | 0.19 ± 0.052 | 0.0034 |
| AMP-2 | 0.093 ± 0.0055 | 0.0036 |
| Mean AMP 1-5 | 0.087 ± 0.041 | 0.0017 |

TABLE 3

Protein Content of AMP from 5 different donors

| | BCA Protein Reading (µg/ml) | Powder used/ml (mg/ml) | Protein(µg)/ Powder Weight (mg) | Total Powder Weight (mg) | Total Protein(mg) from 1 whole AM |
|---|---|---|---|---|---|
| AMP-1 | 13933 | 44.6 | 312 | 1340 | 419 |
| AMP-2 | 8777 | 30 | 293 | 880 | 257 |
| AMP-3 | 14527 | 42 | 346 | 1250 | 432 |
| AMP-4 | 16516 | 49 | 337 | 1836 | 619 |
| AMP-5 | 22727 | 51.2 | 444 | 1408 | 625 |

Example 3: Powder Derived from Amniotic Membrane (AMP), Chorion (CHP), Amnion-Chorion (ACP), Placenta (PCP), Whole Umbilical Cord (UCP), or Umbilical Cord AM (UCAP) Inhibits Osteoclast Formation from RANKL Stimulated RAW 264.7 Macrophage Cells Murine RAW 264.7 macrophage cells were seeded at a density of $4.0\times10^3$ cells/96 well (30-40% confluent), cultured in α-MEM media without Phenol Red and supplemented with 10% FBS, 100 µg/ml penicillin & streptomycin. 24 hours after seeding, cells were treated with or without 50 ng/ml RANKL stimulation. Experimental groups were simultaneously treated with AMP, CHP, ACP, PLP, UCP, and UCAP with protein concentration of 100 µg/ml. On Day 5, the culture was terminated and analyzed by TRAP Colorimetric Assay.

Figure 12:
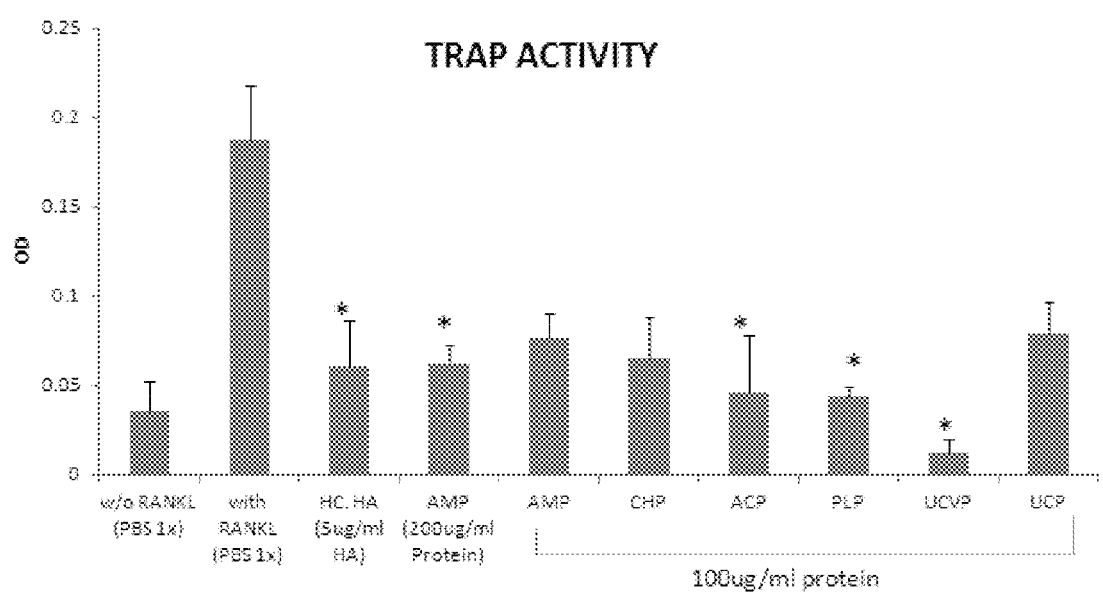
FIG. 12 exemplifies the performance of AMP in inhibiting osteoclast formation. Powders were made from amniotic membrane (AMP), chorion (CHP), amnion-chorion (ACP), whole placenta (PLP), whole umbilical cord (UCP), and umbilical cord amniotic membrane (UAMP). Like HC-HA (5 µg/ml), AMP (200 µg/ml), ACP (100 µg/ml), PLP (100 µg/ml), and WUC (100 µg/ml) significantly inhibit osteoclast formation.

Osteoclast formation was inhibited by all powder derived from amniotic membrane (AMP), chorion (CHP), amnion-chorion (ACP), placenta (PCP), whole umbilical cord (UCP), and umbilical cord AM (UCAP) (FIG. 12).

Example 4: HC-HA Inhibits the Formation of Osteoclasts from RANKL Stimulated RAW 264.7 Macrophage Cells Murine RAW 264.7 macrophage cells were seeded at a density of $4.0\times10^3$ cells/96 well (30-40% confluent), cultured in α-MEM media without Phenol Red and supplemented with 10% FBS, 100 µg/ml penicillin & streptomycin. 24 hours after seeding, cells were treated with or without 50 ng/ml RANKL stimulation.

Experimental groups were simultaneously treated with high molecular weight HA or HC-HA prepared at a series of HA concentrations (0, 0.008, 0.04, 0.2, 1, 5, and 25 µg/ml). On Day 5, the culture was terminated and analyzed by TRAP staining and TRAP ELISA.

Figure 9A:
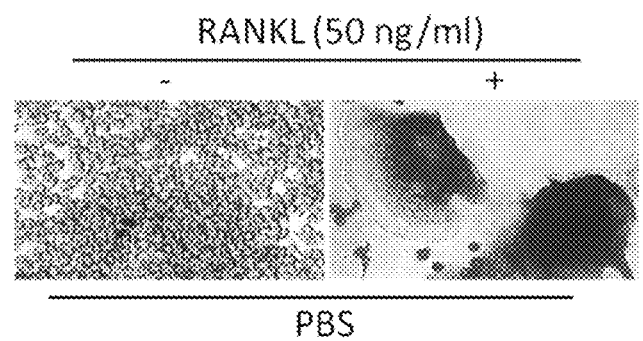
FIGS. 9A-9E exemplify the effects of nHC-HA on osteoclastogenesis. RAW264.7 cells is effectively induced into osteoclasts at Day 6 with 50 ng/ml RANKL(a). The inhibition of osteoclast formation is dose dependent on nHC-HA purified from AM. (HC-HA) concentrations inhibit osteoclast formation while the highest concentration of high molecular weight HA (100 µg/ml) does not inhibit the osteoclast formation (b). The color picture of TRAP colorimetric assay is provided. The lighter of the color, the more inhibition of the TRAP activity is (c). nHC-HA as low as 0.08 µg/ml significantly inhibits the osteoclast formation (d). IC50 of HC-HA on the osteoclast formation is calculated to be about 0.1 µg/ml (e).

The result from TRAP staining shows that osteoclasts (multi-nucleated cells) are not found on the negative control while large multi-nucleated cells are found on the positive control (FIG. 9A).

Figure 9B:
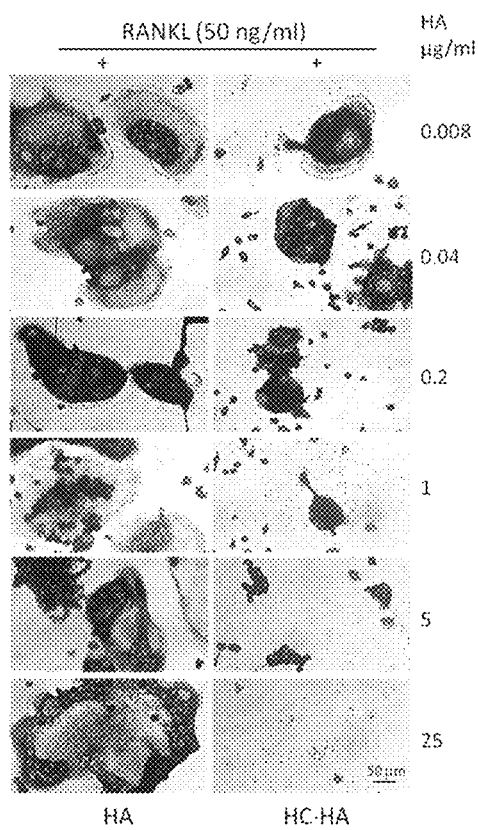

Even at the highest concentration (25 µg/ml), HA does not inhibits the formation of multinucleated cells and the expression of TRAP, In contrast, the inhibition by HC-HA is detected as low as at 0.08 µg/ml, and dose-dependently increased until the multinucleated cells are completely eliminated at 25 µg/ml (FIG. 9B).

Figure 9C:
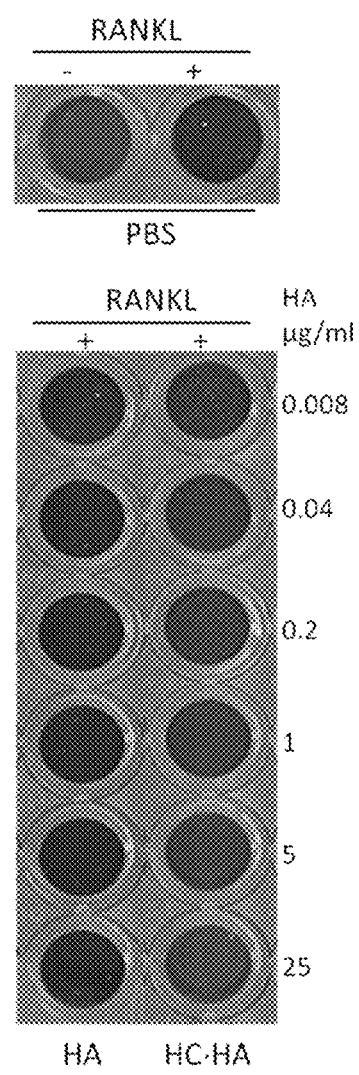
Figure 9D:
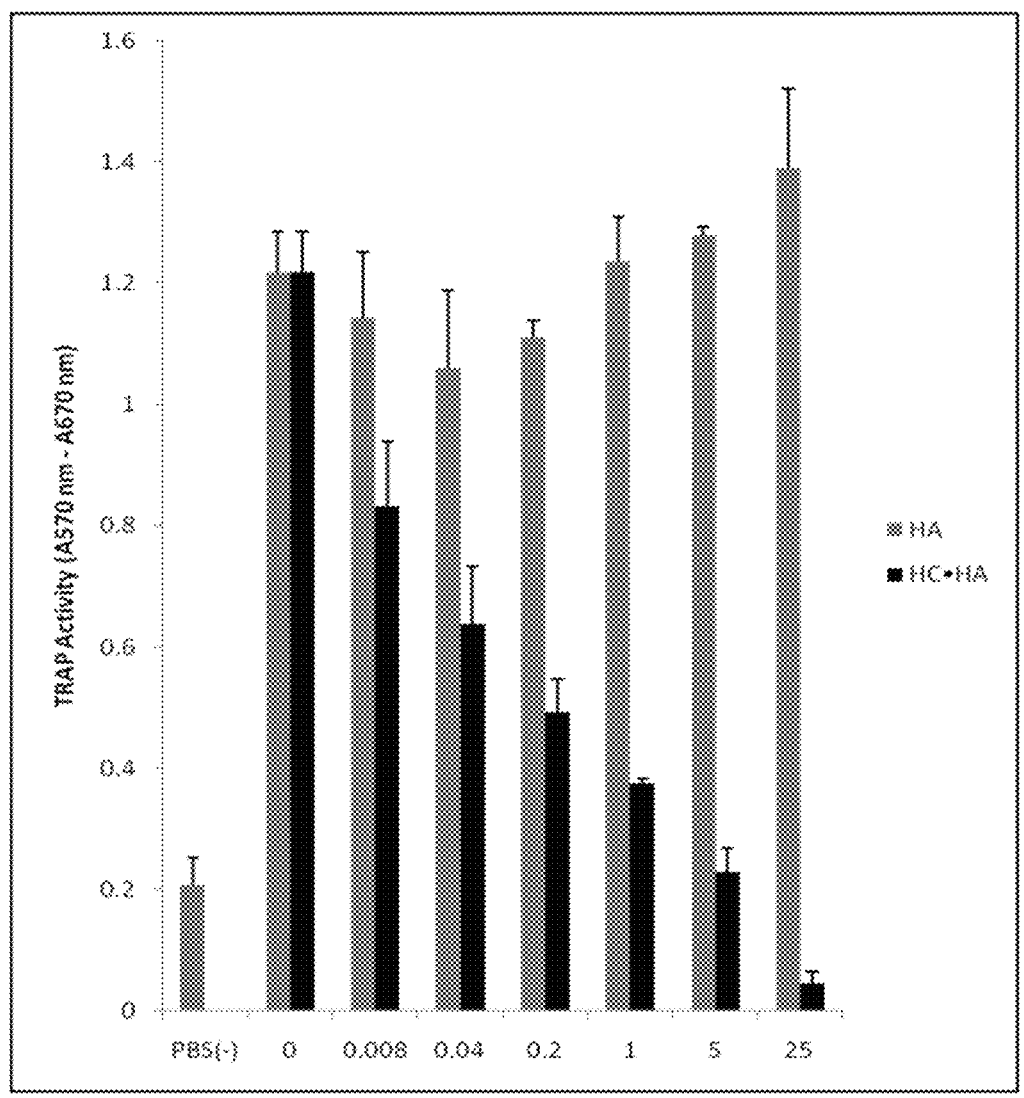
Figure 9E:
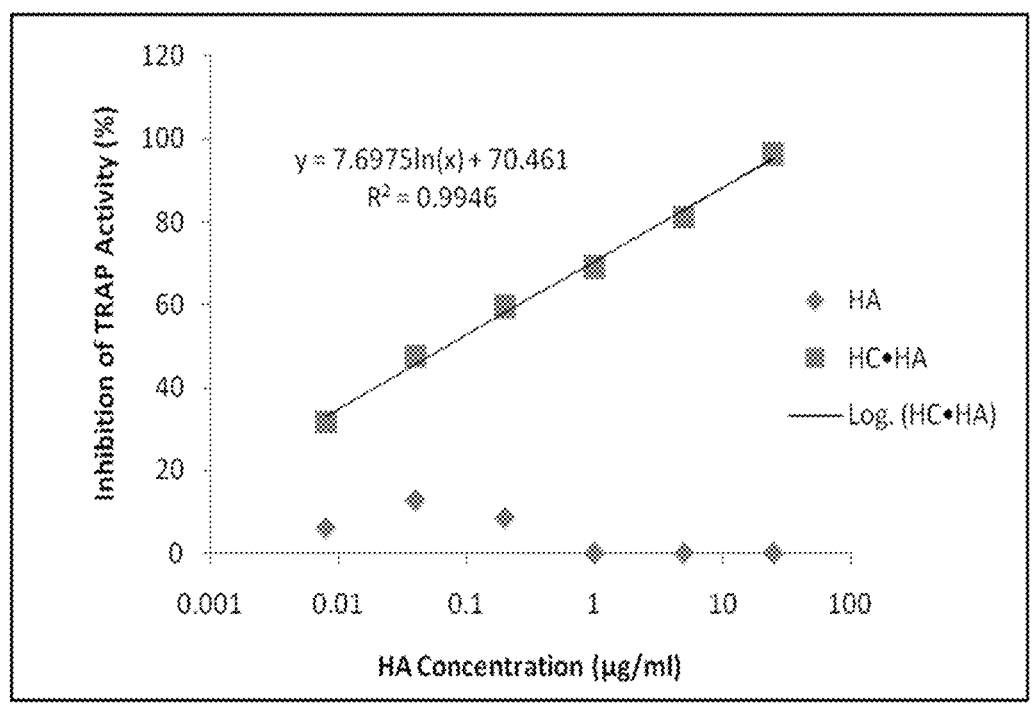
Figure 10A:
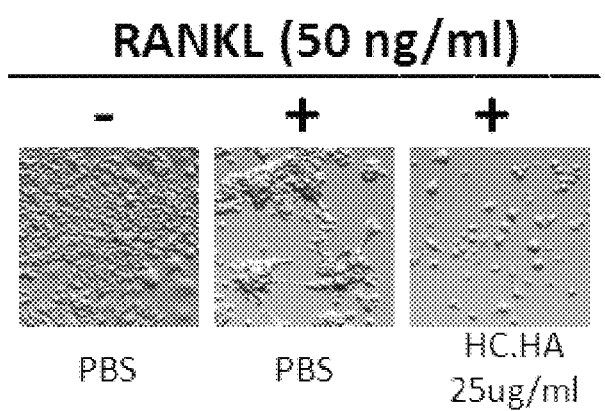
FIGS. 10A-10F exemplify the effects of AMP (amniotic membrane powder) on osteoclastogenesis. Previous results can be reliably reproduced (a). Like HC-HA, AMP dose (0-500 µg/ml protein) dependently inhibits the osteoclast formation (b). The color picture of TRAP colorimetric assay is provided (c and d). Osteoclast inhibition by AMP is measured by TRAP Colorimetric assay (e). IC50 of AMP on the osteoclast formation is calculated to be about 20.1 µg/ml (f).
Figure 10B:
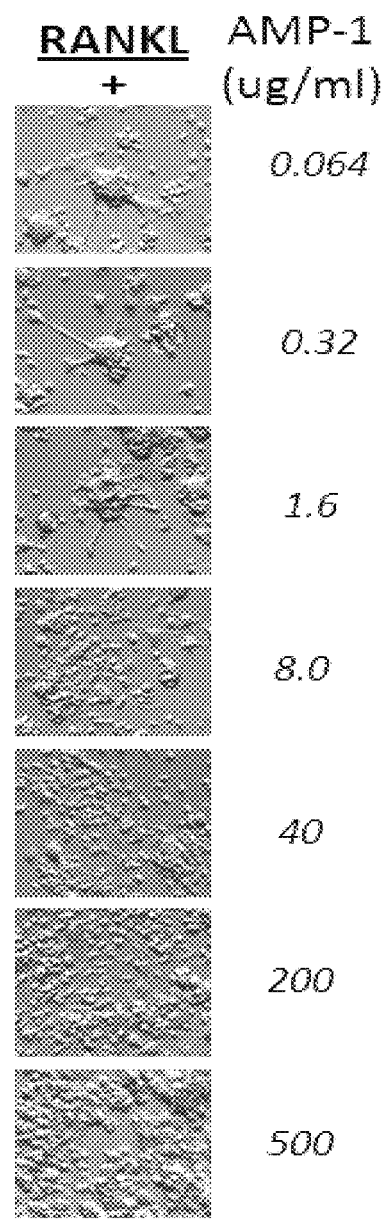
Figure 10C:
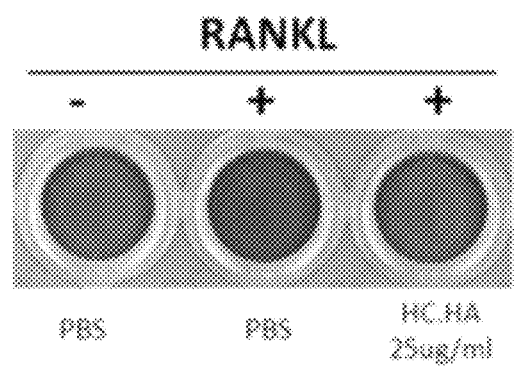
Figure 10D:
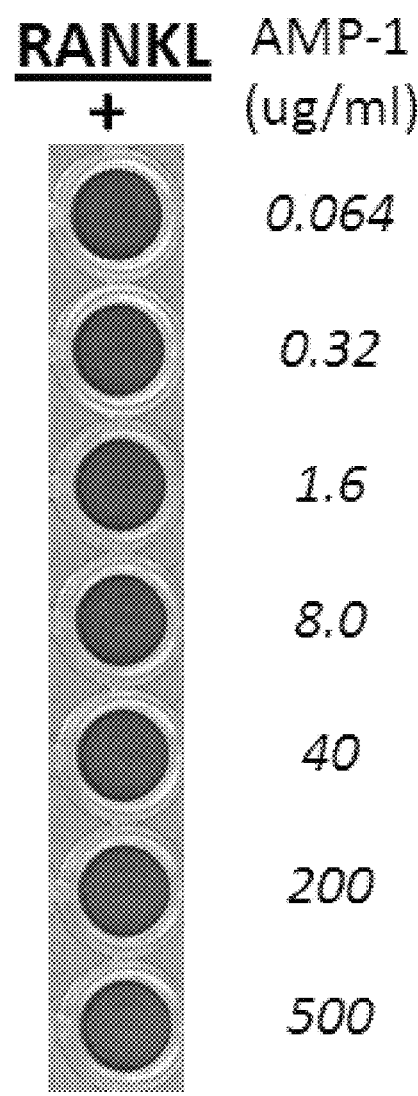
Figure 10E:
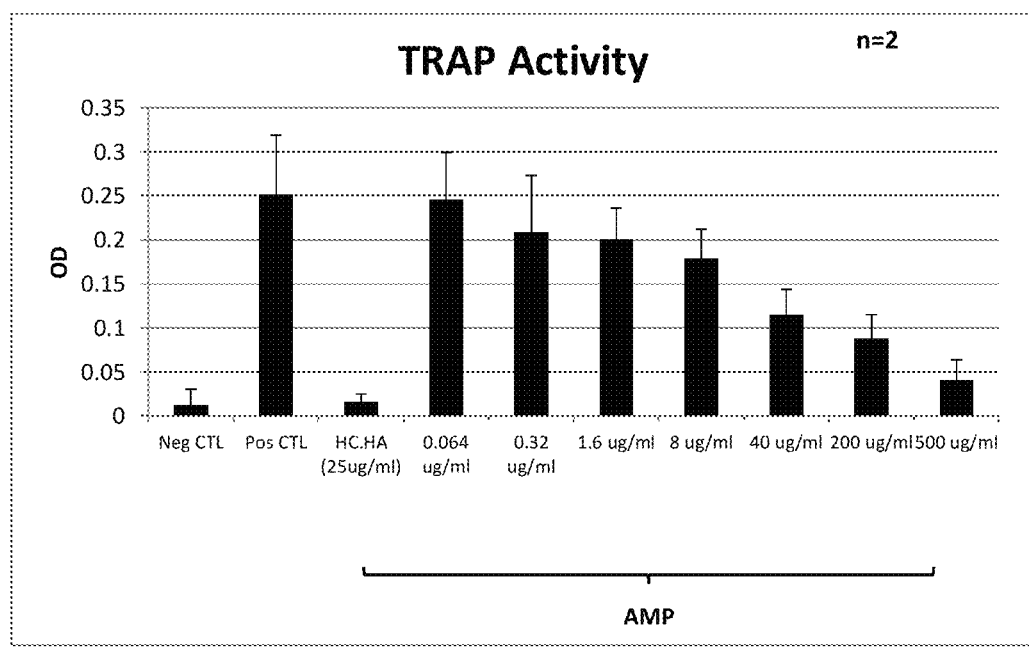
Figure 10F:
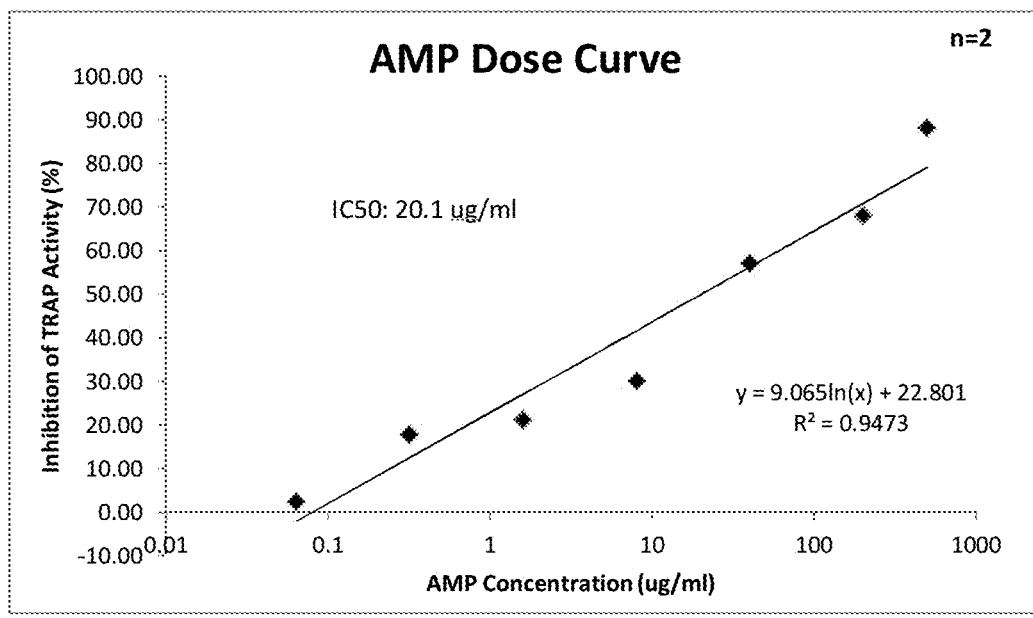

These observations are also confirmed by quantitatively measured TRAP activity (FIGS. 9C and 9D). From the TRAP Colorimetric assay, the IC50 of HC-HA's inhibition on the osteoclast formation induced by RANKL is 0.1 µg/ml (FIG. 9E).

Example 5: AMP Promotes the Mineralization of Osteoblasts

Osteoblast precursor MC3T3-E1 cells were maintained in DMEM/10% FBS but were re-suspended into α-MEM/10% FBS and seeded at $1\times10^5$/ml on 24 well plastic (2 ml per well, and designated as Day 1 from here onwards) for 2 days.

The culture medium was replaced with either PBS (Neg. Ctrl), osteoblast-inducing reagents (0.2 mM ascorbic acid 2-phosphate and 10 mM glycerol 2-phosphate, Pos. Ctrl), or osteoblast-inducing reagents plus 0.1 µg/ml HC-HA or 125 µg/ml AMP. The cell culture medium was changed every 3 days until on Day 18. From Day 8 onwards, the osteoblast-inducing reagents was additionally supplemented with melatonin (50 ng/ml).

At Day 18, cells were assayed with alizarin red staining (ARS) to measure the mineralization of differentiated osteoblasts. Negative control was not stained by ARS but the positive control was stained in red (FIG. 13).

Figure 13:
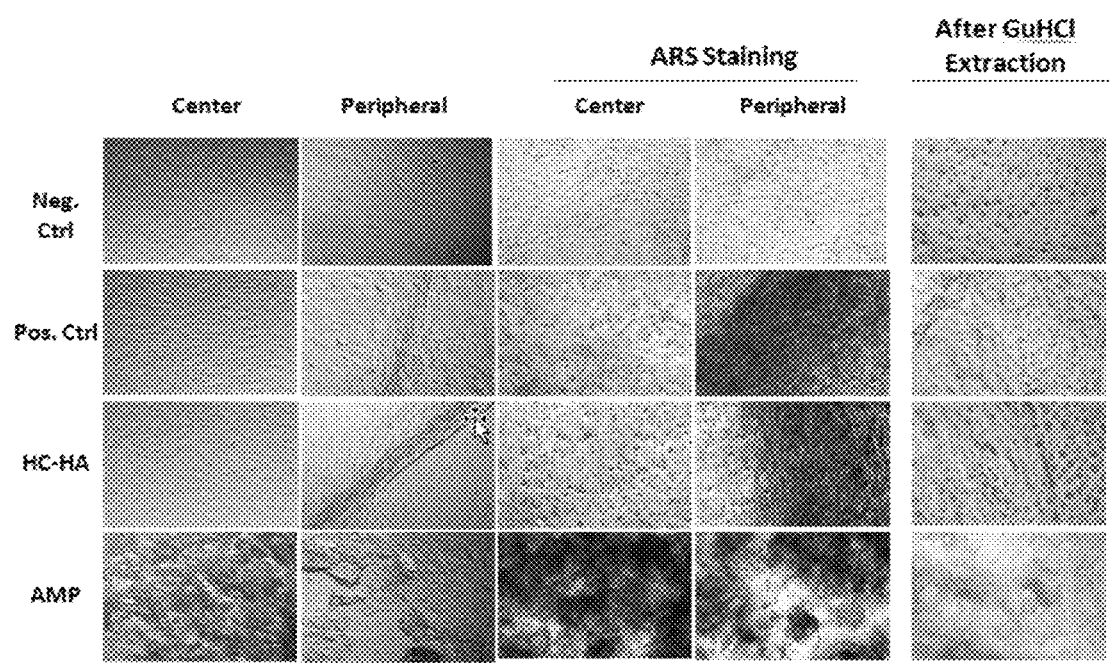
FIG. 13 exemplifies the effects of AMP on osteogenesis. After cultivation for 7 days, the cell morphology of groups with induction (Pos Ctrl, HC-HA, and AMP) is changed: a compact layer of cells appears in the periphery in Pos Ctrl and HC-HA, but becomes clusters in AMP. Alizarin staining (ARS) shows only the periphery is stained in Pos Ctrl and HC-HA, bur both the periphery and the center are stained in AMP.

Treatment with HC-HA (0.1 µg/ml) has a similar staining as that of the positive control (FIG. 13). However, treatment with AMP (125 µg/ml) yields much darker staining (AMP), indicating that more minerals are generated (FIG. 14).

Figure 14:
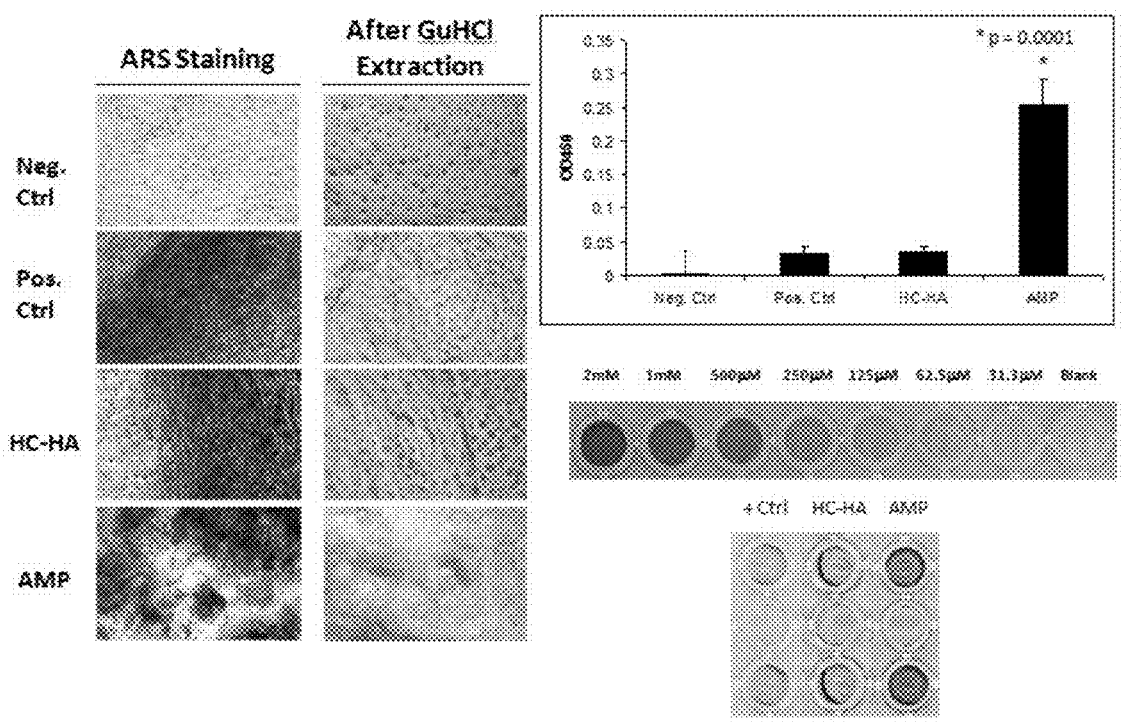
FIG. 14 exemplifies the effects of AMP on bone matrix mineralization. When ARS is measured quantitatively, cell treated with AMP (125 µg/ml) significantly promotes the mineralization (p=0.0001).
Figure 15:
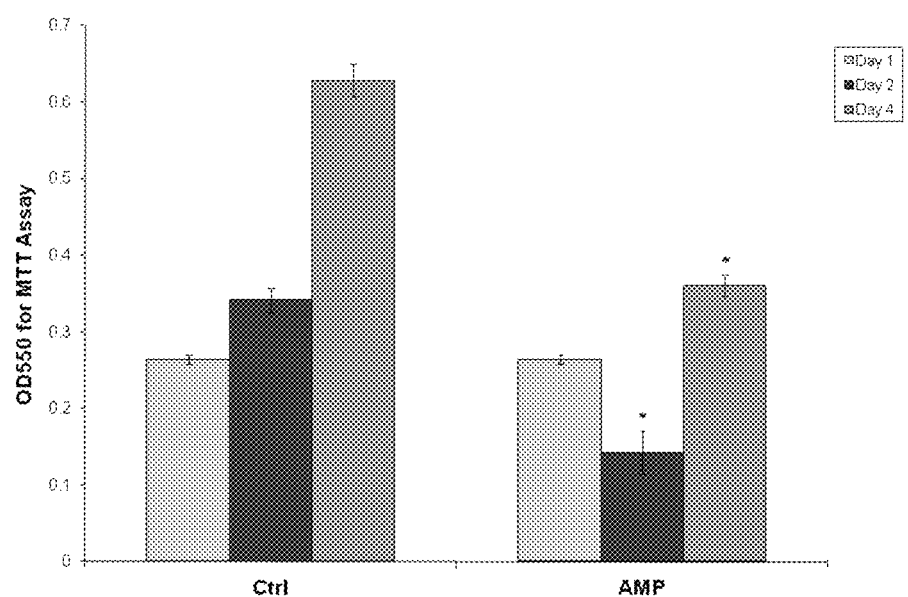
FIG. 15 exemplifies the effects of AMP on the proliferation of osteoblasts. The cell proliferation in the control is increased from Day 1 to Day 4. In contrast, with the treatment of AMP (125 µg/ml), the cell proliferation is first decreased from Day 1 to Day 2, and then increased from Day 2 to Day 4. However, compared to that of the control, the cell proliferation with AMP treatment is significantly lower at Day 2 and Day 4 (p<0.05).
Figure 16:
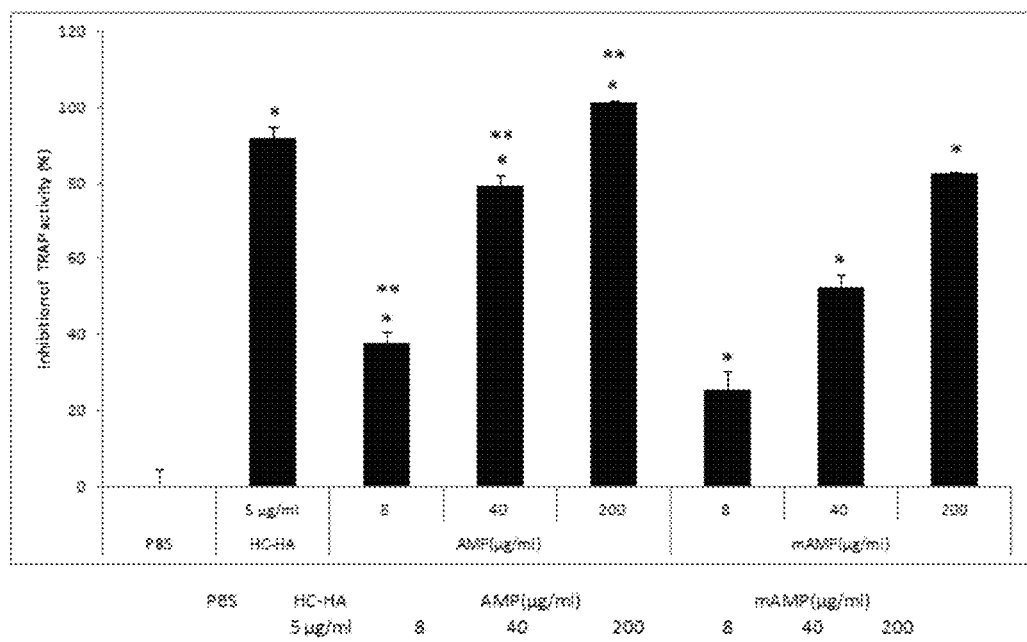
FIG. 16 exemplifies the effects of AMP and mAMP on osteoclastogenesis. mAMP is a powder of injectable Amino-Fix, which is prepared by Mimedx Group (Kennesaw, Ga.) using Purion$^{SM}$ Process, which is different from what is disclosed in this invention based on heat drying and other chemical processing. Both AMP and mAMP are suspended into PBS and prepared at a series of concentrations (8, 40, and 200 µg protein/nal) and added to RANKL-induced RAW264.7 cells. After 5 days treatment, the TRAP activity in cells is measured. AMP significantly and dose-dependently inhibits TRAP activity (p<0.05). Additionally, AMP is significantly more potent than mAMP at the same concentration (p<0.05).

The differences were also observed after ARS stained cells were removed by 4 M GnCl, showing less cells were left in AMP treated wells (FIG. 14). Some cells migrate from the monolayer into the AMP particles and use it as a scaffold for differentiation and mineralization.

Quantitative measurement of ARS (FIG. 14) shows HC-HA (0.1 µg/ml) does not significantly increase or decrease the mineralization when compared to the positive control ($p>0.05$). In contrast, cells treated with AMP (125 µg/ml) significantly promotes the mineralization compared to either the positive control or HC-HA ($p=0.0001$). The color changes related to the concentrations of alizarin red or in samples are shown in FIG. 14.

Example 6: Use for the Treatment of an Arthritic Joint

An individual with rheumatoid arthritis is identified. A pharmaceutical composition for injection comprising HC-HA is prepared.

The composition is injected at the arthritic joints of the individual.

Example 7: Use in the Treatment of Osteolysis

An individual with an area of decalcified bone is identified. A wound dressing comprising placental powder is prepared.

The tubular tissue graft is surgically placed around the area of decalcified bone.

Example 8: Use of an Implant in the Treatment of Osteolysis

An individual with an area of decalcified bone is identified. An implant coated in HC-HA is prepared.

The implant is surgically placed near the area of decalcified bone.

Example 9: Use of an Patch in the Treatment of Alveolar Bone Degradation

An individual with alveolar bone degradation is identified. A sheet of substantially-flat amnion-chorion patch is prepared.

The patch is placed on an alveolar bone at the site of alveolar bone degradation.

Example 10: Use of an Orthopaedic Prosthesis in the Treatment of Osteoarthritis An individual with a damaged knee due to osteoarthritis is identified. An orthopedic prosthesis comprising chorion homogenate derivative is prepared.

The orthopedic prosthesis is surgically placed to replace the individual's damaged knee.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of promoting or inducing osteogenesis in an individual in need thereof, comprising contacting a bone or joint in the individual with a therapeutically-effective amount of a fetal support tissue that comprises: (a) cells, substantially all of which are dead, and (b) HC-HA; thereby promoting or inducing osteogenesis in the individual.

2. The method of claim 1, wherein the fetal support tissue is placental amniotic membrane (PAM), umbilical cord amniotic membrane (UCAM), placenta, umbilical cord, chorion, amnion-chorion, or combinations thereof.

3. The method of claim 1, wherein the fetal support tissue is frozen or previously frozen.

4. The method of claim 1, wherein the fetal support tissue is a sheet, a powder, or a homogenate.

5. The method of claim 1, wherein the fetal support tissue is cryopreserved, lyophilized, terminally sterilized, or a combination thereof.

6. The method of claim 1, wherein contacting the joint with the fetal support tissue comprises injecting the fetal support tissue into the joint.

7. The method of claim 1, wherein contacting the bone or joint with the fetal support tissue comprises wrapping a fetal support tissue sheet around the bone or joint.

8. The method of claim 1, wherein the individual in need thereof has arthritis, osteoporosis, a bone tumor, Paget's Disease, alveolar bone degradation, or any combination thereof.

9. The method of claim 1, wherein contacting the bone or joint with the fetal support tissue comprises contacting the bone or joint with a medical device comprising the fetal support tissue.

10. The method of claim 9, wherein the medical device is a patch, implant, orthopedic prosthesis, or bone stent.

* * * * *